(12) United States Patent
Hata et al.

(10) Patent No.: US 7,863,033 B2
(45) Date of Patent: Jan. 4, 2011

(54) LACTOBACILLUS LIVING BODY ACTIVATING LACTOBACILLUS PREPARATION AND PREVENTIVE OR THERAPEUTIC AGENT FOR LIVING BODY INFECTION

(75) Inventors: Tadayo Hata, Tondabayashi (JP); Hitoshi Toshimori, Osaka (JP); Toshiyuki Maruoka, Toyonaka (JP)

(73) Assignee: BHPH Company Limited, Nassau (BS)

( * ) Notice: Subject to any disclaimer, the term of this patent is extended or adjusted under 35 U.S.C. 154(b) by 1052 days.

(21) Appl. No.: 10/566,085

(22) PCT Filed: Jul. 27, 2004

(86) PCT No.: PCT/JP2004/010639

§ 371 (c)(1),
(2), (4) Date: Jan. 27, 2006

(87) PCT Pub. No.: WO2005/012503

PCT Pub. Date: Feb. 10, 2005

(65) Prior Publication Data

US 2008/0293126 A1 Nov. 27, 2008

(30) Foreign Application Priority Data

Jul. 30, 2003 (JP) ............................. 2003-203802

(51) Int. Cl.
*C12N 1/20* (2006.01)
(52) U.S. Cl. ................................. 435/252.9; 424/93.45
(58) Field of Classification Search ........................ None
See application file for complete search history.

(56) References Cited

U.S. PATENT DOCUMENTS

| 4,314,995 A | * | 2/1982 | Hata et al. ................ 424/93.45 |
| 4,579,740 A | * | 4/1986 | Matrozza ...................... 426/59 |
| 6,340,585 B1 | | 1/2002 | Elli et al. |
| 6,521,443 B1 | | 2/2003 | Zink et al. |

FOREIGN PATENT DOCUMENTS

| DE | 27 38 652 A1 | 3/1979 |
| EP | 1 038 951 A1 | 9/2000 |
| EP | 1 048 215 A1 | 11/2000 |
| FR | 2 400 901 | 3/1979 |
| GB | 1 585 863 | 3/1981 |
| JP | 52-102419 | 8/1977 |
| JP | 2000-189105 | 7/2000 |
| JP | 2000-279166 | 10/2000 |
| JP | 2000-316567 | 11/2000 |
| JP | 2001-333766 | 12/2001 |
| JP | 2003-171292 | 6/2003 |

OTHER PUBLICATIONS

Asahara et al., Antimicrobial Agents and Chemotherapy, Jun. 2001, vol. 45, p. 1751-1760.*
Ouwehand et al., Journal of Food Science, vol. 66, No. 6, pp. 856-858, 2001.*
B. Breuer, et al.; "Inducible resistance against nisin in *Lactobacillus casei*;" Arch. Microbiol.; vol. 165; No. 2; 1996; pp. 114-118 (3 Sheets.).

* cited by examiner

*Primary Examiner*—Irene Marx
(74) *Attorney, Agent, or Firm*—Kratz, Quintos & Hanson, LLP

(57) ABSTRACT

There has been effort to develop a lactobacillus that would be useful as a probiotic, and to develop a lactobacillus which would colonize and proliferate in lesions of infection, eliminating the causal bacteria.

This problem was resolved by developing a *Lactobacillus casei* species having the following key properties. (1) The species can be grown in the presence of any of one to four amino acids as a nitrogen source necessary for growth. (2) When a growth-promoting culture medium is inoculated with the species and *Escherichia coli* in the same count and subjected to anaerobic mixed culturing at 37° C., the final count of lactobacilli is 50% or more of the coliform count. (3) Upon cultivation in an appropriate culture medium, the final pH value is 4.0 or below, and the highest acidity is 1.5% or more. (4) The species is resistant to 5% bile salts. (5) The species produces an antibiotic.

2 Claims, 5 Drawing Sheets

LACTOBACILLUS LIVING BODY ACTIVATING LACTOBACILLUS PREPARATION AND PREVENTIVE OR THERAPEUTIC AGENT FOR LIVING BODY INFECTION

TECHNICAL FIELD

The present invention relates to a *Lactobacillus casei* species having excellent properties not provided by conventionally known bacteria, to a living body activating lactobacillus preparation having this bacteria as a principal component which is extremely useful for restoring, maintaining and promoting health and for improving the growth and quality of plants and animals, and to a lactobacillus preparation which is highly effective in preventing and treating infections of animals and plants.

BACKGROUND ART

An infection occurs when bacteria invade and multiply inside a living body and the body exhibits disease symptoms, and once bacteria begin to multiply in the body, the body reacts in a variety of ways, and various symptoms such as redness and swelling appear. Use of drugs such as antibiotics is appropriate at this point, and helps to cure the infection. However, when it is too late to use antibiotics, or when their use is inappropriate, or when use is interrupted in the course of therapy, or when enough of the drug cannot get to the infection, reduction or removal of the pathogen is prevented and treatment is ultimately unsuccessful in many cases. In addition, problems have recently risen affecting both the bacteria and their hosts, complicating circumstances so that infections last longer or are more severe and difficult to treat.

The first victory for humans in the war against infectious disease occurred in the mid-twentieth century with the advent of antibiotics, beginning with penicillin. Unlike previous drugs, this drug was hailed as a "magic bullet" for its dramatic effects: it seemed that infection had been conquered, and that the term "infectious disease" would soon be obsolete. Bacteria are not easily conquered, however, and overuse of antibiotics led to the appearance and spread of drug-resistant bacteria. Having survived and regrouped, the bacteria are on the attack again. Bacteria that have acquired resistance have succeeded in transmitting this resistance across species boundaries through the conjugation of special DNA fragments (resistance genes) called R-plasmids. As a result, medicine truly seems to be on the brink of defeat due to the prevalence and spread of methicillin-resistant *Staphylococcus aureus* (MRSA), a major cause of hospital-based infections, and other multidrug-resistant bacteria including vancomycin-resistant *Enterococcus* (VRE), *Pseudomonas aeruginosa, Mycobacterium tuberculosis, Shigella flexneri* and the like.

For example, 80% of adults are said to suffer from periodontal disease, in which surrounding tissues that support the teeth including the gums, cement, periodontal ligaments, alveolar bone and the like become inflamed and are gradually destroyed. This is caused by bacteria that preferentially colonize and form plaque in the periodontal tissue, particularly grooves in the cervical part at the boundary between the teeth and gums. The gums become locally inflamed due to toxins and enzymes produced by these bacteria, resulting in gingivitis, and as this progresses gum pockets form where plaque accumulates, resulting in periodontitis. As the symptoms progress the pockets deepen and widen, inflammation spreads to and gradually destroys the roots of the teeth, which sooner or later fall out. Specifically, in the initial stages of periodontal disease the gums of the cervical part to which plaque has attached itself become red and swollen, losing their elasticity and bleeding during brushing. If this is ignored, the plaque gradually grows and forms calculus, spreading open the cervical area to form periodontal pockets. The calculus forms a barrier which prevents brushing of the underlying plaque, so that the bacteria gain force and their toxins cause the pockets to grow larger and larger, and the inflammation spreads from the gums to the periodontal ligament and alveolar bone, causing bleeding and pus with halitosis while at the same time the infection spreads one by one to the surrounding teeth. If inflammation of the pockets becomes chronic, the alveolar bone which supports the roots of the teeth begins to dissolve from the surface, accompanied by edema of the gums, the teeth wobble and feel loose because they are not properly supported, and strong halitosis occurs along with pain when the patient bites down hard. As the disease progresses most of the alveolar bone is lost, the roots of the teeth are exposed, the teeth become looser so that the patient can no longer eat hard foods, and finally the teeth fall out one by one. Consequently, experts recognize periodontal disease as a classic model of a chronic infectious disease that is still hard to cure.

Another problem concerns the drugs themselves: drugs are foreign to the body and produce side-effects to a greater or lesser degree, and experts point out that the more effective the drug, the greater the side-effects. In general it is said that the effects of drugs are halved while the side effects are doubled in the elderly—a fact that cannot be ignored considering the aging of society. The stronger and stronger demands for safety and security from society as a whole also cannot be ignored. Accidental deaths from side effects continue to occur. Antibiotics are no exception, in fact producing much stronger blood toxicity than other drugs including the allergic reaction called "penicillin shock" as well as leucopenia, anemia and the like, and the resulting loss of immune strength has been recognized at public institutions. Because antibiotics are so useful, however, this has not been much of a problem except in actual cases of severe illness or death.

Antibiotics have another side effect which is not immediately obvious: they attack the intestinal flora, which is sometimes called a vital organ, causing microbial substitution. That is, immune function is further depressed by the synergistic effect of blood toxicity combined with a decrease in beneficial intestinal bacteria that are highly sensitive to antibiotics, promoting chronic infections and leading to new viral diseases and other infections. In fact, the bacteria which cause typical chronic infections such as periodontal disease, sinusitis, hemorrhoids and the like are often antibiotic resistant, and side effects accumulate while the drug is ineffective. Even without resistance, the more an antibiotic is used, the greater the risk of mutation into resistant strains. On the individual level, continuous exposure to toxins from pathogenic bacteria can be fatal when combined with decreased immune function, while on a societal level resistant bacteria have crossed national boundaries to cause unanticipated harm throughout the world.

Looking at the United States and Europe, the idea of creating bodies which do not become sick rather than treating them when they become sick (preventive medicine) has been in force for over a decade, and one effective means for this when has been accepted because of its safety is "probiotics," which borrows the help of beneficial bacteria.

Research into *Lactobacillus* was started in France by Pasteur, the father of modern microbiology, leading to the "prolongation of life" theory of the Russian Metchinikoff and many subsequent clinical applications, but it still has not been put into true practical use. This is because the results of epidemiological studies have not matched the results of experimental research. Recently, however, advances in intestinal bacteriology have shown that *Lactobacillus* has the following important roles.

(1) Immune function normalization: Normalizes and enhances the immune function, which is indispensable for maintaining life (2) Intestinal cleansing: Balances the intestinal flora, suppresses proliferation of harmful bacteria, and suppresses abnormal fermentation and production of harmful bacteria in the intestines (3) Blood cleansing: cleanses the blood as an extension of the intestinal cleansing function (4) Promotion of food utilization: Promotes synthesis of vitamins and amino acids; aids absorption of nutrients through the intestinal walls (5) Prevention of infections by harmful bacteria: prevents proliferation and infection in the intestine even if harmful bacteria invade from the outside (6) Cell normalization: Promotes normalization of cell functions In Japan as well, as society ages and controlling health costs becomes a national concern, the importance of disease prevention is being recognized and society as a whole is becoming more concerned with health. As a result, the number of products containing *Lactobacillus* as an ingredient is rising steadily, and more and more so-called "functional yoghurt" products are being developed. However, the truth is that if these product are consumed intermittently, effects such as those mentioned in (1) through (6) above and other definite effects on disease will be few and far between, while actual effectiveness against infection would seem to be a fool's hope.

Under these circumstance, the inventors proposed that a lactic acid bacillus having unique properties which was isolated and selected by the inventors in May of 2000 be used against infections with the aim of resolving the ill effects of conventional antibiotics such as drug-resistant bacteria, drug allergies, side-effects and problems affecting ordinary bacterial flora, and submitted a patent application for a "New Lactic Acid Bacterium Effective on Infectious Disease and Lactobacillus Preparation Comprising Lactic Acid Bacterium as Main Ingredient" (Japanese Patent Application Laid-open No. 2001-333766).

This application relates to a lactic acid bacillus which is a *Lactobacillus casei* species that not only acts to inhibit the growth of pathogenic bacteria but also produces "novel bioactive substances" which have the property of weakening the toxicity of pathogenic bacteria, and to a *Lactobacillus* preparation for acute and chronic infections which has this bacterium as a main component. In detail, of the *Lactobacillus casei* collected from nature we selected only those strains producing a broad-spectrum antibiotic, and then screened for hemolytic and S-R mutations, with confirmation through animal testing, to determine whether or not that antibiotic weakened the toxicity of pathogenic bacteria, and finally three strains of *Lactobacillus casei* which met the criteria, FERM BP-6771, FERM BP-6772 and FERM BP-6773, were applied to infections. These were also given resistance to widely-used antibiotics so that they could be used in combination with those antibiotics. In cases of acute infections such as acute colitis, acute cystitis, acute bronchitis and the like, faster treatment effects were achieved through use of these *Lactobacilli* in conjunction with antibiotic administration than were achieved with conventional antibiotics alone, including (i) reduced antibiotic dosage, (ii) quicker amelioration of symptoms and faster recovery with fewer side-effects, and (iii) less disturbance of the intestinal flora, and the ill effects from the drug were reduced. However, the effects took time to appear and a complete cure was not achieved in the case of chronic infections such as gingivitis, sinusitis, bronchitis and hemorrhoids.

As discussed above, the issue is to grow a *Lactobacillus casei* capable of colonizing and multiplying in the lesions of a chronic infection that resists treatment, and of providing a strong cleansing action while eliminating the causal bacteria.

DISCLOSURE OF THE INVENTION

As a result of exhaustive research aimed at resolving the aforementioned issues, the inventors succeeded in achieving this goal from hints obtained by looking at the vaginal cleansing system, which maintains a clean environment even while being constantly exposed to bacterial contamination.

That is, this is a *Lactobacillus casei* species having the properties described in (1), (2), (3), (4) and (5) below, which is preferably the *Lactobacillus casei* species FERM BP-10059 (FERM P-19443):

(1) The species can be grown in the presence of any of one to four amino acids as a nitrogen source necessary for growth;

(2) When a growth-promoting culture medium is inoculated with the species and *Escherichia coli* in the same count and subjected to anaerobic mixed culturing at 37° C., the final count of lactobacilli is 50% or more of the coliform count;

(3) Upon cultivation in an appropriate culture medium, the final pH value is 4.0 or below, and the highest acidity is 1.5% or more;

(4) The species is resistant to 5% bile salts;

(5) The species produces an antibiotic.

Secondly, the present invention is a *Lactobacillus casei* species having at least one of the following properties in addition to the properties listed above, and this *Lactobacillus casei* species is FERM BP-10059 (FERM P-19443):

(a) Has resistance to widely-used antibiotics;

(b) Has amylolytic ability;

(c) Promotes the growth of chlorella;

(d) Grows at temperatures in the range of 5° C. to 45° C.;

(e) Grows at pH values in the range of pH 4.0 to pH 10.0;

*Lactobacillus casei* species (strain) FERM BP-10059 (FERM P-19443) was deposited on Jul. 22, 2003, in the International Patent Organism Depositary, National Institute for Advanced Industrial Science and Technology, AIST Tsukuba Central 6, 1-1, Higashi 1-chome, Tsukuba-shi, Ibaraki-ken, 305-8566, JAPAN.

(f) Can also grow under any oxygen pressure.

Thirdly, the present invention is a living body activating lactobacillus preparation having the *Lactobacillus casei* species described above as a primary active ingredient, wherein the aforementioned *Lactobacillus casei* species is FERM BP-10059 (FERM P-19443).

Fourthly, the present invention is a preventative or therapeutic agent for living body infection having the *Lactobacillus casei* species described above as a main primary ingredient, which preferably contains an antibiotic, and which is preferably applied to an affected area in the treatment of periodontal disease after the affected area is already disinfected with a bactericidal disinfectant, wherein said bactericidal disinfectant preferably contains 500 to 1,500 ppm of ferric ions, 500 to 2,000 ppm of L-ascorbic acid and 200 to 2,000 ppm of one or at least two of sorbic acid, benzoic acid and paraoxybenzoic acid ester as principal components, and said *Lactobacillus casei* species is preferably FERM BP-10059 (FERM P-19443).

At present, society as a whole values safety and security over all else, and in health and medicine the concept of "probiotics" has taken center stage in the West in particular. "Probiotics" refers to the use of bacteria and other microorganisms which are symbiotic organisms that live in the intestines and are beneficial to the body, and to methods of aggressively preventing and treating disease using such bacteria, especially the internal use of lactobacilli including *Lactobacillus bifidus* and the like.

The inventors in this case quickly made use of this to develop the lactobacillus preparation of the present invention, which consists of a *Lactobacillus casei* species that has been given unique properties. At the cutting edge of probiotics, this preparation not only has very clear effects in restoring, maintaining and promoting health, but has also succeeded in providing therapeutic effects not provided by conventional products of the same type with respect to chronic cases of infection that are difficult to treat even by modern medicine. Moreover, because the lactobacillus of the present invention is resistant to antibiotics, more rapid treatment can be achieved in combination with antibiotics. In this case, the minimum dosage of antibiotic is sufficient, and the various intrinsic ill effects of the drug such as side effects and spreading of drug-resistant bacteria can be reduced. In addition, in the context of increases in the degenerative diseases of an aging society and increases in chronic infections due to aging, along with the inevitable increase in medical costs, the role of the lactobacillus preparation of the present invention as a means of resolving these problems will be more and more important in the future.

Before the advent of antibiotics, very few efforts were made anywhere in the world to treat periodontal disease. The bacteria within the lesions of periodontal disease were also though to be a cause of heart disease and other fatal disease, and because of this perceived danger teeth with bad cavities or periodontal disease were pulled without hesitation. Because of this theory dentistry long consisted not of treatment for disease but of tooth pulling and dealing with the effects of tooth pulling through dentures. This situation began to improve with the advent of antibiotics, and in the nineteen-eighties research into periodontal disease pathogens allowed the progress of the disease to be better understood. This led to fundamental therapy to remove plaque and calculus, with the result that inflammation subsided, periodontal pockets became shallower, loose teeth were aligned and no longer wobbled, and when this was not successful surgery was done on the gums. In this way, therapeutic strategies were developed to preserve the teeth. On the other hand, the intractability of periodontal disease was re-evaluated when it was found that bacteria hidden inside the gums form special collective structures and barriers, reducing the pharmaceutical effects of antibacterial and bactericidal drugs, and that patient lifestyle habits, systemic conditions and genetic factors are also involved in the occurrence and progress of the disease. Perhaps out of a sense of futility, there has been little progress in the past decade in the basic study and treatment of periodontal disease.

With the arrival of a long-lived society, experts have gradually disclosed a close association between the teeth and physical health, realizing that the teeth serve not only a chewing function but also are central to life itself, and society has come to realize that to prevent dementia, cancer, stroke, heart disease and the like it is important to treat teeth in order to bring out the body's natural healing powers and enhance systemic functions. That is, it was realized that the teeth are irreplaceable organs, and that by means of the teeth it is possible to improve physical and psychological functions, prevent aging and improve human happiness. Tooth loss and cavities and the implantation of imperfect artificial teeth to replace them may lead to continuous and cumulative stress reactions in the living body. With the current focus on side effects and drug problems, the development of the safe preventative agent and therapeutic agent of the present invention, which places little physical, psychological or financial burden on either doctor or patient, holds great promise for revolutionizing the treatment of periodontal disease, which is often derided as "mop-up" treatment, and is bound to be good news for the human race as we aim for society in which it is natural to keep one's teeth.

In place of the disinfectants and antibiotics which have been widely used in the treatment process, the lactobacillus preparation of the present invention, which has unique properties and high affinity for mucous membranes, in combination with a bactericidal disinfectant (U.S. Pat. No. 6,296, 881B1) developed by the inventors which is gentle to mucous membranes but has severe effects on pathogenic bacteria, is an excellent preventative agent and therapeutic agent for periodontal disease, capable of effecting an almost complete cure in cases of periodontal disease from the early stages to the late stages regardless of the technical abilities of the dentist as long as there is alveolar bone left to support the teeth. Moreover, the therapeutic agent for periodontal disease of the present invention can be administered in addition to conventional treatments for periodontal disease.

Moreover, animal growth can be promoted by the administration of the lactobacillus preparation of the present invention during the rearing of pigs, chickens, mackerel, insects and other animals, contributing to improved quality and disease prevention, and it exhibits strong therapeutic effects against a variety of diseases including Saproglenia infection and ulcer disease in goldfish.

Moreover, growth can be promoted and higher quality obtained by applying the lactobacillus preparation of the present invention to plants including strawberries, spinach and other vegetables and herbs. In addition to preventing disease occurrence it is also effective in treating plant diseases such as powdery mildew and downy mildew in cucumbers.

The appearance of the lactobacillus preparation of the present invention breaths fresh air into the conventional fixed concept of treating infections with antibiotics or agricultural chemicals, and is bound to contribute greatly to the future recognition and development of "probiotics".

Lactobacilli are widely present in nature, from the intestines, oral cavity and other parts of the living body to tree leaves, grass, crops, fruits, soil and sewage, and are found abundantly in all places of living activity. As a result, they have been used as a matter of course in food processing and preservation since ancient times when people were not even aware of their existence, while nowadays the role of lactobacilli is appreciated from a scientific perspective and they have gained attention as probiotics.

The inventors have gone one step further to develop a lactobacillus having high affinity for the living body and excellent cleansing abilities that were not heretofore available. We have shown that this bacterium is not only effective in preventing and treating disease, but also contributes greatly to improving the growth and quality of animals and plants. Hence, its industrial applicability is thought to extend not only to primary industry but also to the health industry as a whole in the general sense and to the cosmetic industry as an extension of the health industry, and it can be used and applied widely in the food industry or generally in all environments required for human life.

BEST MODE FOR CARRYING OUT THE INVENTION

Figure 1:
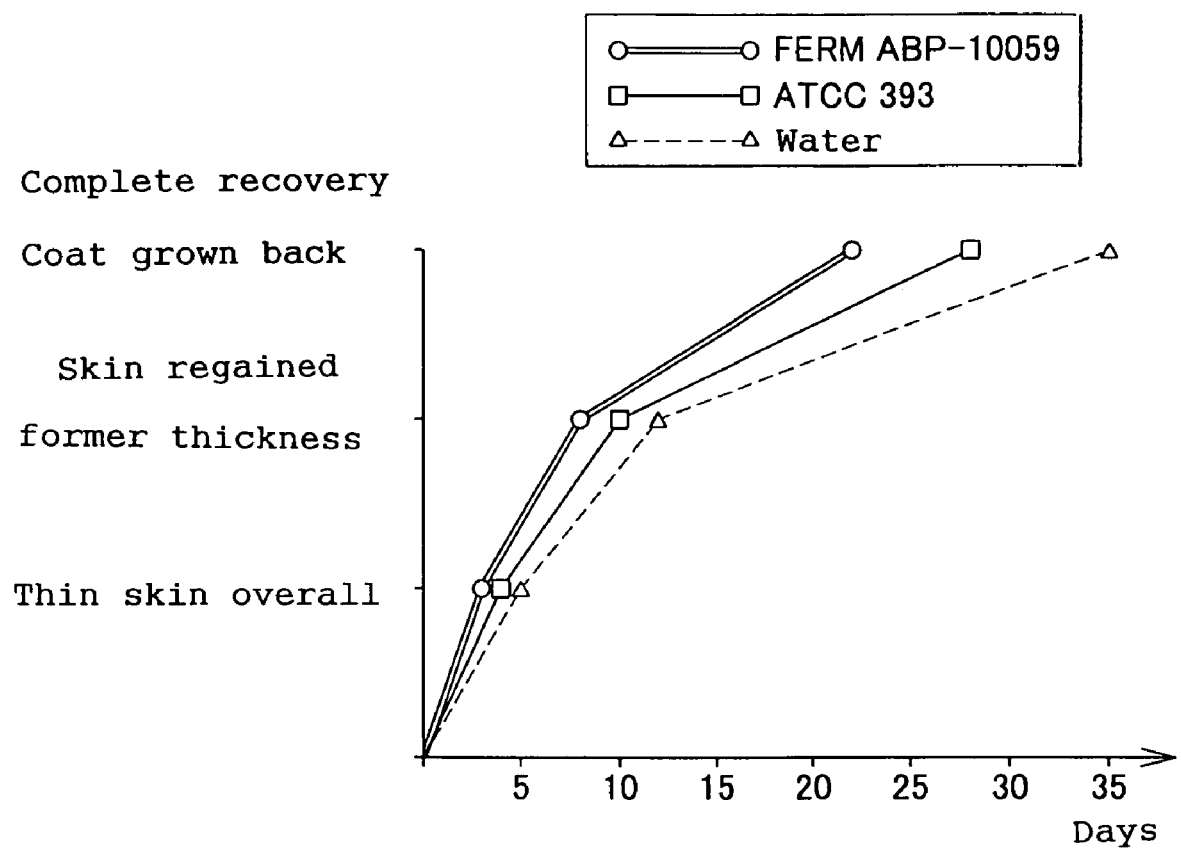
FIG. 1 shows regeneration of mouse skin after detachment.

The *Lactobacillus casei* species of the present invention may be in the form of cell bodies obtained by culture, a culture liquid or a decontaminated culture filtrate, while the preparation containing a novel *Lactobacillus casei* may be a preparation containing only the *Lactobacillus casei* of the present invention or a preparation containing the *Lactobacillus casei* of the present invention along with an antibiotic.

The *Lactobacillus casei* species of the present invention was developed with reference to the existence of lactobacilli normally present in the vagina. That is, Doederlein's bacillus, which is normally present in the vagina, breaks down the glycogens exuding from the vaginal wall, producing lactic acid which maintains acidity and prevents the proliferation of putrefactive bacteria invading from the outside, and thus plays a vital role in maintaining cleanliness. This bacterium is very similar to *Lactobacillus acidophilus*, and when its growth is suppressed by antibiotics or the like yeasts and other bacteria are known to proliferate and may cause various inflammations. That is, an infection-prevention system is constructed the mainstay of which is a *lactobacillus* which can establish itself and proliferate with a small amount of nutrition in the vagina. This cleansing system seems to be a basic and common one considering that intractable hemorrhoids clear up naturally if the intestinal flora comes to consist mainly of beneficial bacteria.

Based on these findings, the inventors perfected the present invention by collecting as many lactobacillus digestive aids and commercial lactobacillus products as possible and studying the strains in them, when they discovered that only those bacterial strains meeting certain conditions had 100% of their original overt or latent abilities and could fundamentally activate the living bodies of animals and plants, with economic effects on their growth and quality, as well as increasing the immune system (natural healing ability) against disease while at the same time strongly excluding causal bacteria in cases of infection.

Of the conditions to be met by the *Lactobacillus casei* of the present invention, the first essential condition is that (1) the nutrient demand be much less than that of known conventional *Lactobacillus casei*. That is, this means that the species can be grown in the presence of any of one, two, three or four amino acids as a nutrient nitrogen source. (2) proliferation is rapid in the growth environment. This means that when a growth-promoting culture medium is inoculated with the species and *Escherichia coli* in the same amount and subjected to anaerobic mixed culture at 37° C., the final count of lactobacilli is 50% or more of the coliform count. (3) Lactic acid production ability is high. This means that upon cultivation in an appropriate culture medium, the final pH value is 4.0 or below, and the highest acidity is 1.5% or more. (4) The species has high resistance to bile acids. This means that the species is resistant to 5% bile salts. (5) The species produces an antibiotic and can inhibit the proliferation of other bacteria.

More preferably, the species (a) has resistance to widely-used antibiotics; (b) has amylolytic ability; (c) promotes the growth of chlorella; (d) has a wide range of growth temperatures (grows at temperatures in the range of 5° C. to 45° C.); (e) has a wide range of growth pH values (grows at pH values in the range of pH 4.0 to pH 10.0); and (f) has a wide range of oxygen pressure at which it can grow (that is, it can grow under any oxygen pressure).

Therefore, the inventors acclimated the *Lactobacillus casei* species FERM BP-6971, FERM BP 6972 and FERM BP-6973 (hereunder, "original *Lactobacillus casei* species), for which a patent application has already been submitted, and after much effort dedicated to conferring the aforementioned properties, succeeded in producing a bacterial strain meeting the conditions of the present invention from FERM BP-6971 by the process described below.

To have an effect on a living body, a bacterium must adapt to its environment, prevail in growth competition with pathogenic bacteria and adequately reproduce itself. A necessary condition for this is the production of an antibiotic which suppresses the growth of other bacteria, and before that the basic potential or in other words the proliferative potency of the bacteria must be strong. In general lactobacilli have high nutrient demands, and for example the MRS medium widely used for bacterial growth is composed of 10 g of meat extract, 5 g of yeast extract, 10 g of peptone, 0.2 g of $MgSO_4 \cdot 7H_2O$, 0.5 g of $MnSO_4 \cdot 5H_2O$, 5 g of sodium acetate, 2 g of diammonium citrate, 2 g of $KH_2PO_4$ and 20 g of glucose per liter. The *Lactobacillus casei* of the present invention is not an exception, but since it is a *Lactobacillus casei* isolated from nature its original nutrient demands are moderate, and it can proliferate with appropriate concentrations of amino acids, vitamins, usable sugars and inorganic salts, such as for example a medium consisting of S-W medium plus 1 g casamino acids and 0.1 g vitamins. S-W medium itself contains 1 g of $KH_2PO_4$, 0.7 g of $MgSO_4 \cdot 7H_2O$, 1 g of NaCl, 4 g of $(NH_4)_2HPO_4$, 0.03 g of $FeSO_4 \cdot 7H_2O$ and 5 g of glucose per liter. Plate medium was prepared with this composition, and the original *Lactobacillus casei* species dispersed in sterilized sodium chloride solution was applied thereto and cultured anaerobically for 48 to 72 hours at 37° C. The largest of the resulting colonies were selected, harvested, and cultured again by the same procedures as above, and the operation of selecting and harvesting the colonies as they grew was repeated to obtain the strain with the fastest growth and proliferation in this medium composition. Next, a strain with good growth was selected by repeating the same operation with ½ the nutrient concentration in the medium, after which colonies which grew in medium with the nutrient concentration gradually reduced to ¼, ⅛ and ¹⁄₁₆ were identified in order to obtain a strain with the ability to grow and to proliferate rapidly in environments of extremely low nutrition.

Conventional known *Lactobacillus casei* including the original *Lactobacillus casei* species require a variety of amino acids as nitrogen sources for growth, but the *Lactobacillus casei* species of the present invention can grow with any one amino acid or with 2, 3 or 4 amino acids as a nitrogen source. An example would be inorganic salts plus sugar plus vitamins plus L(+)-lysine hydrochloride plus L-glutamic acid. When grown together with *Escherichia coli*, a bacteria which like *Lactobacillus casei* is a familiar bacteria which grows everywhere in nature and which is known as an indicator species of environmental contamination, the *Lactobacillus casei* species of the present invention was not inferior to *Escherichia coli* in terms of extent and speed of growth in the initial and middle stages, and the final count of lactobacilli was 50% or more of the coliform count. When this ratio of the bacteria is 30% or less, a bacterial strain can have little effect on a living body however great its abilities.

Next, another important property needed to prevail in growth competition with other bacteria is the ability to suppress the growth of other bacteria in an environment of reduced pH. This means a bacterial strain with strong lactic acid production ability. In particular, lactic acid produced in the digestive system protects the body from the invasion and proliferation of various pathogenic bacteria from outside, and secondarily encourages peristalsis in the intestines, promoting the excretion of waste products from the intestines and suppressing the production of putrefaction products. It has been shown experimentally that a final pH of 4.0 or less and a maximum acidity of 1.5% or more is one important condition for increasing the functions of lactobacilli. However, in the case of most known *Lactobacillus casei* the final pH does not reach 4.2 or less and the highest acidity is less than 1.5%. One example of a rearing method for enhancing lactic acid productivity is to culture the bacteria anaerobically for 48 to 72 hours at 37° C. in an opaque medium consisting of 3 g of $CaCO_3$ added to the medium described above which contains 10 g of meat extract, 5 g of yeast extract, 10 g of peptone, 0.2 g of $MgSO_4.7H_2O$, 0.5 g of $MnSO_4.5H_2O$, 5 g of sodium acetate, 2 g of diammonium citrate, 2 g of $KH_2PO_4$ and 20 g of glucose per liter, linking the colonies, and repeatedly selecting those with the widest transparent rings around them. This makes use of the fact that when lactic acid is produced the opaque calcium carbonate binds to the lactic acid and changes to calcium lactate.

The digestive tract is connected to the outside via a single tube, and one reason why bacteria living in the harsh environment of the outside world do not establish themselves and proliferate in the nutrient-rich, gentle environment of the intestines has to do with the presence of bile acids secreted by the gall bladder. Consequently, most isolation and selection media for intestinal bacteria have bile acids added to the composition in order to suppress the growth of other bacteria. According to the inventors' findings, when the concentration of bile acids such as sodium deoxycholate reaches 0.1%, intestinal bacteria continue to grow but most bacteria which do not live in the intestines do not grow. The original *Lactobacillus casei* species was capable of growing up to a bile acid concentration of 0.2%, but the conclusion was reached partly for the following reasons that activity in the body required growth at a bile acid concentration of 0.5%. Consequently, a bacterial strain was reared by ordinary method for resistance to bile salts. That is, we began by adding 0.2% bile acids to high-nutrient medium such as the lactic acid selection medium LBS and proliferation medium MRS, and increased the bile acid concentration in stages to 0.5% as the bacteria grew. Once a resistant strain had been obtained it was shown to maintain its resistance regardless of the type of medium, and it was also shown for the first time in these experiments that bile acid resistance correlates with mucous membrane affinity. That is, as bile acid resistance increases or in other words as affinity for bile acids increases the bacteria become increasingly capable of colonizing mucous membranes outside the intestines, such as the oral cavity, nasal mucous membrane, vagina and the like.

The ability to produce antibiotics that impede the survival of other bacteria is also important. The original *Lactobacillus casei* produces a broad-spectrum antibiotic that not only impedes the growth of other bacteria but has also been reported to weaken the toxicity of pathogenic bacteria, and the *Lactobacillus casei* of the present invention retains this ability. Moreover, the *Lactobacillus casei* of the present invention needs to be resistant to widely used antibiotics, but the original *Lactobacillus casei* is antibiotic resistant, and the *Lactobacillus casei* of the present invention retains this ability.

The ability to use starches abundantly present throughout the natural world as energy sources is desirable for colonization, survival and proliferation in living bodies. However, most *Lactobacillus casei* are not amylolytic, or only weakly so. The original *Lactobacillus casei* species is no exception and lacks amylolytic ability, but through the process of acclimatization it was possible to confer high amylolytic ability without affecting the ability to break down glucose and lactose, resulting in the *Lactobacillus casei* of the present invention. One example of a rearing method for enhancing amylolytic ability is to add 4.5 g of glucose and 0.5 g of starch (starch 10% of sugars) to a medium- to low-nutrient medium with a pH of 7.4 consisting of 1 g of meat extract, 1 g of yeast extract, 3 g of peptone, 1 g of NaCl, 0.5 g of $K_2HPO_4$, 0.5 g of $MgSO_4.7H_2O$, 0.05 g of $MnSO_4.5H_2O$, 1 g of sodium acetate, 0.5 g of diammonium citrate and 12 ml of 0.2% BTB per liter, and then culture anaerobically for 48 hours at 37° C. Subculturing is then repeated in medium of the same composition, and if even a little amylolysis is confirmed the percentage of starch is then raised to 20%. In this way, the starch percentage of the sugars is raised to 100% as subculturing is repeated, and the ability to break down starch is rapidly acquired in the same way as for glucose. In any medium, the pH decreases as sugars are broken down to produce acids, and the color of the medium changes from blue to yellow. It is important to keep subculturing until the depth of yellow of the medium with starch added is the same as with 100% glucose. Fortunately, most bacteria that cause chronic infections are incapable of obtaining energy from the breakdown of starch, so giving the *Lactobacillus casei* species this ability is particularly effective as a measure against infections.

Chlorella is a single-celled plant with strong vitality that has continued to photosynthesize and produce generations through repeated cell division for more than a billion years on this planet, and is seen as the ancestor of a variety of living plants. That is, it can be said that chlorella is the original form and source of life on earth. If a lactobacillus promotes the growth and proliferation of chlorella, it means that the substances produced by this lactobacillus activate and having a restorative effect on living cells, so obviously they should also be effective for living bodies which are accumulations of cells. It has been known for decades that the metabolic products of chlorella promote the proliferation of lactobacilli, but it has heretofore not been reported that conversely, the metabolic products of lactobacilli stimulate the proliferation of chlorella. Consequently, as an example of a rearing method for increasing the ability to promote growth of chlorella, a medium with a pH of 6.8 consisting of 5 g peptone, 2 g meat extract, 5 g glucose, 5 g yeast extract, 2 g $KNO_3$, 2 g $K_2HPO_4$, 0.1 g $MgSO_4.7H_2O$, 0.1 g $CaCl_2.2H_2O$, 0.1 g NaCl, 0.01 g $MnSO_4.5H_2O$, 0.05 g $ZnSO_4.5H_2O$, 3 g $CaCO_3$ and 15 g agar per liter was sterilized under high pressure for 15 minutes at 120° C. and cooled to about 50° C. after sterilization, a suitable amount of pure-cultured chlorella was added and mixed uniformly, and the mixture was poured into Petri dishes. Following 48 to 72 hours of pre-culture in a lighted incubator at 28° C., the original *Lactobacillus casei* species dispersed in sterilized saline solution was applied to the medium and subcultured aerobically and anaerobically (a few % $CO_2$) at 28° C. to 32° C. with light. This was observed every 24 hours to determine whether chlorella around the proliferating colonies of *Lactobacillus casei* was proliferating more densely than in the other areas. Colonies exhibiting even the slightest such tendency were repeatedly harvested to prepare the *Lac-* tobacillus casei species of the present invention which promotes the growth of chlorella.

A wide range of possible oxygen pressures, temperatures and pH values for growth is also a desirable condition for adapting and competing successfully in harsh environments, and this can be achieved by an ordinary acclimatization method with the selection of an appropriate medium.

The differences among known, conventional *Lactobacillus casei*, the original *Lactobacillus casei* species and the *Lactobacillus casei* species of the present invention are shown in Table 1. As shown in Table 1, because the *Lactobacillus casei* species of the present invention which was screened by selection and acclimatization has unique properties not present in known *Lactobacillus casei* or in the original *Lactobacillus casei* species, when used in a living body the *Lactobacillus casei* species of the present invention may not only provide dramatic effects not obtained from the various lactic acid products jostling each other on food shelves and health food shelves, but may act quite clearly to restore, maintain and increase health and to produce economic effects such as quality improvement and the like when used in plants and animals, and may be quite effective against infections. The lactobacillus preparation of the present invention can thus be called a living body activating lactobacillus preparation or a preventative or therapeutic agent against infection in animals and plants.

TABLE 1

Comparison of properties of different species of *Lactobacillus casei*

| | Known *Lactobacillus casei* | Original *Lactobacillus casei* species | *Lactobacillus casei* species of invention |
|---|---|---|---|
| Nutrient demand | Moderate-High | Moderate | Low |
| Amino acid requirements | Requires several amino acids | Requires several amino acids | Requires only 1 to 4 amino acids |
| Growth in normal agar medium | − to ± | + | ++ |
| Growth rate | Slow | Moderate | Fast |
| Lactic acid productivity | + | ++ | +++ |
| Final pH | 4.2< | 4.2< | 4.0> |
| Acidity | 1.2%> | 1.2%> | 1.5%< |
| Bile acid resistance (ability to colonize mucous membranes) | About 0.1% (low) | 0.2% (moderate) | 0.5% (high) |
| Antibiotic productivity (toxicity-weakening) | − to + (−) | + (+) | + (+) |
| Resistance to known antibiotics | − | + | + |
| Amylolysis | − | − | ++ |
| Effects on growth of chlorella | Not involved | Not involved | Promotes growth |
| Allowable oxygen range for growth | Slightly aerobic to anaerobic, growth poor in aerobic environments | Slightly aerobic to anaerobic, growth poor in aerobic environments | Aerobic to anaerobic, grows well in all environments |
| Temperature range for growth | 15 to 43° C. | 15 to 43° C. | 5 to 45° C. |
| pH range for growth | 5.0 to 7.5 | 4.5 to 9.5 | 4.0 to 10.0 |
| Intestinal colonization ability | − to ± | ++ | +++ |
| Intestinal regulatory effects | − to ± | + | ++ |
| Behavior towards pathogenic bacteria | Weakly growth-suppressing | Strongly growth-suppressing | Extremely strong growth-preventing ability |

The plaque which is the cause of periodontal disease is said to be an accumulation of about 400 types of bacteria, of which the most pathogenic for periodontal disease have been shown to be *Poryphyromonas gingivalis*, *Prevotella intermedia* and *Actinobacillus actinomycetemcomitans*, with *Walinella recta*, *Bacteroides forsythus*, *Eikenella corrodens*, *Fusobacteria*, *Treponema* and the like being involved as accessories. The specificity of the periodontal disease is the biggest factor that makes it hard to cure this disease. Because the teeth are directly connected to the inside of the body, when an inflammatory reaction is severe the body does not try to heal the periodontal disease but instead forms deep grooves at the boundaries between the teeth and gums, destroying the tissue supporting the teeth and sacrificing the teeth to protect the body like a lizard which lives with its tail cut off. In other words, it is not an external enemy that destroys the tissue supporting the teeth but the inflammation itself, which is a means of protecting the body from the external enemy. Tooth roots which have been contaminated and penetrated by bacterial toxins and enzymes are not recognized as self by the body, which acts to exclude them as causative factors together with surrounding tissue. That is, a curative reaction actually exacerbates the periodontal disease. Consequently, once all the teeth affected with periodontal disease fall out, the disease clears up completely.

Other factors include (1) the fact that the oral cavity is a suitable environment for the growth and proliferation of bacteria, and is difficult to keep clean, and bacteria with strong periodontal pathogenicity in particular adhere strongly to the teeth and gums by producing sticky glucans, fructans and other insoluble polysaccharides, substances which also serve as a barrier to protect the periodontal pathogens, (2) the fact that since the toxins and enzymes which they produce penetrate inconspicuously into periodontal tissue, the disease progresses with few subjective symptoms, and the appearance of symptoms is not uniform but involves a variety of factors including soiling around the teeth, inflammation, gum retraction, aging and the like, while once gum pockets have formed they generally do not close which in combination with (1) above leads to repeated re-occurrence, (3) the fact that few dentists undertake therapy using appropriate drugs in cooperation with specialists in bacteriology, (4) the fact that both doctors and patients assume that in the worst case the teeth can be pulled, and (5) the fact that periodontal disease is not a local problem but a systemic disease often involving for example diabetes and other endocrine disorders, genetic disorders, stress, osteoporosis, circulatory disorders and the like, and cannot be completely cured simply by symptomatic therapy. Periodontal disease involves many detrimental factors, and is considered incurable unless treatment is started in the early stages.

At present, the primary form of early therapy is treatment such as scaling and root planning to remove the plaque and calculus, which are hotbeds of periodontal disease. Supragingival calculus adhering to the surfaces of teeth above the gum line is relatively easy to remove, but subgingival calculus adhering to the surfaces (roots) of teeth below the gum line is dense and hard, blackish-green in color and strongly adhesive, and the bacteria and their toxins cannot be easily removed simply by brushing. Consequently, methods have recently been adopted of destroying it efficiently with ultrasound or lasers or dissolving it with special chemicals. After that, a disinfectant or antibiotic is injected and fixed in the periodontal pocket until the inflammation clears up. However, when the site of inflammation is deep and the aforementioned therapy does not produce favorable results, the site of inflammation or damage is removed by surgery. Subsequently, the gums are sewn up or reconstructed with artificial material. More recent techniques include surgery according to GTR (guided tissue regeneration) methods and application of a type of protein called Emdogain as an adjunct to surgery to recreate an environment similar to the tooth regeneration process and encourage the regeneration of periodontal tissue, but these are not effective against all advanced cases of periodontal disease, and their application is limited. In any case, at present basic treatment for periodontal disease is aimed at controlling inflammation of the gums, arresting the progress of the periodontal disease, regenerating lost periodontal tissue, improving external appearance and maintained newly regained tissue, but as mentioned above periodontal disease also involves systemic risk factors, and unfortunately at present there is no therapy which is effective enough to be a favorite, and many dentists are content if they can keep the situation from getting worse.

The bactericidal disinfectant discussed in the present invention (hereunder, "this bactericidal disinfectant) is a bactericidal disinfectant containing 500 ppm to 1,500 ppm of ferric ions, 500 ppm to 2,000 ppm of L-ascorbic acid and 200 ppm to 2,000 ppm of one or two of sorbic acid, benzoic acid and paraoxybenzoic acid ester as principal components. It has already been granted a U.S. patent (U.S. Pat. No. 6,296,881B1), and its components are recognized in Japan as food additives. At present, the disinfectants widely used by medical institutions include alcohols, phenols, halogen compounds, quaternary ammonium salts, biguanide compounds, aldehydes and the like, but none meets all the conditions of excellent bactericidal action, safety and low toxicity, excellent maintainability and cheapness. For example, the biguanide compound having the trade name "Hibitane" is an excellent disinfectant whose low toxicity and high effectiveness have made it a best seller worldwide for decades, but it has little effect on fungi and no effect on tubercular bacilli and spores. Some common bacteria have also developed resistance, and are a cause of hospital infections. On the other hand, "this bactericidal disinfectant," which was developed to fill in the gaps of conventional treatment, kills most bacteria and fungi in only 10 seconds, and is capable of destroying even spores in 1 to 120 minutes. Despite its excellent bactericidal properties, however, its toxicity is lower than that of any other existing disinfectant as shown below.

(1) Effects on skin: No abnormalities appeared from application to the rear feet (foot pads) of mice twice a day for 6 months.

(2) Effects of oral administration: 1 ml/mouse was administered but no toxicity was seen. This dose corresponds to 1.8 L for a human. The estimated $LD_{50}$ is 10 ml/mouse, which corresponds to 18 L for a human.

(3) Effects of intraperitoneal administration: The $LD_{50}$ is about 1 ml/mouse (4) Effects on cultured (animal) cells: A $10^3\times$ dilution of the concentration for use did not inhibit cell proliferation. This is about 1/10 the toxicity of Habitant.

(5) Effects on humans:

a) Hand and finger disinfection: No abnormalities were observed even after 7 years of daily use, apart from a slight reddening of the skin.

b) Gargling: No abnormalities of the mucous membranes were observed after 7 years of gargling every morning and night, and no side-effects or toxicity appeared. In addition, no cavities occurred during that period and it was not necessary to consult a dentist.

The following are the results of various tests of "this bactericidal disinfectant" in connection with periodontal disease.

"This bactericidal disinfectant" was prepared by preparing an aqueous solution of 3,000 ppm of ferric chloride hexahydrate ($FeCl_3.6H_2O$) as $Fe^{3+}$, an aqueous solution of L-ascorbic acid with a concentration of 3,000 ppm and an aqueous solution of potassium sorbate with a concentration of 1,500 ppm, and mixing equal amounts of these aqueous solutions.

TEST EXAMPLE 1

A suspension ($1\times10^9$ cells/ml saline solution) of the test bacterium was prepared, and 2% by weight of "this bactericidal disinfectant" was dripped into this cell liquid. Cells were harvested over time with one platinum loop, seeded on bacterial growth medium and cultured in an optimal environment, and the bactericidal effects were observed according to the presence or absence of bacterial proliferation. The bactericidal disinfectant used in the test was set to the commonly used concentration. The results after 10 to 60 seconds of contact and the results after 1 to 120 minutes of contact are shown in Table 2. As is clear from Table 2, "this bactericidal disinfectant" killed most bacterial species in their active forms within about 10 seconds. The strong periodontal pathogens *P. gingivalis, P. intermedia* and *A. actimomycetemconitans* were no exception. However, it took from 1 to 120 minutes to kill spores of sporulating bacteria depending on the stage of formation. According to statistics, the time taken for hand washing and gargling by medical workers and others is from 10 to 15 seconds, and in this context "this bactericidal disinfectant" is highly effective. When the same test was performed using the biguanide compound Habitant, 3% hydrogen peroxide solution and Acrinol, which are disinfectants widely used in hospitals and dentists' offices, 30 to 60 seconds was required, and as mentioned before Habitant was ineffective against *Mycobacterium and spores, while the* 3% hydrogen peroxide solution was also ineffective against spores and took 1 minute or more to kill *Mycobacterium. The results for acrinol were similar to those for the* 3% hydrogen peroxide solution.

TABLE 2

Bactericidal effects of bactericidal disinfectant

|  | Bactericidal effect (presence or absence of bacterial growth) Contact time | | | | | | | |
| --- | --- | --- | --- | --- | --- | --- | --- | --- |
|  | Seconds | | | | Minutes | | | |
|  | 10 | 20 | 30 | 60 | 1 | 30 | 60 | 120 |
| GRAM-POSITIVE BACTERIA | | | | | | | | |
| *Staphylococcus Aureus* | − | − | − | − | | | | |
| *S. Aureus* (MRSA) | − | − | − | − | | | | |

TABLE 2-continued

Bactericidal effects of bactericidal disinfectant

| | Bactericidal effect (presence or absence of bacterial growth) Contact time | | | | | | | |
|---|---|---|---|---|---|---|---|---|
| | Seconds | | | | Minutes | | | |
| | 10 | 20 | 30 | 60 | 1 | 30 | 60 | 120 |
| S. pyogenes (group A beta-hemolytic streptococcus) | − | − | − | − | | | | |
| S. pneumoniae | − | − | − | − | | | | |
| Enterococcus faecalis | + | + | − | − | | | | |
| Corynebacterium diphtheriae | − | − | − | − | | | | |
| Listeria monocytogenes | − | − | − | − | | | | |
| GRAM-NEGATIVE BACTERIA | | | | | | | | |
| Neiseria gonorrhoeae | − | − | − | − | | | | |
| Escherichia coli O-157 | − | − | − | − | | | | |
| Salmonella enteritidis | − | − | − | − | | | | |
| Shigella flexneri | − | − | − | − | | | | |
| Vibrio parahaemoliticus | − | − | − | − | | | | |
| Pseudomonas aeruginosa | + | − | − | − | | | | |
| Serratia marcescens | − | − | − | − | | | | |
| Klebsiella pneumoniae | − | − | − | − | | | | |
| Legionella pneumophila | − | − | − | − | | | | |
| P. gingivalis, A. actinomycetem (periodontal disease pathogens) | − | − | − | − | | | | |
| P. intermedia (periodontal disease pathogen) | − | − | − | − | | | | |
| MYCOBACTERIUM | | | | | | | | |
| Mycobacterium tuberculosis (human tuberculosis bacterium) | + | + | − | − | | | | |
| M. kansasii (atypical group I) | + | + | − | − | | | | |
| M. abium (atypical group III) | + | + | − | − | | | | |
| SPORULATING BACTERIA | | | | | | | | |
| Bacillus subtilis | | | | | | | | |
| Vegetative | − | − | − | − | | | | |
| Spores | | | | | + | to | − | |
| B. natto | | | | | | | | |
| Vegetative | + | + | + | − | | | | |
| Spores | | | | | + | to | − | |
| Clostridium perfringens | | | | | | | | |
| Vegetative | + | + | + | − | | | | |
| Spores | | | | | + | to | − | |
| C. tetani | | | | | | | | |
| Vegetative | + | + | + | − | | | | |
| Spores | | | | | + | to | − | |
| FUNGI | | | | | | | | |
| Candida albicans | + | − | − | − | | | | |
| Trichophyton interdigitale (athlete's foot fungus) | − | − | − | − | | | | |
| Aspergillus fumigatus | − | − | − | − | | | | |
| Cryptococcus neobormans | − | − | − | − | | | | |

TEST EXAMPLE 2

In general, it is known that the effects of disinfectants are reduced by contamination with organic matter, particularly proteins, so the bactericidal effects in the presence of organic matter were investigated. First, skim milk and yeast extract were each added to "this bactericidal disinfectant" in amounts of 1 ppm, 50 ppm and 100 ppm, while at the same time 2% by weight of a $1\times10^9$ cells/ml physiological saline solution of MRSA or E. coli O-157 as the test bacterium was dripped into these aqueous solutions. The contact time between the test bacterium and "this bactericidal disinfectant" was 10 seconds to 5 minutes, and 10 μl samples of the mixed test bacterium liquid were collected over time, seeded in appropriate medium and cultured at 37° C. to evaluate the bactericidal effects according to the presence or absence of bacterial growth. The results are as shown in Table 3. The presence of organic matter had no effect when the concentration of organic matter was 1 ppm, but when the concentration of organic matter was 50 ppm or more it had a slight effect. The same test was also performed with bacterial species other than the two mentioned above, with similar results. The same test was also performed using disinfectants commonly used in dentists' offices, but at concentrations over 50 ppm the bacteria did not die after 1 minute of contact with Habitant, and survived 5 minutes of contact in some cases depending on the type and amount of organic matter. The results obtained with the 3% hydrogen peroxide solution and acrinol were similar to those for Habitant.

TABLE 3

Bactericidal effects in the presence of organic matter

| | Bactericidal effect (Presence or absence of bacterial growth) Contact time | | | | | | |
|---|---|---|---|---|---|---|---|
| | 10 | 20 | 30 | 60 secs | 2 min | 3 min | 5 min |
| S. aureus (MRSA) Skim milk | | | | | | | |
| 1 ppm | − | − | − | − | − | − | − |
| 50 ppm | + | + | − | − | − | − | − |
| 100 ppm | + | + | − | − | − | − | − |
| Yeast extract | | | | | | | |
| 1 ppm | − | − | − | − | − | − | − |
| 50 ppm | + | − | − | − | − | − | − |
| 100 ppm | + | + | − | − | − | − | − |
| E. coli O-157 Skim milk | | | | | | | |
| 1 ppm | − | − | − | − | − | − | − |
| 50 ppm | + | + | − | − | − | − | − |
| 100 ppm | + | + | − | − | − | − | − |
| Yeast extract | | | | | | | |
| 1 ppm | − | − | − | − | − | − | − |
| 50 ppm | + | − | − | − | − | − | − |
| 100 ppm | + | + | + | − | − | − | − |

TEST EXAMPLE 3

We investigated whether in the putrefaction process after food preparation, spraying "this bactericidal disinfectant" on food would stop the progress of putrefaction, and what would be the degree of that bactericidal effect. Normally disinfectants are not applied to food after preparation, but often scraps of food work their way into periodontal pockets, providing a source of nutrition for bacteria, and since the ingredients in "this bactericidal disinfectant" are compounds which are recognized as food additives, it is important to assess these effects. "Cooked rice", "tofu", "spinach with sesame", and "fried meat and vegetables" immediately after preparation were crushed as the samples, homogenized, and left at 28° C. After 5 hours, part of each sample was taken for counting live bacteria, while the rest of each sample was sprayed thoroughly with the disinfectant. Live cells were counted 1 hour, 2 hours and 24 hours after spraying. Water alone was sprayed as a control. After each of the samples had been left for 24 hours, part was taken for counting live cells while the remainder of each sample was sprayed thoroughly with each disinfectant. As when the samples were left for 5 hours, live cells were counted 1 hour, 2 hours and 24 hours after spraying. Water alone was sprayed as a control. Live cells were counted by the poured plate method using 5 g of each sample, which was taken and diluted by ordinary methods.

The degree of putrefaction naturally differs according to the method of preparation, food material and environment. In the case of these samples, the live cell count in the cooked rice was $2\times10$ cells/g of sample immediately after preparation, $1\times10^3$ cell/g of sample after 5 hours, $5\times10^5$ cell/g of sample after 24 hours, and $7\times10^6$ cell/g of sample after 48 hours. In the case of the tofu the initial live cell count was $2\times10^4$ cells/g of sample, but this rose to $8\times10^5$ cells/g of sample after 5 hours, $9\times10^7$ cells/g of sample after 24 hours and $1\times10^9$ cells/g of sample after 48 hours, with a higher level of putrefaction. In the case of the spinach with sesame, the count was $2\times10^3$ cells/g of sample immediately after preparation, rising to $5\times10^4$ cells/g of sample after 5 hours, $3\times10^7$ cells/g of sample after 24 hours and $2\times10^8$ cells/g of sample after 48 hours. In the case of the fried meat and vegetables, the count was $5\times10$ cells/g of sample immediately after preparation, rising to $2\times10^3$ cells/g of sample after 5 hours, $2\times10^8$ cells/g of sample after 24 hours, at which point there was a slight smell of putrefaction, and $3\times10^9$ cell/g of sample after 48 hours, by which point putrefaction had progressed to a higher level.

The test results are shown in Table 4. Five hours after preparation when bacteria had not proliferated very much, spraying of disinfectant immediately reduced cell counts to $1/100$ to $1/200$, with some differences depending on the type of prepared food. After 1 hour this had dropped to $1/1000$ to $1/5000$ of the original count, and after 2 hours the cells had died out, with counts of 10 cells/g of sample or less. The surviving bacteria did not proliferate even after 24 hours. In meat and other protein-rich foods, $7\times10^2$ cells/g of sample (about 1%) survived 2 hours after spraying of disinfectant. 24 hours after preparation the cell counts were on the order of $10^7$ to $10^8$, but these fell to $1/1000$ to $1/10,000$ immediately after spraying of disinfectant, to $1/10,000$ to $1/500,000$ after 1 hour and to $1/300,000$ to $1/2,000,000$ after 2 hours. The cell count at this point was about $10^2$ cells/g of sample. After 24 hours the cell count was slightly higher than after 2 hours, but this was thought to reflect not so much proliferation of surviving bacteria as bacteria precipitating from the air. Consequently, bactericide was generally achieved although complete eradication was not. That is, there is a bactericidal effect and a suppression effect on the growth of putrefying bacteria in food.

The same test was performed using disinfectants widely used in dentists' offices in addition to "this bactericidal disinfectant," with the results shown in Table 4. When Habitant was sprayed, the rate of decrease in cell counts immediately after spraying was less than that achieved with "this bactericidal disinfectant," although the tendency was the same. However, this effect weakened over time and the bacteria began to proliferate again. That is, although growth of putrefying bacteria in food was suppressed to a certain extent, there was not a true bactericidal effect. Moreover, most of the bacteria survived immediately after spraying of a 3% hydrogen peroxide solution, and after 24 hours the food was on the point of putrefaction.

TABLE 4

Disinfectant-induced increases and decreases in cell counts in prepared food

| Food | | Water | This bactericidal disinfectant | Hibitane solution | 3% $H_2O_2$ solution |
|---|---|---|---|---|---|
| COOKED RICE | | | | | |
| Immediately after prep | $2\times10$ | | | | |
| After 5 hours | $1\times10^3$ (spray) | | | | |
| | Immediately | $1\times10^3$ | $8\times10$ | $1\times10^2$ | $2\times10^2$ |
| | 1 hour | $2.2\times10^3$ | $5\times10$ | $5\times10$ | $1\times10^2$ |
| | 2 hours | $7\times10^3$ | 0 | $2\times10$ | $1.8\times10^2$ |
| | 24 hours | $6\times10^6$ | 0 | $5\times10$ | $5\times10^4$ |
| After 24 hours | $5\times10^5$ (spray) | | | | |
| | Immediately | $5.5\times10^5$ | $8\times10^3$ | $1\times10^4$ | $4\times10^4$ |
| | 1 hour | $1.2\times10^6$ | $5\times10^2$ | $7\times10^2$ | $9\times10^3$ |
| | 2 hours | $2\times10^6$ | $1\times10^2$ | $5\times10^2$ | $2\times10^4$ |
| | 24 hours | $1\times10^8$ | $1\times10^2$ | $4\times10^3$ | $8\times10^5$ |
| After 48 hours | $7\times10^6$ | | | | |
| Tofu | | | | | |
| Immediately after prep | $2\times10^4$ | | | | |
| After 5 hours | $8\times10^5$ (spray) | | | | |
| | Immediately | $1\times10^6$ | $3\times10^3$ | $8\times10^2$ | $5\times10^4$ |
| | 1 hour | $3\times10^6$ | $1\times10^2$ | $5\times10$ | $2\times10^3$ |
| | 2 hours | $5\times10^6$ | 5 | $4\times10$ | $3\times10^4$ |
| | 24 hours | $1\times10^8$ | 8 | $2\times10^2$ | $6\times10^6$ |
| After 24 hours | $9\times10^7$ (spray) | | | | |
| | Immediately | $9\times10^7$ | $6\times10^4$ | $5\times10^4$ | $7\times10^5$ |
| | 1 hour | $1.2\times10^8$ | $4\times10^2$ | $5\times10^2$ | $3\times10^4$ |
| | 2 hours | $2\times10^8$ | $3\times10$ | $2\times10^2$ | $5\times10^4$ |

TABLE 4-continued

Disinfectant-induced increases and decreases in cell counts in prepared food

| Food | | Water | This bactericidal disinfectant | Hibitane solution | 3% $H_2O_2$ solution |
|---|---|---|---|---|---|
| | 24 hours | $2 \times 10^9$ | $1 \times 10^2$ | $3 \times 10^3$ | $1 \times 10^8$ |
| After 48 hours | $1 \times 10^9$ | | | | |
| Spinach with sesame | | | | | |
| Immediately after prep | $2 \times 10^3$ | | | | |
| After 5 hours | $5 \times 10^4$ (spray) | | | | |
| | Immediately | $5 \times 10^4$ | $2 \times 10^2$ | $2 \times 10^2$ | $1 \times 10^3$ |
| | 1 hour | $9 \times 10^4$ | $5 \times 10$ | $4 \times 10$ | $4 \times 10^2$ |
| | 2 hours | $1.5 \times 10^5$ | 0 | $3 \times 10$ | $5 \times 10^2$ |
| | 24 hours | $5 \times 10^7$ | $7 \times 10$ | $6 \times 10^2$ | $1 \times 10^5$ |
| After 24 hours | $3 \times 10^7$ (spray) | | | | |
| | Immediately | $3 \times 10^7$ | $5 \times 10^3$ | $3 \times 10^4$ | $4 \times 10^4$ |
| | 1 hour | $4 \times 10^7$ | $8 \times 10$ | $2 \times 10^2$ | $5 \times 10^3$ |
| | 2 hours | $6 \times 10^7$ | $2 \times 10$ | $1 \times 10^2$ | $5 \times 10^3$ |
| | 24 hours | $4 \times 10^8$ | $1 \times 10^2$ | $8 \times 10^3$ | $7 \times 10^6$ |
| After 48 hours | $2 \times 10^8$ | | | | |
| Fried vegetables and meat | | | | | |
| Immediately after prep | $5 \times 10$ | | | | |
| After 5 hours | $2 \times 10^3$ (spray) | | | | |
| | Immediately | $2.5 \times 10^3$ | $1 \times 10^2$ | $2 \times 10^2$ | $5 \times 10^2$ |
| | 1 hour | $6 \times 10^3$ | $5 \times 10$ | $5 \times 10$ | $2 \times 10^2$ |
| | 2 hours | $1 \times 10^4$ | $2 \times 10$ | $3 \times 10$ | $4 \times 10^2$ |
| | 24 hours | $3 \times 10^8$ | $7 \times 10^2$ | $5 \times 10^3$ | $5 \times 10^6$ |
| After 24 hours | $2 \times 10^8$ (spray) | | | | |
| | Immediately | $2 \times 10^8$ | $1 \times 10^5$ | $7 \times 10^4$ | $6 \times 10^6$ |
| | 1 hour | $4 \times 10^8$ | $4 \times 10^2$ | $5 \times 10^2$ | $5 \times 10^4$ |
| | 2 hours | $6 \times 10^8$ | $1 \times 10^2$ | $2 \times 10^2$ | $1 \times 10^5$ |
| | 24 hours | $4 \times 10^9$ | $2 \times 10^3$ | $5 \times 10^4$ | $4 \times 10^8$ |
| After 48 hours | $4 \times 10^9$ | | | | |

The data for "this bactericidal disinfectant" in Test Examples 1 through 3 suggest the potential for a strong bactericidal effect against periodontal pathogens hidden in periodontal pockets. By contrast, the disinfectants widely used in dentistry are somewhat effective when the periodontal pathogens do not have a barrier, but when plaque or calculus forms and when there is a nutritional source such as organic matter or food residue, their effects are much less.

Based on the above test results, we tested the effectiveness of each bactericidal disinfectant using as the test material plaque, which is regarded as the root cause of periodontal disease.

TEST EXAMPLE 4

Plaque adhering to supragingival calculus was collected, sections cut to a thickness of 200 μm and powdered plaque ground to a grain size of 10 μm were soaked in 1 ml of "this bactericidal disinfectant," and the numbers of live cells contained therein were measured over time by ordinary methods. The results are as shown in Table 5. The live cell count of $4 \times 10^9$ cells contained in 20 mg of plaque sections was reduced by ¾ after 1 minute of immersion, falling to ⅕,₀₀₀ of the original cell count after 5 minutes, and after 10 minutes all of the bacteria had died. All of the bacteria in the powdered plaque were eliminated within 3 minutes. That is, it was shown that "this bactericidal disinfectant" breaks through the barrier, penetrating the inside of the plaque and having a bactericidal effect on bacteria therein. In the case of Habitant (Habitant gel), 3% hydrogen peroxide solution and acrinol, which are widely used in the dental field, the bacteria on the plaque surface were mainly eliminated within 3 minutes, but the bacteria inside the plaque endured even 60 minutes of immersion, with half of the cells surviving. This means that they could not definitively damage the plaque, which is an aggregation of bacteria. When the same test was performed using plaque adhering to subgingival calculus (dense and hard), all the bacteria were eliminated in about 15 minutes in the case of the plate-shaped plaque and within 3 minutes in the case of the powder. By contrast, when Habitant and the like were used the bacteria inside the plaque endured 60 minutes of immersion and continued to survive as described above.

TABLE 5

Changes induced by bactericidal disinfectant treatment in live cell counts in plaque

| | Live cell counts per 20 mg of plaque | | | | | | |
|---|---|---|---|---|---|---|---|
| | Pre-treatment cell count | After 1 min | After 3 min | After 5 min | After 10 min | After 15 min | After 30 min |
| Plate-shaped plaque | $4 \times 10^9$ | $1 \times 10^9$ | $5 \times 10^7$ | $8 \times 10^5$ | 0 | 0 | 0 |
| Powdered plaque | $4 \times 10^9$ | $2 \times 10^8$ | 0 | 0 | 0 | 0 | 0 |

Next, considering cases in which further organic matter adheres to or contaminates plaque adhering to calculus, we mixed 20 mg of plaque with 20 mg of yeast extract and performed a test by the methods described above. The results are as shown in Table 6. There was little effect from the organic matter, with the cell count falling to about 1/2,000 the original count after 5 minutes of immersion and all bacteria being eliminated after 10 minutes of immersion in the case of the plate-shaped plaque. In the case of the powdered plaque, all the bacteria were eliminated after 3 minutes of immersion. By contrast, with commonly-used disinfectants disinfection of the plaque surface took 10 minutes due to the presence of organic matter, and most of the internal bacteria survived. That is, it is shown that unless plaque is completely eliminated in treatment, although a temporary improvement may be seen the problem will reoccur repeatedly.

TABLE 6

Changes induced by bactericidal disinfectant treatment in live cell counts in plaque and organic matter

| | Live cell counts in 20 mg of plaque and 20 mg of yeast extract | | | | | | |
|---|---|---|---|---|---|---|---|
| | Pre-treatment cell count | After 1 min | After 3 min | After 5 min | After 10 min | After 15 min | After 30 min |
| Plate-shaped plaque | $3.5 \times 10^9$ | $1.5 \times 10^9$ | $1 \times 10^8$ | $2 \times 10^6$ | 0 | 0 | 0 |
| Powdered plaque | $3.5 \times 10^9$ | $4 \times 10^8$ | 0 | 0 | 0 | 0 | 0 |

As is clear from the various test results given in Test Examples 1 through 4 above, "this bactericidal disinfectant" inflicts severe damage on bacteria surviving in active form in various environments. The periodontal disease pathogens living in periodontal pockets and hiding in hard to remove plaque are no exception, and it was shown that injection of "this bactericidal disinfectant" in these cases destroys the bacteria within seconds to about 10 minutes, with some differences depending on the growth stage and type of plaque. Moreover, it should be mentioned that in animal tests and human experiments such as those described above, "this bactericidal disinfectant" was shown to have very little damaging effect on cells and tissue, and to promote tissue regeneration.

TEST EXAMPLE 5

About 1 cm$^2$ of mouse skin was peeled off and various bactericidal disinfectants at ordinary concentrations were applied to the wounds using absorbent cotton every morning and night. Water was applied as a control. The results are as shown in Table 7. In the case of the control mouse it took 5 days for a thin skin to be regenerated over the wound, 12 days for the skin to regain its original thickness, and 35 days for the coat to grow back, while with application of "this bactericidal disinfectant" it took 4 days for the wound to close, 10 days for the skin to regain its original thickness and only 30 days for the coat to grow back. These results match those obtained with iodine tincture, meaning that both "this bactericidal disinfectant" and iodine tincture promote tissue regeneration. By contrast, with application of Habitant gel, 3% hydrogen peroxide solution and acrinol, which are widely used in dentistry, it took 5 days for a thin skin to form, 12 to 15 days for the skin to regain its original thickness and 40 days for the coat to grow back. That is, these disinfectants act as poisons that suppress tissue regeneration.

TABLE 7

Bactericidal disinfectant-induced recovery of skin wounds

| | Recovery | | |
|---|---|---|---|
| | Thin skin overall | Skin close to original thickness | Complete recovery (coat regrown) |
| This bactericidal disinfectant | 4 days | 10 days | 30 days |
| Hibitane gel | 5 days | 12 days | 38 days |
| 3% $H_2O_2$ soln | 5 days | 15 days | 40 days |
| Acrinol | 5 days | 15 days | 40 days |
| Iodine tincture | 4 days | 10 days | 32 days |
| Water | 5 days | 12 days | 35 days |

TEST EXAMPLE 6

When dilutions of "this bactericidal disinfectant" were added to medium, as shown in Table 8, they stimulated growth of the lactic acid bacillus used in the present invention. It is well known that growth of lactobacilli is promoted by addition of acetic acid, but it is surprising that a bactericidal disinfectant with bactericidal action should have a growth-promoting effect even in dilution. However, as shown in Table 9, periodontal disease pathogens and other pathogenic bacteria are not affected in this way. This means that if "this bactericidal disinfectant" is first injected into a periodontal pocket which is then washed with water and filled with the novel *Lactobacillus casei* species (hereunder, "novel lactobacillus") of the present invention which has unique abilities as described below, growth of the "novel lactobacillus" will be stimulated, enhancing the therapeutic effects against periodontal disease. By contrast, when widely-used disinfectants were added to medium at different concentrations, bacterial growth was sometimes suppressed but never stimulated. Moreover, the principal component $Fe^{3+}$ of "this bactericidal disinfectant" is adsorbed by tooth surfaces and serves as a barrier to protect them against re-adhesion by periodontal pathogens. Because it has an astringent effect, moreover, secretion of periodontal groove fluid that provides a nutrient source for periodontal pathogens is temporarily reduced, thus suppressing growth and proliferation by cutting off part of the nutrient supply for periodontal pathogens hidden inside the grooves.

TABLE 8

Effect of this bactericidal disinfectant on growth of lactic acid bacilli

| | Normal concentration dilution of this bactericidal disinfectant contained in medium | | | | | | |
|---|---|---|---|---|---|---|---|
| | 1/10 | 1/30 | 1/50 | 1/100 | 1/200 | 1/300 | 1/500 |
| "Novel *lactobacillus*" (*L. casei*) | − | ± | + | ++ | + | + | ± |
| Other *L. casei* | − | − | ± | + | + | ± | ± |
| *L. acidophilus* | − | − | ± | + | + | ± | ± |
| *L. pluntarum* | − | − | + | + | + | ± | ± |
| *L. burgaricus* | − | − | ± | + | + | ± | ± |
| *L. salivarius* | − | − | + | + | + | ± | ± |
| *L. fermentum* | − | − | ± | + | + | ± | ± |

− Growth suppressed
± Growth neither suppressed nor promoted
+ Growth promoted

TABLE 9

Effect of this bactericidal disinfectant on growth of pathogenic bacteria

| | Normal concentration dilution of this bactericidal disinfectant contained in medium | | | | | | |
|---|---|---|---|---|---|---|---|
| | 1/10 | 1/30 | 1/50 | 1/100 | 1/200 | 1/300 | 1/500 |
| *P. gingivalis* | − | − | ± | ± | ± | ± | ± |
| *P. intermedia* | − | − | ± | ± | ± | ± | ± |
| *A. actinomycetem* | − | − | ± | ± | ± | ± | ± |
| *S. aureus* | − | − | ± | ± | ± | ± | ± |
| *S. pyogenes* | − | − | ± | ± | ± | ± | ± |
| *E. coli* O-157 | − | − | ± | ± | ± | ± | ± |
| *S. enteritidis* | − | − | ± | ± | ± | ± | ± |
| *Ps. Aeruginosa* | − | − | ± | ± | ± | ± | ± |
| *V. parahaemoliticus* | − | − | ± | ± | ± | ± | ± |

− Growth suppressed
± Growth neither suppressed nor promoted
+ Growth promoted

EXAMPLES

The present invention is explained in detail below based on examples, but the of the present invention is not limited to these. The manufacturing processes can be changed, and any cell numbers can of course be obtained by using a known extender or excipient. The preparation can be formulated in any way together with appropriate excipients, as a powder, granules, capsules or the like for example.

Manufacturing Example 1

The *Lactobacillus casei* (FERM BP-10059, FERM P-19443) of the present invention was seeded in 10 L of medium of pH 7.2 containing 10 g of peptone, 5 g of meat extract, 5 g of yeast extract, 10 g of lactose, 2 g of $K_2HPO_4$, 0.1 g of $MgSO_4.7H_2O$, 1 g of NaCl, 2 g of diammonium citrate, 5 g of sodium acetate, 3 g of $CaCO_3$, 0.3 g of $MnSO_4.5H_2O$, 0.03 g of $FeSO_4.7H_2O$ and 1 g of L-cysteine per liter, and cultured anaerobically for 72 hours at 37° C. After completion of culture, the culture liquid was paper filtered to remove the $CaCO_3$, and 3 L of the filtrate was refrigerated while the remaining liquid was centrifuged to obtain a supernatant and an 8.4 g bacterial mass. This was then washed in 420 ml of physiological saline solution, and centrifuged twice. The resulting purified bacterial mass was placed in a solution consisting of 70 g skim milk, 20 g soluble starch, 0.5 g sodium glutamate and 1000 ml purified water, agitated, and vacuum freeze dried by ordinary means to obtain 101 g of bacterial preparation. When measured, the cell count of this bacterial preparation was $2.5 \times 10^{10}$ cells/g. The resulting preparation consisted of 101 g of freeze-dried bacterial cells (including preservative), 3000 ml of culture liquid and 6700 ml of culture filtrate (disinfected liquid).

Manufacturing Example 2

The *Lactobacillus casei* (FERM BP-10059, FERM P-19443) of the present invention was seeded in 10 L of medium of pH 6.8 containing 3 g of casamino acids, 2 g of yeast extract, 50 ml of tomato juice, 2 g of glucose, 1 g of NaCl, 1 g of $KH_2PO_4$, 0.7 g of $MgSO_4.7H_2O$, 1 g of $CaCl_2.2H_2O$, 0.5 ml of Tween 80 and 0.5 g of soluble starch per liter, and cultured in a facultative anaerobic culture for 96 hours at 30° C. After completion of culture, 3 L of the culture liquid was refrigerated while the remaining 7 L was centrifuged to obtain a supernatant and a 5.6 g bacterial mass. This was then washed in 280 ml of physiological saline solution, and centrifuged again. 2.6 g of the resulting purified bacterial mass was mixed well with 10.4 g of potato starch, and refrigerated. The remaining 3 g of purified bacterial mass was placed in a solution consisting of 15 g of skim milk, 15 g of soluble starch, 5 g of trehalose, 0.2 g of cysteine and 500 ml of purified water, agitated, and vacuum freeze dried by ordinary means to obtain 39 g of bacterial preparation. When measured, the cell count of this bacterial preparation was $2\times10^{10}$ cells/g. The resulting preparation consisted of 39 g of freeze-dried bacterial cells (including preservative), 13 g of wet bacterial cells (including preservative), 3000 ml of culture liquid and 6700 ml of culture filtrate (disinfected liquid).

Manufacturing Example 3

The *Lactobacillus casei* (FERM BP-10059, FERM P-19443) of the present invention was seeded in 5 L of medium containing 100 g of skim milk and 1 g of trehalose per liter which had been adjusted to pH 6.8, and cultured in a facultative anaerobic culture for 72 hours at 37° C. Next, 75 g of trehalose was added to this culture liquid (yoghurt), which was well agitated and vacuum freeze dried by ordinary methods to obtain 590 g of bacterial preparation. When counted, the cell count of this bacterial preparation was $5\times10^9$ cells/g. The resulting bacterial preparation contained bacterial cells and skim milk fermentation products.

Manufacturing Example 4

To prepare the novel lactobacillus (FERM BP-10059, FERM P-19443) preparation of the present invention, the antibiotic-resistant novel lactobacillus (FERM BP-10059, FERM P-19443) of the present invention was seeded in 10 L of medium of pH 7.2 containing 5 g of peptone, 3 g of meat extract, 2 g of yeast extract, 1 g of CGF, 5 g of starch, 1 g of lactose, 2 g of diammonium citrate, 3 g of sodium acetate, 0.2 g of $MgSO_4.7H_2O$, 0.03 g of $FeSO_4.7H_2O$ and 1 g of L-cysteine per liter, and cultured anaerobically for 3 days at 37° C. After completion of culture, the culture liquid was paper filtered to remove the $CaCO_3$ and then centrifuged, and 7.8 g of the resulting bacterial cells were dispersed in 370 ml of physiological saline solution and centrifuged again twice. The resulting purified cell mass was dispersed in 450 ml of previously sterilized 5% starch solution, and vacuum freeze dried by ordinary methods to obtain 30 g of novel lactobacillus preparation. The live cell content of this bacterial preparation was $1\times10^{11}$ cells/g.

Manufacturing Example 5

The purified cell bodies manufactured in Manufacturing Example 4 were mixed with 15.7 ml of olive oil to manufacture an oil preparation. The live cell content of this bacterial preparation was $2\times10^{11}$ cells/g. 10 g of this oil preparation was mixed into 10 g of hydrophilic ointment to manufacture a lactobacillus cream. Next, 400 mg of amoxicillin (AMPC), 100 mg of erythromycin (EM), 100 mg of fradiomycin (FRM) and 100 mg of cefaclor (CCL) as antibiotics were mixed with the lactobacillus cream to manufacture an antibiotic-containing lactobacillus cream.

Example 1

The speed and percentage of S-R mutations in *E. coli* O-157 due to the effects of toxin-weakening antibiotics produced by *Lactobacillus casei* when *E. coli* O-157 and *Lactobacillus casei* were both present were investigated by means of a mixed culture of *E. coli* O-157 and the original *Lactobacillus casei* species (FERM BP-6971) and a mixed culture of *E. coli* O-157 and the *Lactobacillus casei* species of the present invention (FERM BP-10059, FERM P-19443). The medium was composed of 5 g of meat extract, 1 g of yeast extract, 5 g of peptone, 2 g of NaCl, 1 g of $CaCO_3$ and 2 g of glucose or starch per liter, with the pH adjusted to 7.2. Culture was anaerobic at 37° C., with subcultures every 72 hours which were diluted and applied each time to plate medium. The resulting colonies were observed, and the numbers of S types (original) and R types (toxin-weakened) were counted and the percentages compared. The results are shown in Table 10 and Table 11. As shown in Table 10, when glucose was used as the sugar cell counts fluctuated greatly with subculturing when *E. coli* O-157 was subcultured together with the original *Lactobacillus casei* (FERM BP-6971). From about the $5^{th}$ subculture the R type appeared (30%) and the percentage of R type increased as subculturing continued, so that all the bacteria were of the R type by the $18^{th}$ subculture. The S type did not reappear with subsequent subculturing. By contrast, when *E. coli* was subcultured together with the *Lactobacillus casei* species of the present invention (FERM BP-10059, FERM P-19443), the R type appeared by the third subculture at a rate of 5%, reaching 50% by the $5^{th}$ subculture, and by the $12^{th}$ subculture all of the *E. coli* O-157 were of the R type. That is, *E. coli* O-157 was affected more by the *Lactobacillus casei* species of the present invention than by the original *Lactobacillus casei* species. This is attributed to the difference in proliferation potency between the two *Lactobacillus casei* species.

TABLE 10

Results of mixed culture of *E. coli* O-157 with the original *Lactobacillus casei* species and the *Lactobacillus casei* species of the present invention with glucose as the sugar

| | Original L. casei | E. coli O-157 | | | L. casei of invention | E. coli O-157 | | |
|---|---|---|---|---|---|---|---|---|
| | | S | R | R % | | S | R | R % |
| $1^{st}$ Generation | $1.2 \times 10^9$ | $4.0 \times 10^9$ | 0 | 0% | $1.4 \times 10^9$ | $3.2 \times 10^9$ | 0 | 0% |
| $3^{rd}$ gen. | $1.2 \times 10^9$ | $3.5 \times 10^9$ | 0 | 0% | $1.7 \times 10^9$ | $2.8 \times 10^9$ | $1.5 \times 10^8$ | 5% |
| $5^{th}$ gen. | $1.5 \times 10^9$ | $2.5 \times 10^9$ | $1.0 \times 10^9$ | 30% | $2.0 \times 10^9$ | $1.0 \times 10^9$ | $1.0 \times 10^9$ | 50% |

TABLE 10-continued

Results of mixed culture of *E. coli* O-157 with the original
*Lactobacillus casei* species and the *Lactobacillus casei*
species of the present invention with glucose as the sugar

|  | Original | *E. coli* O-157 | | | *L. casei* of | *E. coli* O-157 | | |
|---|---|---|---|---|---|---|---|---|
|  | *L. casei* | S | R | R % | invention | S | R | R % |
| $7^{th}$ gen. | $1.4 \times 10^9$ | $1.1 \times 10^9$ | $1.1 \times 10^9$ | 50% | $2.0 \times 10^9$ | $5.0 \times 10^8$ | $1.5 \times 10^9$ | 75% |
| $10^{th}$ gen. | $1.0 \times 10^9$ | $1.4 \times 10^9$ | $1.6 \times 10^9$ | 55% | $1.8 \times 10^9$ | $1.0 \times 10^8$ | $1.2 \times 10^9$ | 90% |
| $12^{th}$ gen. | $1.2 \times 10^9$ | $9.0 \times 10^8$ | $2.1 \times 10^9$ | 70% | $1.5 \times 10^9$ | 0 | $1.2 \times 10^9$ | 100% |
| $15^{th}$ gen. | $1.5 \times 10^9$ | $3.5 \times 10^8$ | $2.1 \times 10^9$ | 85% | $2.0 \times 10^9$ | 0 | $8.0 \times 10^8$ | 100% |
| $18^{th}$ gen. | $1.3 \times 10^9$ | 0 | $1.5 \times 10^9$ | 100% | $2.0 \times 10^9$ | 0 | $8.0 \times 10^8$ | 100% |
| $20^{th}$ gen. | $1.4 \times 10^9$ | 0 | $1.7 \times 10^9$ | 100% | $1.8 \times 10^9$ | 0 | $1.0 \times 10^8$ | 100% |

As shown in Table 11, when starch was used as the sugar the proliferative potency of *E. coli* O-157 declined, but proliferation of the original *Lactobacillus casei* species declined still more, and the final cell count was less than $5 \times 10^8$ cells. Because of this reduction in effectiveness the *E. coli* O-157 mutated more slowly to the R type, with a percentage of 10% in the $7^{th}$ generation and 50% in the $20^{th}$ generation. The percentage of R type never exceeded 70% with continued subculturing. However, the proliferative potency of the *Lactobacillus casei* species of the present invention was no different than with glucose, and in this case the proliferative potency of the *E. coli* O-157 declined with each subculture, with the percentage of R type reaching 15% in the $3^{rd}$ generation and 100% in the $7^{th}$ generation.

In addition to *E. coli* O-157, similar tests were performed using *Salmonella enteritidis* and *Shigella flexneri*, but as in the case of *E. coli* O-157 mutation into the R type was much faster with the *Lactobacillus casei* species of the present invention than with the original *Lactobacillus casei* species as shown in Table 12. When a strain of the pathogen that had mutated to the R type was administered orally and intraperitoneally to mice at the lethal dosage for the S type, the fatality rate was 0 and coats and behavior were no different than those of untreated mice, confirming that pathogenicity had mainly been eliminated.

TABLE 11

Results of mixed culture of *E. coli* O-157 with the original
*Lactobacillus casei* species and the *Lactobacillus casei*
species of the present invention with starch as the sugar

|  | Original | *E. coli* O-157 | | | *L. casei* of | *E. coli* O-157 | | |
|---|---|---|---|---|---|---|---|---|
|  | *L. casei* | S | R | R % | invention | S | R | R % |
| $1^{st}$ Generation | $5.0 \times 10^8$ | $2.0 \times 10^9$ | 0 | 0% | $1.5 \times 10^9$ | $2.0 \times 10^9$ | 0 | 0% |
| $3^{rd}$ gen. | $4.0 \times 10^8$ | $2.5 \times 10^9$ | 0 | 0% | $1.4 \times 10^9$ | $1.7 \times 10^9$ | $3.0 \times 10^8$ | 15% |
| $5^{th}$ gen. | $3.5 \times 10^8$ | $2.2 \times 10^9$ | 0 | 0% | $1.8 \times 10^9$ | $4.0 \times 10^8$ | $1.0 \times 10^9$ | 70% |
| $7^{th}$ gen. | $3.5 \times 10^8$ | $1.8 \times 10^9$ | $2.0 \times 10^8$ | 10% | $2.0 \times 10^9$ | 0 | $1.2 \times 10^9$ | 100% |
| $10^{th}$ gen. | $3.0 \times 10^8$ | $1.7 \times 10^9$ | $3.0 \times 10^8$ | 15% | $1.7 \times 10^9$ | 0 | $1.0 \times 10^9$ | 100% |
| $12^{th}$ gen. | $2.0 \times 10^8$ | $1.5 \times 10^9$ | $5.0 \times 10^8$ | 25% | $1.5 \times 10^9$ | 0 | $8.0 \times 10^8$ | 100% |
| $15^{th}$ gen. | $2.0 \times 10^8$ | $1.5 \times 10^9$ | $6.0 \times 10^8$ | 30% | $1.8 \times 10^9$ | 0 | $8.0 \times 10^8$ | 100% |
| $18^{th}$ gen. | $2.0 \times 10^8$ | $1.2 \times 10^9$ | $8.0 \times 10^8$ | 40% | $1.7 \times 10^9$ | 0 | $6.0 \times 10^8$ | 100% |
| $20^{th}$ gen. | $1.5 \times 10^8$ | $8.0 \times 10^8$ | $8.0 \times 10^8$ | 50% | $1.8 \times 10^9$ | 0 | $5.0 \times 10^8$ | 100% |

TABLE 12

Rates of appearance of R-type pathogens in mixed culture

| Number of subcultures | Salmonella enteritidis | | Shigella flexneri | |
| --- | --- | --- | --- | --- |
| | Mixed culture w/original L. casei | Mixed culture w/L. casei of invention | Mixed culture w/original L. casei | Mixed culture w/L. casei of invention |
| 5 | 20% | 40% | 5% | 15% |
| 10 | 40% | 80% | 25% | 50% |
| 15 | 55% | 90% | 35% | 70% |
| 20 | 70% | 95% | 50% | 80% |
| 25 | 75% | 100% | 50% | 100% |
| 30 | 80% | 100% | 55% | 100% |
| 35 | 80% | 100% | 70% | 100% |
| 40 | 90% | 100% | 75% | 100% |
| 45 | 95% | 100% | 80% | 100% |
| 50 | 90% | 100% | 75% | 100% |
| 60 | 95% | 100% | 80% | 100% |
| 70 | 100% | 100% | 85% | 100% |
| 80 | 100% | 100% | 90% | 100% |
| 90 | 100% | 100% | 100% | 100% |

TABLE 12-continued

Rates of appearance of R-type pathogens in mixed culture

| Number of subcultures | Salmonella enteritidis | | Shigella flexneri | |
| --- | --- | --- | --- | --- |
| | Mixed culture w/original L. casei | Mixed culture w/L. casei of invention | Mixed culture w/original L. casei | Mixed culture w/L. casei of invention |
| 100 | 100% | 100% | 90% | 100% |
| 110 | 100% | 100% | 100% | 100% |
| 120 | 100% | 100% | 100% | 100% |

Example 2

A test has already been done in which daily ingestion of 2 g of the freeze-dried bacterial cells ($5 \times 10^8$ cells/g) manufactured in Manufacturing Example 1 and consisting of the original Lactobacillus casei caused an increase in Lactobacillus and Bifidobacterium, which are known as beneficial components of the intestinal flora, and conversely a decrease in Clostridium and Veillonella, which are known as harmful bacteria. In this example the results of ingestion of the Lactobacillus casei species of the present invention by 10 healthy subjects were measured and compared over time for 3 months. The results are shown in Table 13. When the original Lactobacillus casei (FERM BP-6971) was ingested Bifidobacterium increased about 90% in 3 months and Lactobacillus casei increased 150%, while Clostridium decreased 50% and Veillonella decreased 25%. However, when the Lactobacillus casei of the present invention (FERM BP-10059, FERM P-19443) was ingested Bifidobacterium increased 133% in 3 months and Lactobacillus casei increased 300%, while Clostridium decreased 96% and Veillonella decreased 98.4%. That is, the effects on beneficial and harmful bacteria making up the intestinal flora are much greater with the Lactobacillus casei of the present invention. The ability to reduce harmful bacteria is particular striking.

TABLE 13

Changes in intestinal flora in healthy subjects

| | Original L. casei | | | | L. casei of invention | | | |
| --- | --- | --- | --- | --- | --- | --- | --- | --- |
| | | Changes in bacteria after ingestion | | | | Changes in bacteria after ingestion | | |
| | Before ingestion | 1 month | 2 months | 3 months | Before ingestion | 1 month | 2 months | 3 months |
| BENEFICIAL | | | | | | | | |
| Bifidobacterium | $1.1 \times 10^{10}$ | $1.3 \times 10^{10}$ | $1.9 \times 10^{10}$ | $2.0 \times 10^{10}$ | $1.2 \times 10^{10}$ | $1.8 \times 10^{10}$ | $2.5 \times 10^{10}$ | $2.8 \times 10^{10}$ |
| Lactobacillus | $2.0 \times 10^{7}$ | $2.5 \times 10^{7}$ | $3.2 \times 10^{7}$ | $5.0 \times 10^{7}$ | $2.5 \times 10^{7}$ | $5.0 \times 10^{7}$ | $8.0 \times 10^{7}$ | $1.0 \times 10^{8}$ |
| HARMFUL | | | | | | | | |
| Chlostridium | $1.0 \times 10^{5}$ | $8.0 \times 10^{4}$ | $7.0 \times 10^{4}$ | $5.0 \times 10^{4}$ | $1.2 \times 10^{5}$ | $5.0 \times 10^{4}$ | $1.0 \times 10^{4}$ | $3.0 \times 10^{3}$ |
| Veillonella | $7.0 \times 10^{5}$ | $6.0 \times 10^{5}$ | $5.0 \times 10^{5}$ | $4.5 \times 10^{5}$ | $6.0 \times 10^{5}$ | $1.0 \times 10^{5}$ | $2.0 \times 10^{4}$ | $1.0 \times 10^{4}$ |

Example 3

Next, 2 g of the freeze-dried bacterial cells manufactured in the aforementioned Lactobacillus casei Manufacturing Example 1 were administered to 10 invalids, and bacteria were measured and compared over time for 3 months. The results are shown in Table 14. As shown in Tables 13 and 14, before administration the healthy subject had about 2 times the number of beneficial bacterial in their intestinal flora as did the invalids, and only about ⅓ the numbers of harmful bacteria. This shows that the state of the intestinal flora reflects the current state of health. In response to a survey, all of the healthy subjects who had participated in the test felt themselves to be healthier, while the invalids reported more confidence in their health. Specific responses included reports that (1) fatigue decreased, (2) color improved, (3) stool abnormalities cleared up, (4) skin regained tautness and beauty, (5) obesity improved, (6) high blood pressure returned to normal and (7) atopy was considerably improved, and the proportion of such responses was much greater among those who ingested the Lactobacillus casei of the present invention.

TABLE 14

Changes in intestinal flora of invalids

| | Original *L. casei* | | | | *L. casei* of invention | | | |
|---|---|---|---|---|---|---|---|---|
| | Before ingestion | Changes in bacteria after ingestion | | | Before ingestion | Changes in bacteria after ingestion | | |
| | | 1 month | 2 months | 3 months | | 1 month | 2 months | 3 months |
| BENEFICIAL | | | | | | | | |
| *Bifidobacterium* | $5.0 \times 10^9$ | $5.2 \times 10^9$ | $6.0 \times 10^9$ | $6.5 \times 10^9$ | $4.0 \times 10^9$ | $6.0 \times 10^9$ | $8.0 \times 10^9$ | $1.0 \times 10^{10}$ |
| *Lactobacillus* | $1.0 \times 10^7$ | $1.2 \times 10^7$ | $1.5 \times 10^7$ | $2.5 \times 10^7$ | $1.0 \times 10^7$ | $1.5 \times 10^7$ | $2.0 \times 10^7$ | $4.0 \times 10^7$ |
| HARMFUL | | | | | | | | |
| *Chlostridium* | $7.0 \times 10^5$ | $6.0 \times 10^5$ | $6.0 \times 10^5$ | $4.0 \times 10^5$ | $5.0 \times 10^5$ | $8.0 \times 10^4$ | $2.0 \times 10^4$ | $8.0 \times 10^3$ |
| *Veillonella* | $2.0 \times 10^6$ | $1.7 \times 10^6$ | $1.5 \times 10^6$ | $1.3 \times 10^6$ | $2.5 \times 10^6$ | $1.0 \times 10^6$ | $5.0 \times 10^5$ | $2.5 \times 10^5$ |

Example 4

Three W 600 mm×D 200 mm×H 150 mm planters were prepared, and each was filled with normal field soil mixed with 100 g of ripe compost and 12 g of chemical fertilizer (Nippon Godo Fertilizer Co. Green Map, N: 8%, P: 5%, K: 5%) and scattered with 10 g of magnesium lime (NAC Co., soil improver consisting of 5 to 7% magnesium oxide mixed with slaked lime). Next, furrows were made to a depth of 5 to 8 mm, and planted by hand with radish seeds. Germination occurred on the fifth day, and on the following day 2 g of centrifuged bacterial mass consisting of original *Lactobacillus casei* (FERM BP-6971) that had been cultured in the medium described in Manufacturing Example 2 was added to 200 ml, agitated well and applied to the control group. Meanwhile, 2 g of centrifuged bacterial mass consisting of the *Lactobacillus casei* of the present invention (FERM BP-10059, FERM P-19443) that had been cultured in the medium described in Manufacturing Example 2 was added to 200 ml of water, agitated well and applied to the test group. Water alone was applied to the untreated group. On about the $10^{th}$ day after emergence of leaves these were culled at about 5 cm intervals, leaving 30 radish plants in each planter. Suspensions of the respective centrifuged cell masses were applied to the control group and test group together with 150 ml of a 500 times dilution of fertilizer, while only 150 ml of a 500 times dilution of fertilizer was applied to the untreated group. The radishes were then watered as necessary to prevent them from drying out and harvested on the $28^{th}$ day. The results are as shown in Table 15. The radishes harvested from the test group that was treated with the *Lactobacillus casei* of the present invention were superior not only to the untreated radishes but also to the plants in the control group which were treated with the original *Lactobacillus casei* in terms of all measures of quality including weight, luster, smell, flesh, taste and crispness.

TABLE 15

Radish growth results

| | Growth | Wt (av. | Quality | | | |
|---|---|---|---|---|---|---|
| Group | progress | g/radish) | Luster | Smell | Flesh | Taste |
| Untreated group | 2 of 30 weakened during the test, only reached 5 g | 8.1 g | Bright red | + | Some pores, also cracks | Normal |

TABLE 15-continued

Radish growth results

| | Growth | Wt (av. | Quality | | | |
|---|---|---|---|---|---|---|
| Group | progress | g/radish) | Luster | Smell | Flesh | Taste |
| Control group | Lush foliage, pores developed if left unharvested | 7.2 g | Bright red | + to ++ | Dense flesh | Somewhat sweet |
| Test group | Foliage lush and glossy, no pores developed even if left unharvested | 11.8 g | Dark red | ++ | Very dense flesh, crispy | Very sweet |

Example 5

A growing test was performed with test groups as in Example 4 by hydroponic cultivation of white radish sprout seeds. Sponge was spread on the bottom of a W 100×D 100×H 180 mm polyethylene box, soaked with water, and sown overall with white radish sprout seeds. With the temperature set to 22° C. these were covered with black cloth for 5 days to block the light, after which the cloth was removed and they were grown in natural light. For the control group, 1 g of freeze-dried bacterial cells of the original *Lactobacillus casei* species (FERM BP-6971) were added to 100 ml of water, well agitated, and applied by misting on the $3^{rd}$ and $5^{th}$ days. For the test group, 1 g of freeze-dried bacterial cells of the *Lactobacillus casei* of the present invention (FERM BP-10059, FERM P-19443) manufactured in Manufacturing Example 1 were added to 100 ml of water, well agitated, and applied by misting on the $3^{rd}$ and $5^{th}$ days. Only water was applied to the untreated group. As shown by the growing results in Table 16, application of the *Lactobacillus casei* of the present invention resulted in better white radish sprouts than in the untreated group or control group.

TABLE 16

Growth results for white radish sprouts

| Group | Growth progress | Quality |
|---|---|---|
| Untreated group | Mean height 15.2 cm, outer stalks tall, inner stalks shorter | Texture: average Green and yellow-green somewhat blurred; not very sharp flavor |
| Control group | Mean height: 16.1 cm, outer stalks tall, inner stalks shorter | Texture: average-good Green and yellow-green clearly demarked; clear sharp flavor |
| Test group | Mean height: 16.8 cm, roughly uniform height, stalks thick and sturdy | Texture: good Shiny, green, yellow green and white very clearly demarked; mild sweet flavor as well as sharpness |

As is clear from Examples 1 through 5, the *Lactobacillus casei* species of the present invention, which has acquired various properties through acclimatization while retaining the properties of the original *Lactobacillus casei* species, has been confirmed to improve vitality to an incalculable extent in the living body, and is fundamentally a different strain from the original *Lactobacillus casei* species.

Example 6

Regarding the toxicity of *P. gingivalis* and *P. intermedia*, it has been shown that the quality and quantity of the toxins produced can be estimated from the results of animal tests by observing the color and smell of black colonies grown on blood plates and the strength of adhesiveness on the plate, while in the case of *A. actinomycetemcomitans*, the quality and quantity of toxins produced can be estimated from observing adhesiveness and hemolytic strength. We therefore cultured the aforementioned principal periodontal pathogens together with the "novel lactobacillus" to investigate what tendencies and reactions would be exhibited by the periodontal pathogens. Using Nissui modified GAM bouillon as the medium, the bacteria were cultured anaerobically at 37° C. with subcultures every 72 hours, at which time the culture was diluted and applied by ordinary methods to blood plate medium, and the cell counts and conditions of the resulting colonies were observed over time. The results are shown in Tables 17, 18 and 19. As is clear from Table 17, the cell count of *P. gingivalis* fell gradually with each subculture, disappearing by the $25^{th}$ subculture. During this time toxicity gradually weakened beginning with the $5^{th}$ subculture, and while some slight toxicity was still present by the $15^{th}$ subculture, by the $20^{th}$ it had virtually disappeared. It was confirmed that mice infected periodontally with this bacteria did not develop periodontitis. As is clear from Table 18, the cell count of *P. intermedia* declined gradually with subculturing, and the bacteria had disappeared by the $15^{th}$ subculture. Pathogenicity also declined as a result, disappearing by the $12^{th}$ subculture. As is clear from Table 19, the cell count of *A. actinomycetemcomitans* declined with each subculture, but not as rapidly as did *P. gingivalis* and *P. intermedia*. Past a certain point, however, *A. actinomycetemcomitans* declined rapidly, disappearing by the $18^{th}$ subculture. In mouse tests, pathogenicity had completely disappeared by the $12^{th}$ culture. Similar co-culture tests were performed using other bacteria implicated in periodontal disease, such as *F. nucleatum, B. forsythus, L. buccalis, E. corrodens* and also *Streptococcus*, which are common in the oral cavity, but all of these were overcome by the proliferative potency and bioactive substances of the lactobacillus of the present invention, and cell counts and toxicity were shown to decline with each subculture.

TABLE 17

Results of co-culture of *P. gingivalis* and FERM BP-10059

| | | P. gingivalis | | | | | |
|---|---|---|---|---|---|---|---|
| Number of subcultures | FERM BP-10059 | Cell count | Rate (%) | Color | Smell | Adhesiveness | Changes in pathogenicity |
| 1 | $1.8 \times 10^9$ | $2.2 \times 10^9$ | 55% | Black, shiny | Strong decay smell | Strong adhesiveness | Strong |
| 3 | $1.5 \times 10^9$ | $1.5 \times 10^9$ | 50% | Black, shiny | Strong decay smell | Strong adhesiveness | Moderate to strong |
| 5 | $1.8 \times 10^9$ | $5 \times 10^8$ | 22% | Blackish-brown | Moderate decay smell | Moderate adhesiveness | Moderate |
| 10 | $2 \times 10^9$ | $2 \times 10^8$ | 10% | Brown | Weak decay smell | Weak adhesiveness | Weak |
| 15 | $2.5 \times 10^9$ | $5 \times 10^7$ | 2% | Grey | Very weak decay smell | Easily peeled | Very weak |
| 20 | $3 \times 10^9$ | $1 \times 10^6$ | 0.3% | Whitish-grey | No smell | No adhesion | Almost none |
| 25 | $3 \times 10^9$ | 0 | 0% | | | | |

TABLE 18

Results of co-culture of *P. intermedia* and FERM BP-10059

| Number of sub-cultures | FERM BP-10059 | Cell count | Rate (%) | Color | Smell | Adhesiveness | Changes in pathogenicity |
|---|---|---|---|---|---|---|---|
| 1 | $2.1 \times 10^9$ | $2 \times 10^9$ | 48% | Black | Decay smell | Strong adhesiveness | Strong |
| 3 | $2.3 \times 10^9$ | $1 \times 10^9$ | 30% | Black | Decay smell | Moderate adhesiveness | Moderate |
| 5 | $2.5 \times 10^9$ | $2 \times 10^8$ | 7.4% | Center brown | Weak decay smell | Weak adhesiveness | Moderate to weak |
| 10 | $2.8 \times 10^9$ | $5 \times 10^7$ | 1.8% | Brown | Very weak decay smell | Almost no adhesiveness | Very weak |
| 12 | $3 \times 10^9$ | $1 \times 10^7$ | 0.3% | Grayish-white | No smell | None | Almost none |
| 15 | $3 \times 10^9$ | 0 | 0% | | | | |

(header spans *P. intermedia* over Cell count and Condition of colonies)

TABLE 19

Results of co-culture of *A. actinomycetemcomitans* and FERM BP-10059

| Number of sub-cultures | FERM BP-10059 | Cell count | Rate (%) | Hemolysis | Smell | Adhesiveness | Changes in pathogenicity |
|---|---|---|---|---|---|---|---|
| 1 | $2 \times 10^9$ | $2.3 \times 10^9$ | 53% | Strong (wide range) | Decay smell | Strong adhesiveness | Strong |
| 3 | $2.5 \times 10^9$ | $1.2 \times 10^9$ | 32% | Strong (wide range) | Decay smell | Strong adhesiveness | Strong |
| 5 | $2.5 \times 10^9$ | $8 \times 10^8$ | 24% | Moderate | Moderate decay smell | Moderate adhesiveness | Moderate |
| 10 | $2.5 \times 10^9$ | $2 \times 10^8$ | 7.4% | Weak (narrow range) | Weak decay smell | Weak adhesiveness | Weak |
| 12 | $2.8 \times 10^9$ | $1 \times 10^8$ | 3.4% | Weak (narrow range) | Weak decay smell | Weak adhesiveness | None |
| 15 | $3 \times 10^9$ | $3 \times 10^7$ | 1% | None | Faint decay smell | Almost none | None |
| 18 | $3 \times 10^9$ | 0 | 0% | | | | |

Example 7

When the "novel lactobacillus" (FERM BP-10059, FERM P-19443) is streak cultured anaerobically for 72 hours at 37° C. in the center of a plate with a 90 mm diameter, and various periodontal pathogens are streak cultured to the edge thereof, the development of the periodontal pathogens is arrested near the areas occupied by the FERM BP-10059 (FERM P-19443) by the effect of the antibiotic-like bioactive substances produced by FERM BP-10059 (FERM P-19443). We therefore observed how the growth range would change when periodontal pathogens growing at the edge where development was arrested were repeatedly fished out and streak cultured on growth plates of FERM BP-10059 (FERM P-19443). In this example, the FERM BP-10059 (FERM P-19443) was not mixed with the periodontal pathogens as in Example 5. Modified GAM medium was used on the plates. The results are as shown in Table 20. The range of arrest due to FERM BP-10059 (FERM P-19443) was about the same after several subcultures as in the initial culture, but past a certain point the range of arrest grew rapidly, and by the $13^{th}$ to $15^{th}$ subculture the pathogens had been eliminated from the Petri dish. Toxicity gradually declined at the same time and finally disappeared.

TABLE 20

Table 20. Effects of novel *lactobacillus* (FERM BP-10059) on bacteria causing periodontal disease

| Periodontal pathogen | Changes in range of arrest according to number of subcultures (mm) | | | | | | | |
|---|---|---|---|---|---|---|---|---|
| | Sub. 1 | 3 | 5 | 7 | 9 | 11 | 13 | 15 |
| *P. gingivalis* | 15 | 20 | 22 | 22 | 26 | 32 | 43> | |
| *P. intermedia* | 18 | 25 | 24 | 25 | 29 | 35 | 43> | |
| *A. actinomycetem* | 12 | 10 | 13 | 18 | 30 | 35 | 40 | 43> |
| *F. nucleatum* | 20 | 20 | 20 | 25 | 28 | 38 | 43> | |
| *B. forsythus* | 16 | 18 | 23 | 22 | 27 | 35 | 39 | 43> |

43> Smear cultured but did not grow

In a sensitivity test using existing antibiotics, the range of arrest gradually shrank in all cases with each passage, and resistance was finally achieved. That is, antibiotic-resistant strains appeared, and the bacterial toxins were either unchanged or often grew stronger. The appearance and spread of MRSA, VRE, and multidrug resistant *M. tuberculosis, Ps. aeruginosa* and the like is well known to be a serious problem worldwide. Examples 6 and 7 above are evidence that periodontal pathogens do not develop resistance due to the strong effects of FERM BP-10059 (FERM P-19443) whether they contact it directly or not, but rather their ability to grow and proliferate is suppressed over time and toxicity is completely eliminated.

Example 8

To measure the adhesiveness of the "novel lactobacillus" (FERM BP-10059, FERM P-19443) in periodontal pockets, a solution of cells ($2 \times 10^{10}$/ml) suspended in physiological saline was injected into pockets of equivalent depth, sterile physiological saline was injected into the pockets on the next day, and after 5 minutes the injected saline was aspirated out of the pockets and the growth and decline of FERM BP-10059 (FERM P-19443) was observed every day for a week. A mucilage of *L. acidophilus*, which colonizes mucous membranes, was prepared as a control, and this and the highly adhesive *B. natto* were injected separately in the same number and the progress observed. The results are shown in Table 21. When $2 \times 10^{10}$/ml of FERM BP-10059 (FERM P-19443) was injected, most (90% to 95%) were washed away, but the remaining bacteria persisted for about a week, and the colonization rate was higher the deeper the pocket. This means that FERM BP-10059 (FERM P-19443) is capable of growing using periodontal groove fluid as its main nutrient source, and can be more active in more advanced periodontal disease. By contrast, no *L. acidophilus* was seen from the $4^{th}$ day and no *B. natto* from the $3^{rd}$ day. That is, these bacteria could not establish themselves and proliferate in periodontal pockets.

TABLE 21

Growth and decline of bacteria injected into periodontal pockets

| Pocket depth (mm) | 1 hour after injection | Growth and decline injected bacteria (cells/ml) | | | | | | |
|---|---|---|---|---|---|---|---|---|
| | | After 1 day | 2 days | 3 days | 4 days | 5 days | 6 days | 7 days |
| FERM BP-10059 | | | | | | | | |
| 10 mm | $1 \times 10^9$ | $3 \times 10^8$ | $1 \times 10^8$ | $3 \times 10^7$ | $1 \times 10^7$ | $2 \times 10^6$ | $2 \times 10^4$ | 0 |
| 15 mm | $1 \times 10^9$ | $5 \times 10^8$ | $1.5 \times 10^8$ | $8 \times 10^7$ | $3 \times 10^7$ | $4 \times 10^6$ | $3 \times 10^5$ | $3 \times 10^4$ |
| 20 mm | $2 \times 10^9$ | $8 \times 10^8$ | $2 \times 10^8$ | $1 \times 10^8$ | $7 \times 10^7$ | $1 \times 10^7$ | $5 \times 10^6$ | $5 \times 10^5$ |
| *L. acidophilus* | | | | | | | | |
| 15 mm | $1 \times 10^9$ | $1 \times 10^8$ | $5 \times 10^6$ | $5 \times 10^3$ | 0 | 0 | 0 | 0 |
| *B. natto* | | | | | | | | |
| 10 mm | $5 \times 10^9$ | $5 \times 10^7$ | $3 \times 10^4$ | 0 | 0 | 0 | 0 | 0 |

Example 9

Growth and decline in cell numbers were observed when the "novel lactobacillus" (FERM BP-10059, FERM P-19443) was injected into periodontal pockets on successive days and when it was injected every other day. As shown in Table 22, when the bacteria was injected every day the cell counts in the pockets rose gradually, with colonization and proliferation being better the deeper the pocket, while when it was injected every other day colonization and proliferation of the bacteria was somewhat slower than with daily injection, but cell numbers rose gradually overall. This suggests that it is sufficient to inject the bacteria on alternate days.

TABLE 22

Growth and decline in FERM BP-10059 in periodontal pockets

| Periodontal pocket depth (mm) | Growth and decline in FERM BP-10059 (cells/ml) | | | | | | |
| --- | --- | --- | --- | --- | --- | --- | --- |
| | After 1 day | 2 days | 3 days | 4 days | 5 days | 6 days | 7 days |
| Daily injection | | | | | | | |
| 10 mm | $3.5 \times 10^8$ | $5 \times 10^8$ | $5 \times 10^8$ | $7 \times 10^8$ | $8 \times 10^8$ | $8 \times 10^8$ | $1 \times 10^9$ |
| 15 mm | $5 \times 10^8$ | $8 \times 10^8$ | $1 \times 10^9$ | $1.2 \times 10^9$ | $1.5 \times 10^9$ | $1.8 \times 10^9$ | $2 \times 10^9$ |
| 20 mm | $8.5 \times 10^8$ | $12 \times 10^9$ | $1.8 \times 10^9$ | $2.5 \times 10^9$ | $3.2 \times 10^9$ | $4 \times 10^9$ | $5 \times 10^9$ |
| Alternate day injection | | | | | | | |
| 10 mm | $3 \times 10^8$ | $1 \times 10^8$ | $4 \times 10^8$ | $1.5 \times 10^8$ | $6 \times 10^8$ | $2 \times 10^8$ | $6.5 \times 10^8$ |
| 15 mm | $5 \times 10^8$ | $1 \times 10^8$ | $6.5 \times 10^8$ | $2 \times 10^8$ | $8 \times 10^8$ | $2.5 \times 10^8$ | $1.2 \times 10^9$ |
| 20 mm | $8 \times 10^8$ | $2 \times 10^8$ | $1 \times 10^9$ | $3 \times 10^8$ | $2 \times 10^9$ | $8 \times 10^8$ | $2.8 \times 10^9$ |

The "novel lactobacillus" (FERM BP-10059, FERM P-19443) is not only effective against all kinds of acute and chronic infections, but is also effective in improving systemic chronic conditions such as diabetes which are factors associated with periodontal disease. That is, administration of the novel lactobacillus of the present invention increases the body's natural healing power, which translates into vitality. Vitality is the body's ability to promote growth and regenerate tissue.

Example 10

45 goldfish (Wakin) with an average length of 4.2 cm exhibiting initial symptoms of Saproglenia disease were divided into three groups, an untreated group, a control group and a test group, and observed for 2 months in a total of 9 water tanks with the water temperatures for each group set to 15° C., 20° C. and 25° C. Five goldfish were reared in 5 liters of water in each tank. 1 g of freeze-dried bacterial cells ($5 \times 10^6$ cells/ml of tank water) of the original *Lactobacillus casei* species (FERM BP-6971) was administered to the control group. 1 g of freeze-dried bacterial cells ($5 \times 10^6$ cells/ml of tank water) of the *Lactobacillus casei* species of the present invention (FERM BP-10059, FERM P-19443) manufactured in Manufacturing Example 1 was administered to the test group. The goldfish in the untreated group were reared without any treatment. The results are shown in Table 23. As shown in Table 23, in the untreated group all the goldfish died in less than a month regardless of water temperature, with a mean survival time of 18 days. In the control group receiving the original *Lactobacillus casei* species, all the goldfish died in less than a month in the 25° C. tank, with a mean survival time of 23 days, but in the tanks set to 15° C. and 25° C. the Saproglenia grew more slowly and the goldfish survived longer, with 2 dying after one month and another 2 dying after 2 months at 15° C., for a mortality rate of 80%. At 20° C., 2 died after one month and all after 2 months, for a mortality rate of 100%. By contrast, using the *Lactobacillus casei* species of the present invention 1 goldfish died on the 45 day of rearing in the 20° C. tank, while in the 25° C. tank 1 goldfish died on the 25$^{th}$ day and 1 goldfish died on the 50$^{th}$ day, but the other goldfish were all healthy and the Saproglenia adhering to their body surfaces declined until it was almost imperceptible. The growth rate was the same as that of healthy goldfish. This indicates that the *Lactobacillus casei* species of the present invention, which has been acclimated to low temperatures, is effective even at a low temperature of 15° C.

TABLE 23

Experimental results against Saproglenia disease in goldfish

| Water temp. | Group | After 1 month | 2 months | Death rate |
| --- | --- | --- | --- | --- |
| 15° C. | Untreated group | 5 dead | | 100% |
| | Control group | 2 dead | 2 dead | 80% |
| | Test group | All survived, mean length 4.4 cm | All survived, mean length 4.5 cm | 0% |
| 20° C. | Untreated group | 5 dead | | 100% |
| | Control group | 2 dead | 3 dead | 100% |
| | Test group | All survived, mean length 4.4 cm | 1 dead | 20% |
| 25° C. | Untreated group | 5 dead | | 100% |
| | Control group | 5 dead | | 100% |
| | Test group | 1 dead, mean length 4.5 cm | 1 dead | 40% |

Example 11

A feeding trial was performed in tanks set to the same conditions as in Example 10 using groups of 5 goldfish (Wakin) suffering from goldfish ulcer disease, in which *Aeromonas* invades through a wound and dissolves the surrounding flesh, causing the internal organs to be exposed in severe cases. The symptoms of goldfish ulcer disease ranged from mild to moderate, and the goldfish were reared for 2 months with the symptoms balanced among the tanks. The results are shown in Table 24. As shown in Table 24, the symptoms of the goldfish in the untreated group progressed regardless of water temperature, and within 2 months the organs were exposed and all fish died. In the control group receiving the original *Lactobacillus casei* species (FERM BP-6971), the fish with mild symptoms maintained their status at the lower water temperature, but when the water temperature was high the symptoms progressed slowly and ultimately 60% to 80% of the fish died within 2 months. By contrast, in the test group receiving the *Lactobacillus casei* species of the present invention (FERM BP-10059, FERM P-19443) those fish with mild symptoms were mostly cured regardless of water temperature. Even in the case of moderate symptoms the wounds gradually healed, and no fish died even after 2 months.

TABLE 24

Experimental results for goldfish ulcer disease

| Water temp. | Group | After 1 month | 2 months | Death rate |
|---|---|---|---|---|
| 15° C. | Untreated group | Wounds of even fish with mild symptoms gradually grew, 3 died | Wounds of even fish with mild symptoms grew, 2 died | 100% |
| | Control group | Fish with mild symptoms unchanged, wounds of those with moderate symptoms grew slightly | Fish with mild symptoms unchanged, all with moderate symptoms died | 60% |
| | Test group | Wounds of fish with mild symptoms closed in 1 month, fish with moderate symptoms unchanged, wounds closed slightly | Fish with mild symptoms recovered complete health, wounds of fish with moderate symptoms no longer obvious | 0% |
| 20° C. | Untreated group | As at 15° C., 1 fish with mild symptoms and 2 with moderate symptoms died | As at 15° C., remaining 2 fish died | 100% |
| | Control group | Fish with mild symptoms unchanged, wounds of fish with moderate symptoms grew slightly | Wound of 1 fish with mild symptoms grew rapidly, fish died, 2 with moderate symptoms died | 60% |
| | Test group | As at 15° C. | As at 15° C. | 0% |
| 25° C. | Untreated group | Wounds of even fish with mild symptoms grew rapidly, all died | | 100% |
| | Control group | Wounds of fish with mild symptoms grew, wounds of fish with moderate symptoms grew bit by bit | Wounds of fish with mild symptoms grew rapidly, 2 died, 2 fish with moderate symptoms died | 80% |
| | Test group | Fish with mild symptoms unchanged, wounds of fish with moderate symptoms closed gradually | Wounds of fish with mild symptoms no longer obvious, wounds of fish with moderate symptoms smaller with 1 exception | 0% |

Example 12

About 1 cm$^2$ of mouse skin was peeled off, after which water was applied twice morning and night to the untreated group, while centrifuged cells of the standard ATCC 393 strain of *L. casei* and the "novel lactobacillus" (FERM BP-10059, FERM P-19443) were applied to the bacterial treatment groups, and progress was observed. As shown in FIG. 1, when FERM BP-10059 (FERM P-19443) was applied it took only 3 days for a thin film to cover the entire surface of the wound, 8 days for the skin to recover entirely, and 22 days for the coat to grow back completely. By contrast, this took 4 days, 10 days and 28 days using ATCC 393 and 5 days, 12 days and 35 days using water. This test also shows the remarkable tissue restoring effects of the "novel lactobacillus" (FERM BP-10059, FERM P-19443).

Example 13

Figure 2:
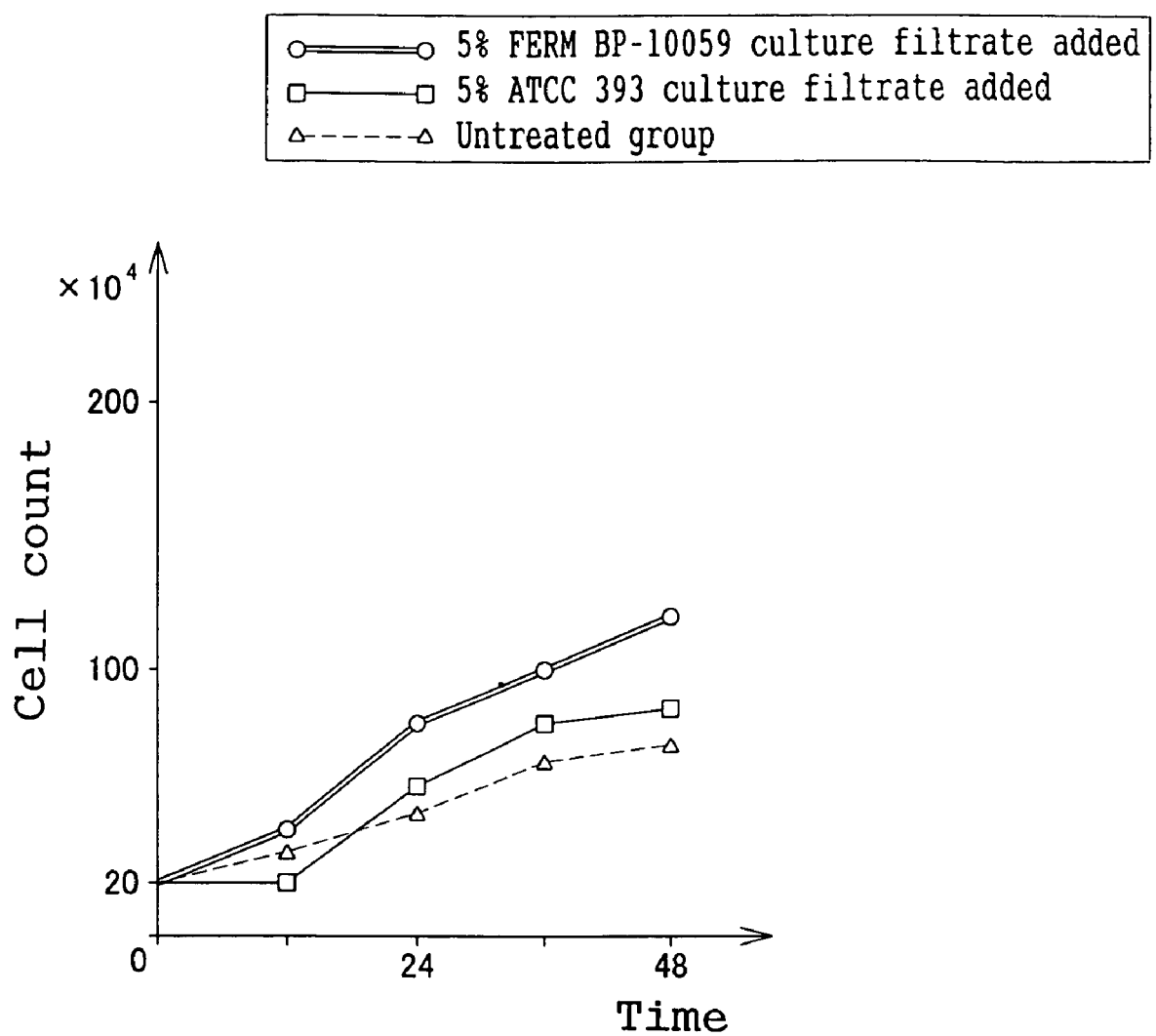
FIG. 2 shows proliferation of the monkey kidney V-1 cell strain.
Figure 3:
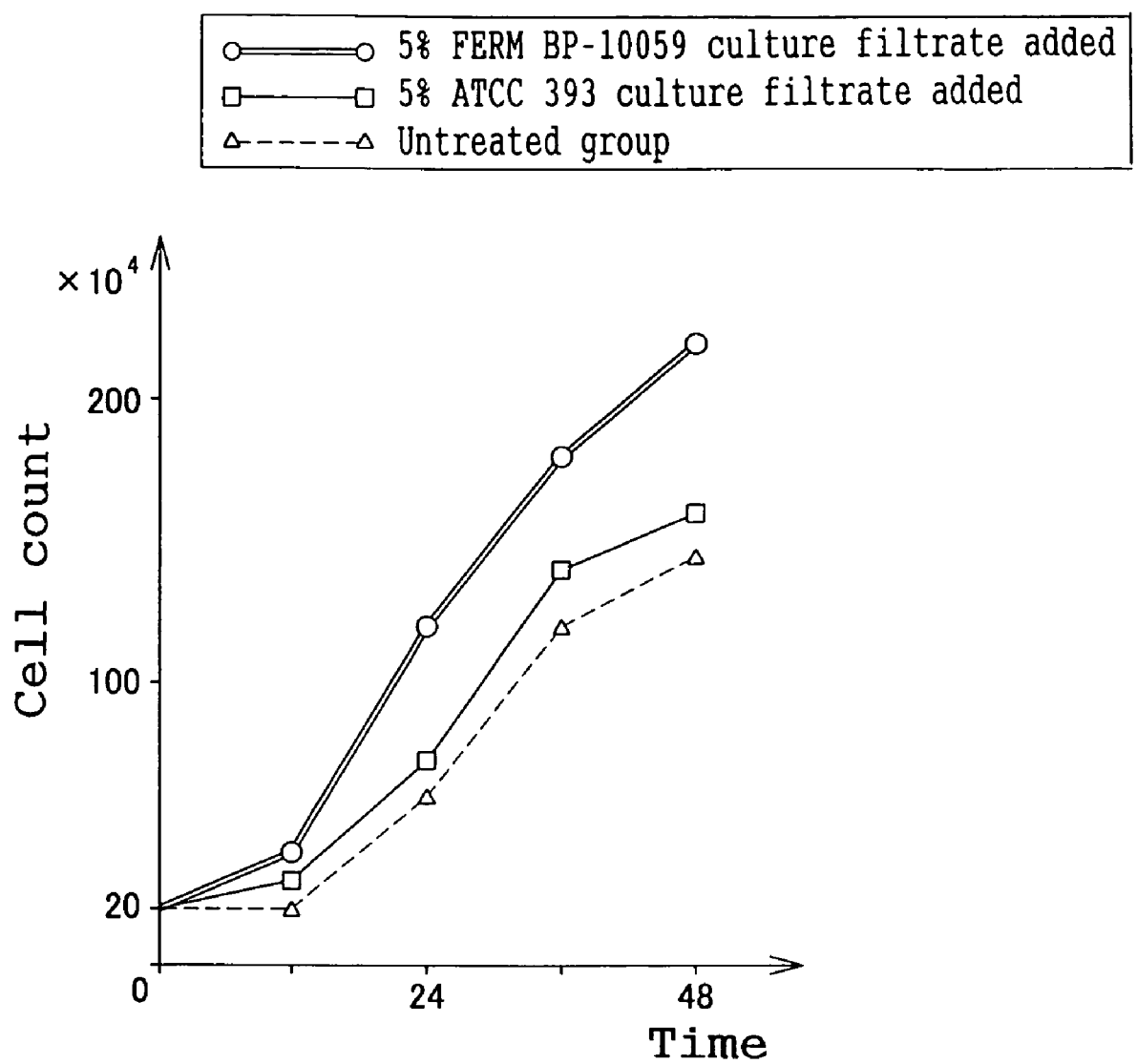
FIG. 3 shows proliferation of mouse mastocytoma cell strain P815.
Figure 4:
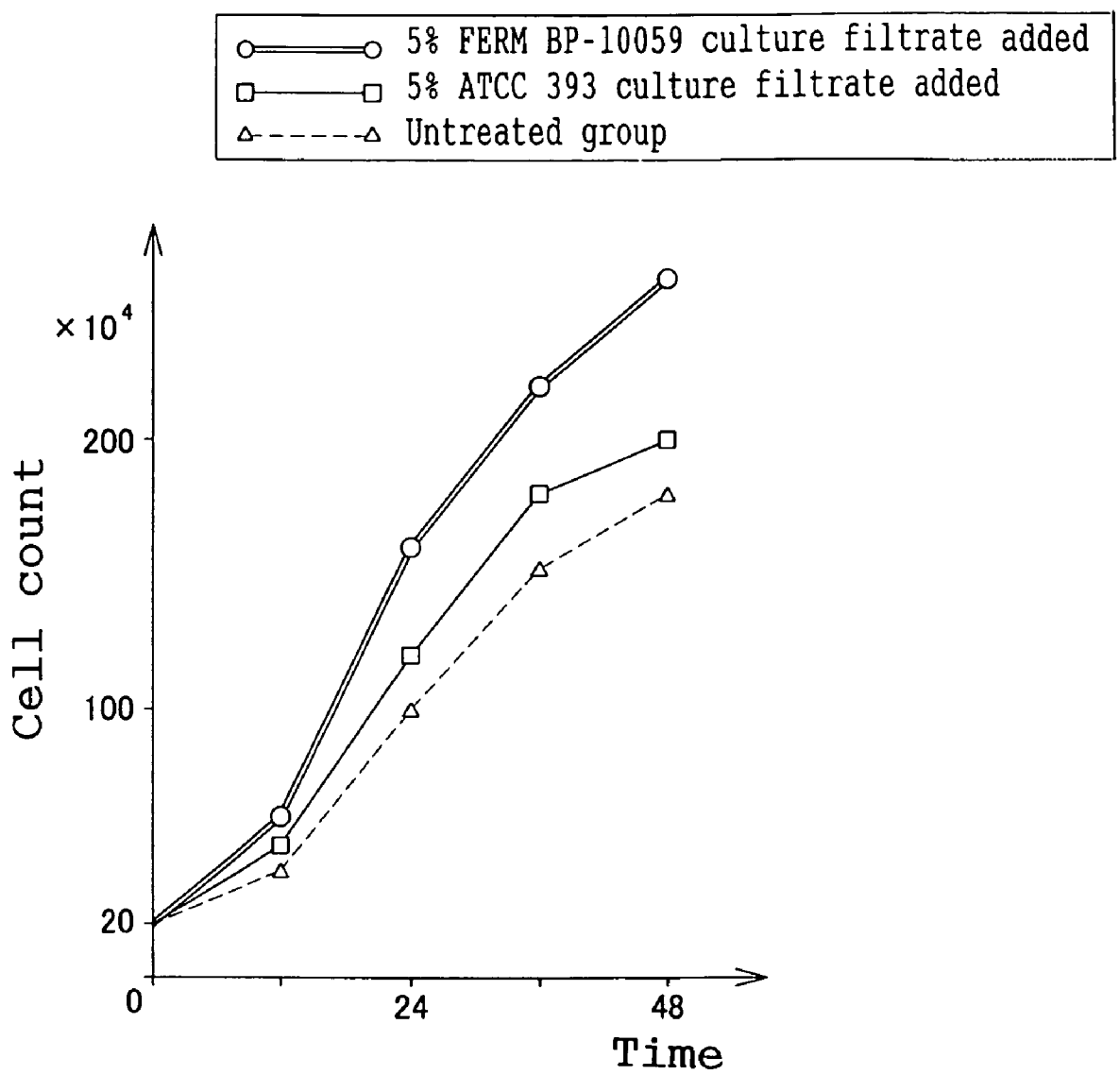
FIG. 4 shows proliferation of mouse CEA lymphocytes.
Figure 5:
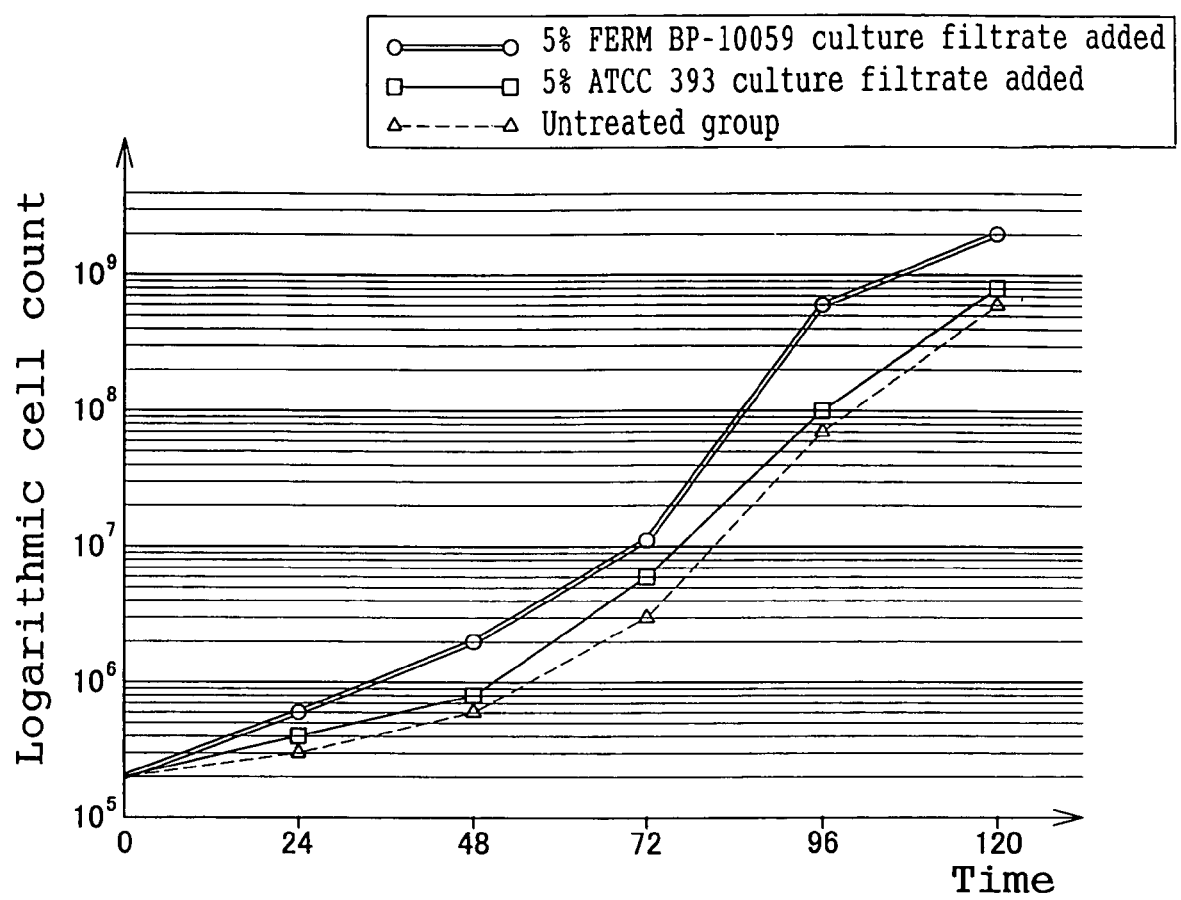
FIG. 5 shows proliferation of chlorella.

To investigate cell increase with animal cells and plant cells, the standard ATCC 393 strain of *L. casei* and the "novel lactobacillus" (FERM BP-10059, FERM P-19443) were seeded in medium of pH 7.2 containing 3 g of peptone, 2 g of tryptone, 3 g of meat extract, 1 g of CGF, 1 g of yeast extract, 3 g of starch, 1 g of trehalose, 1.5 g of $KH_2PO_4$, 0.7 g of $MgSO_4.7H_2O$, 1 g of NaCl, 1 g of diammonium citrate, 1 g of $(NH_4)_2HPO_4$, 2 g of sodium acetate, 2 g of $CaCO_3$, 0.2 g of $MnSO_4.xH_2O$, 0.03 g of $FeSO_4.7H_2O$, 0.01 g of $ZnSO_4$, 0.2 g of L-cysteine and 1 g of taurine per liter, and cultured anaerobically for 72 hours at 37° C., monkey kidney (V-1) cells, mouse P815 mastocytoma cells and mouse CEA lymphocytes were mixed $2\times10^5$ cells/ml with culture liquid consisting of Japan Pharmaceutical Co. GIT medium for animal culture to which 5% centrifuged supernatant from the lactobacillus cultures had been added or not added, and live cells were counted after 48 hours. The results are shown in FIGS. 2, 3 and 4. As shown in these figures, when 5% lactobacillus culture filtrate was added to their cell culture liquid the animal cells became more prolific, with an increase of 10 to 15% using the standard ATCC 393 strain and an increase of 40 to 50% using FERM BP-10059 (FERM P-19443). This indicates that substances produced by the lactobacilli (bioactive substances) stimulate and promote proliferation (cell division), and the increase in lymphocyte proliferation suggests a contribution to strengthening the immune system. Moreover, as shown in FIG. 5, in a similar test using chlorella plant cells the proliferation rate was also increased although not as much as with animal cells.

Periodontal pathogens have a variety of pathogenic factors which inflict direct or indirect damage on periodontal tissue, including adhesion-related factors, proteinases and toxins, substance that act as toxins, metabolic products and the like. Specific examples include endotoxins (LPSI), collagenases, trypsin-like enzymes, fibroblast-suppressing enzymes and other destructive enzymes, leukocytotoxins, streptolysin, hydrogen sulfide, fatty acids and other cell toxins as well as physical adhesion by means of long cilia to mucosal epithelium, red blood cells and other bacteria. Endotoxins in particular have numerous effects including activating osteoclasts (promoting absorption of alveolar bone), damaging fibroblasts and promoting immunopathological reactions (damaging the circulation of periodontal tissue). The "novel lactobacillus" (FERM BP-10059, FERM P-19443) not only blocks the proliferation of periodontal pathogens and acts to weaken their pathogenicity, but also converts and detoxifies some of the toxins produced by periodontal pathogens.

Example 14

Cells of periodontal pathogens were cultured for 120 hours anaerobically at 37° C. in modified GAM bouillon, collected by centrifugation, floated in physiological saline and washed three times by centrifugation. They were then floated uniformly in five times the amount of water and cooled to 0° C., and the same amount of an ice-cooled aqueous solution of 0.5 N trichloroacetic acid was added and left for 3 hours at 0° C. The cell body residue was then removed by centrifugation, 2 volume equivalents of chilled ethanol were added to the supernatant, and the precipitate was centrifuged. The precipitate was washed with a small amount of ethanol and then with ether, resulting in an endotoxin in the form of a white powder. A disk was impregnated with 5 mg of this endotoxin and dried to prepare a sensitivity disk. Next the *L. casei* standard ATCC 393 strain and the "novel *lactobacillus*" (FERM BP-10059, FERM P-19443) were applied to BCP plate medium containing 2.5 g yeast extract, 5 g peptone, 1 g glucose, 0.1 g L-cysteine, 1 g Polysorbate 80 and 0.06 g BCP per liter, the sensitivity disk prepared above was placed in the center of the medium, and the bacteria were cultured anaerobically for 48 hours at 37° C. As a result, growth of ATCC393 was blocked 12 mm from the edge of the disk, while the FERM BP-10059 (FERM P-19443) grew prolifically at the edge of the disk. This indicates that FERM BP-10059 (FERM P-19443) was incorporating these endotoxins into its cells as vitamin-like growth factors. Moreover, the "novel lactobacillus" (FERM BP-10059, FERM P-19443) has the ability to aggressively depress odiferous sulfur compounds such as fatty acids and hydrogen sulfide, and its proliferation is stimulated by the addition of these substances.

Example 15

Three groups of 15 patients suffering respectively from acute colitis, acute cystitis and conjunctivitis, diseases caused by similar bacteria and having similar symptoms, were each subdivided into 3 subgroups of 5 patients each. In each group, the A subgroup was treated for 5 days with 1000 mg/day of antibiotics alone, the B subgroup was treated for 5 days with 500 mg/day of antibiotics and for 10 days with 2 g/day ($5 \times 10^{10}$ cells/day) of freeze-dried cells of the antibiotic-resistant *Lactobacillus casei* species of the present invention (FERM BP-10059, FERM P-19443) manufactured by the methods of Manufacturing Example 1, and the C subgroup was first treated with 1000 mg/day of antibiotics alone, and once the acute symptoms had subsided the antibiotic was stopped (normally for 2 to 3 days) and the group was then treated like the B subgroup for 7 days with 2 g/day of freeze-dried bacterial cells. The average treatment effects for each group over 10 days are shown in Table 25. As is clear from Table 25, use of the lactobacillus preparation of the present invention in conjunction with conventional antibiotic administration for the treatment of acute infection or administration of the lactobacillus preparation of the present invention after administration of antibiotics offers great advantages, especially in light of the problems of drug resistance encountered with conventional therapy using only antibiotics, including (a) allowing the antibiotic dose to be reduced by half, (b) allowing the burden on patients to be greatly reduced by shortening the time required to reduce, ameliorate and eliminate symptoms with virtually no side-effects, and (c) avoiding such problems as disturbance of the intestinal flora and microbial substitution. For acute infections, the results are similar (with some differences in pathogens and symptoms) to the therapeutic results achieved with the original *Lactobacillus casei* species in Comparative Example 1 below.

TABLE 25

Therapeutic effects of the *Lactobacillus casei* species of the present invention against acute infection

| | Treatment method | Progress of symptoms and treatment results for 5 patients | Upset of intestinal flora[1] |
|---|---|---|---|
| Disease: acute colitis Principal pathogens: Pathogenic *E. coli* Antibiotic used: Cefaclor CCL | A | Diarrhea, abdominalgia, etc. improved in 3 days; pathogen hardly detected after 4 days; complete recovery in 6.5 days | ++ |
| | B | Diarrhea, abdominalgia, etc. improved in 2.5 days; pathogen not detected after 4 days, at which time recovery was complete judging from appetite and stool | ± |
| | C | Antibiotic given for 2 days, only *lactobacillus* preparation thereafter. Elimination of symptoms and complete recovery on $5^{th}$ day | − |
| Disease: acute cystitis Principal pathogen: Pneumobacillus Antibiotic used: minocycline (MINO) | A | Slight fever, urodynia, frequent urination, etc. improved in 5 days, urine cloudy for 7 days. Pathogen not detected by $4^{th}$ day, but urodynia and urge to urinate persisted, complete recovery in 10 days. | ++ |
| | B | Pathogen not detected by $3^{rd}$ day of antibiotic administration, urodynia, urge to urinate gone by day 7 | ± |
| | C | Pathogen not detected by $4^{th}$ day of antibiotic administration, after which only *lactobacillus* preparation administered. Urodynia and urge to urinate gone by day 7. | − |
| Disease: epidemic conjunctivitis Principal pathogen: *Staphylococcus aureus* Antibiotic used: Ofloxacin (OFLX) | A | Eyedrops containing antibiotic administered; eye congestion, fatigue, blurred vision, etc. gone in 7 days; pathogen gone in 4.5 days; complete recovery in about 2 wks. | − |
| | B | After administration of eyedrops containing antibiotic, eyes washed with aqueous solution of suspended *lactobacillus*. Pathogen gone in 4 to 5 days as in group A, symptoms gone in 5.5 days, complete recovery in only 1 week. | − |
| | C | In terms of pathogen detection, therapeutic results between those of groups A and B; complete recovery in 10 days. | − |

[1] ++ Drastic drop in overall numbers of intestinal bacteria, temporary but significant disruption in competitive balance among bacteria forming intestinal flora + Considerable drop in intestinal flora, some temporary disruption in competitive balance among bacteria forming intestinal flora ± Some changes but no great effect − No particular changes Comparative Example 1

As in Example 15, three groups of 15 patients suffering respectively from acute colitis, acute cystitis and conjunctivitis, diseases caused by similar bacteria and having similar symptoms, were each subdivided into 3 subgroups of 5 patients each. In each group, the A subgroup was treated for 5 days with 1000 mg/day of antibiotics alone, the B subgroup was treated for 5 days with 500 mg/day of antibiotics and for 10 days with 2 g/day ($5 \times 10^9$ cells/day) of freeze-dried cells of FERM BP-6972, one of the antibiotic-resistant original *Lac-* tobacillus casei species, which was manufactured by the methods of Manufacturing Example 1, and the C subgroup was first treated with 1000 mg/day of antibiotics alone, and once the acute symptoms had subsided the antibiotic was stopped (normally for 2 to 3 days) and the group was then treated like the B subgroup for 7 days with 2 g/day of freeze-dried bacterial cells. The average treatment effects for each group over 10 days are shown in Table 26. This Comparative Example corresponds to Test Example 1 (Table 6) of Japanese Patent Application Laid-open No. 2001-333766.

TABLE 26

Therapeutic effects of original *Lactobacillus casei* species against acute infection

| | Treat-ment method | Progress of symptoms and treatment results for 5 patients | Upset of intestinal flora[1] |
|---|---|---|---|
| Disease: acute colitis Principal pathogen: *Campylobacter* Antibiotic used: Erythromycin (EM) | A | Fever, diarrhea, abdominalgia, etc. better in 2.5 days; pathogen gone in about 3.5 days; complete recovery in 7 days, but in one case soft stool still present at this point | ++ |
| | B | Above symptoms improved in 3 days, pathogen gone in 5 days, at which point recovery was judged to have occurred | ± |
| | C | Same progress as A, recovery judged as best from general evaluation based on patient color, movement, stool, appetite, etc. | − |
| Disease: acute cystitis Principal pathogen: Pathogenic *E. coli* Antibiotic used: Cephalexin (CEX) | A | Pathogen not detected in 3 days, slight fever, urodynia, frequent urination, etc. gone in 6 days but some urodynia still present, complete recovery in 10 days | ++ |
| | B | Pathogen not detected on day 3 of administration as in Group A, urodynia and other symptoms gone by day 5 | ± |
| | C | Progress similar to group A, urodynia and other symptoms took 5 days to disappear | − |
| Disease: acute bronchitis Principal pathogen: *Streptococcus pneumoniae* Antibiotic used: Cefaclor (CCL) | A | Pathogen not entirely eliminated during treatment period, but fever, cough, sore throat and other cold symptoms generally gone by day 5; complete recovery took about 10 days | ++ |
| | B | As in A, pathogen not entirely eliminated, but very few detected; cold symptoms gone in 4 to 5 days; complete recovery took 7 days | ± |
| | C | Detected pathogen numbers and clinical results were intermediate between groups A and B | − |

[1] ++ Drastic drop in overall numbers of intestinal bacteria, temporary but significant disruption in competitive balance among bacteria forming intestinal flora + Considerable drop in intestinal flora, some temporary disruption in competitive balance among bacteria forming intestinal flora ± Some changes but no great effect − No particular changes There are many theories regarding the mechanism of occurrence periodontal disease, but the consensus is that it occurs as a chronic inflammatory condition caused by an accumulation of plaque. Plaque is an aggregation of many types of bacteria that produce toxins which cause inflammation of the gums, and if this progresses the periodontal pockets between the teeth and gums are pushed open, halitosis occurs, and the supporting tissue of the teeth including the periodontal ligament and alveolar bone is destroyed. 0.80% of adults suffer to some degree from periodontal disease, which can spread to the surrounding teeth and result in tooth loss if left untreated, and it is recognized as a typical model of a disease which is still difficult to cure. The principal pathogens include *Poryphyromonas gingivalis, Actinobacillus actinomycetemcomitans, Provoutel intermedia, Prevotella intermedia* and the like, which do not produce toxins like food poisoning bacteria so that the disease progresses with few subjective symptoms and in many cases it is too late for treatment once it is diagnosed. Moreover, the oral cavity is constantly being contaminated by bacteria and provides a suitable environment for their proliferation, so that the problem continues to recur, and unfortunately there are few dentists who can reliably treat periodontal disease. The symptoms that occur when lesions develop deep in the gums and pus continues to seep out are similar to those of hemorrhoids, suggesting some kind of deep association in the occurrence of intractable infections at the entrance and exit to the digestive tract. Prevention and treatment of periodontal disease basically consists of the following. (1) As much as possible of the plaque and calculus (plaque residue) is removed by brushing, or more recently is destroyed and removed efficiently with ultrasound and lasers or dissolved with special chemicals (removal of bacterial bed). (2) A disinfectant, antibiotic or anti-inflammatory enzyme preparation is administered by injection into the periodontal pocket until the inflamed area improves, in an effort to suppress the inflammation. (3) However, when the site of inflammation is deep and treatments (1) and (2) above do not produce favorable results by themselves, the site of inflammation or damage is removed by surgery. (4) Subsequently, the gums are sewn up or reconstructed with artificial material. Recent attempts have been made to encourage regeneration of periodontal tissue by injecting drugs having enamel-forming proteins as their main components. (5) When all treatments are ineffective, the teeth are pulled and reconstructed. That is, the goal is to control inflammation of the gums, stop the progress of the periodontal disease, regenerate lost periodontal tissue, improve external appearance and maintain newly regained tissue.

Example 16

20 periodontal disease patients were divided into 4 groups (A through D) with five people in each group, and once as much plaque and tartar as possible had been removed from all patients by scaling and root planning, the periodontal pockets were filled either with an antibiotic ointment or with freeze-dried bacterial cells of the present invention made into a gel with a small amount of water. In Group A, an antibiotic was used alone or together with an anti-inflammatory enzyme preparation as necessary. In Group B, a preparation consisting of a mixture of equal amounts of the antibiotic-resistant freeze-dried bacterial cells manufactured in Manufacturing Example 1 and the antibiotic-resistant bacterial preparation manufactured in Manufacturing Example 3 was administered together with an antibiotic. In Group C, an antibiotic or anti-inflammatory enzyme preparation was administered initially, followed by the aforementioned bacterial preparation. In Group D, no antibiotic was used from the beginning, and only the bacterial preparation was administered. For purposes of treatment the principal causative bacteria were isolated and tested for drug sensitivity, and the appropriate antibiotic was selected in each case based on the results. The results are shown in Tables 27 and 28. As can be seen from Tables 27 and 28, administration of the lactobacillus preparation of the present invention either alone or together with an antibiotic resulted in elimination of the causative bacterial in less than half a month even in cases of periodontal disease for which antibiotics or anti-inflammatory enzymes alone were expected to have very little effect, and with 1 to 2 months of continuous administration effects were achieved which could never have been achieved with conventional therapy, including elimination of bad breath and improvements in gum condition, the inside of the periodontal pockets and loose teeth, although with individual differences. Thus, the therapeutic effects of the original *Lactobacillus casei* strain as described in Comparative Example 2 below have been further improved upon, and dramatic effects on the thickness and firmness of the gum tissue of the periodontal pockets are worth noting.

TABLE 27

Therapeutic results for periodontal disease using the *Lactobacillus casei* species of the present invention

| Method | Patients Name | Age | Sex | Severity | Main patho-gens | Anti-biotic (abbrev) | Admin Period | Treatment progress and results |
|---|---|---|---|---|---|---|---|---|
| A | W.S. | 48 | F | Shallow 3⌉5⌉ | *Ps. gingivalis* *C. rectus* | Mino-cycline (MINO) | | Administered for 2 wks with little improvement; some improvement in swelling, progress of other symptoms arrested; status quo maintained |
| | K.K. | 72 | M | Medium ⌈2 ⌈4 ⌊5 ⌊6 | *Ps. gingivalis* *F. nucleatum* | Mino-cycline (MINO) | | Administered for 2 wks with no improvement; halitosis and swelling unchanged but pus slightly less |
| | M.T. | 62 | M | Deep ⌈5 6⌉ | *Ps. gingivalis* *B. forsythus* | Cefaclor (CCL) | | Administered for 3 weeks with little improvement; no change in severe halitosis, reddish-black gums, swelling; little improvement in drainage, bleeding |
| B | A.I. | 58 | F | Shallow ⌊2 ⌊3 | *Ps. gingivalis* | Cefaclor (CCL) | 30 days | Slight improvement starting on day 3 of administration, halitosis gone by day 3, gum color & swelling better by day 15; by day 30 periodontal pocket largely closed, complete recovery expected with further treatment |
| | H.T. | 52 | M | Medium ⌈4 ⌈5 | *Sta. aureus* *Fuso. nucleatum* | Mino-cycline (MINO) | 30 days | Symptoms began to improve on day 7, drainage & bleeding mostly stopped; periodontal pocket shrunk somewhat but not completely; however, gums were tight, patient could chew hard foods |
| | M.H. | 64 | M | Deep 3⌉5⌉ | *Ps. gingivalis* *A. actinomycetemcomituns* | Mino-cycline (MINO) | 30 days | Pathogen disappeared by day 5, symptoms cleared up beginning around day 7, by day 10 drainage & bleeding had stopped and halitosis had improved; Swelling gradually receded beginning on day 15, color improved, |

TABLE 27-continued

Therapeutic results for periodontal disease using the *Lactobacillus casei* species of the present invention

| Method | Patients Name | Age | Sex | Severity | Main patho-gens | Anti-biotic (abbrev) | Admin Period | Treatment progress and results |
|---|---|---|---|---|---|---|---|---|
| | | | | | | | | inside of pocket rose slightly, gums also tighter; Cure expected with continued treatment without extraction |

TABLE 28

Therapeutic results for periodontal disease using the *Lactobacillus casei* species of the present invention

| Method | Patients Name | Age | Sex | Severity | Main pathogens | Anti-biotic | Admin. Period | Treatment progress and results |
|---|---|---|---|---|---|---|---|---|
| C | O. M. | 60 | F | Shallow 3] [5 | *B. forsythus* *Ps. intermedia* | Amoxi-cillin (AMPC) for 5 days | 30 days | Little improvement during antibiotic admin period, rapid improvement after *lactobacillus* admin, gum color improved & swelling mostly gone by day 10 |
| | S. K. | 49 | F | Medium 2] 3] 4] | *Ps. gingivalis* | Cefaclor (CCL) for 5 days | 30 days | Slight improvement during antibiotic admin period, faster after *lactobacillus* administration, halitosis, drainage, bleeding stopped by day 10; periodontal pocket shrank to ½ volume by day 30 |
| | M. K. | 63 | M | Deep 5] 6] | *Ps. gingivalis* *Str. pyogenes* | Tetra-cycline (TC) for 7 days | 30 days | Little change during antibiotic admin period, gradual improvement after lactobacillus admin, swelling began to gradually recede by day 15, by day 30 teeth no longer loose and gums had regained elasticity, color extremely good; periodontal pocket shrank, cure expected |
| D | O. Y. | 72 | F | Shallow 5] | *A. actinomycetemcomituns* | | 60 days | Gradual improvement from day 7, pathogen gone by day 15; by day 60 slight periodontal pocket remained, complete cure expected with further admin of *L. bacillus* of invention |
| | K. Y. | 52 | M | Medium [5 [6 | *Ps. gingivalis* *Sta. aureus* | | 60 days | Began to improve from day 10, by day 15 halitosis gone and pathogen no longer evident; by day 30 gums were tight with better color; periodontal pocket also shrank, cure expected w/further treatment |
| | N. K. | 66 | F | Deep 3] 6] [3 [5 [6 | *Ps. gingivalis* *C. rectus* | | 60 days | Symptoms began to improve from day 15, pathogen not detected on day 21, drainage and bleeding stopped, could eat hard food; by day 60 flesh in periodontal pocket raised slightly, volume about ½; gum color and loose teeth improved, cure expected without extraction with further treatment |

Comparative Example 2

8 periodontal disease patients were divided into 4 groups A through D, 2 patients per group, and Group A was given antibiotics alone or together with an anti-inflammatory enzyme preparation depending on symptoms. In Group B, a preparation consisting of a mixture of equal amounts of freeze-dried bacterial cells of the original *Lactobacillus casei* species manufactured by the methods of Manufacturing Example 1 and a bacterial preparation manufactured by the methods of Manufacturing Example 3 (both antibiotic resistant) was administered together with an antibiotic. In Group C, an antibiotic or anti-inflammatory enzyme preparation was administered initially, followed by the aforementioned bacterial preparation. In Group D, no antibiotic was used from the beginning, and only the bacterial preparation was administered. This Comparative Example corresponds to Test Example 2 using periodontal patients (patients suffering from alveolar abscess and gingivitis) in Japanese Patent Application Laid-open No. 2001-333766, and the results are given in Table 29 (corresponding to part of Tables 7 through 10 in Japanese Patent Application Laid-open No. 2001-333766).

TABLE 29

Therapeutic results for periodontal disease using the original *Lactobacillus casei* species

| Method | Age | Sex | Disease | Main pathogens | Anti-biotics (abbrev) | Admin period | Treatment progress & results |
|---|---|---|---|---|---|---|---|
| A | 45 | M | Alveolar abscess ⌈7 | *Sta. aureus* *Str. pyogenes* | Cefaclor (CCL) | | Administered for 20 days with little improvement, no sign of a cure |
| | 27 | F | Gingi-vitis 5⌉⌈5 | *Bac. fragiris* *Sta. aureus* | Cefaclor (CCL) | | Slight improvement in symptoms beginning on day 7, but halitosis and swelling unchanged, symptoms better by day 21 but more effective treatment needed |
| B | 22 | F | Alveolar abscess ⌈8 | *Sta. aureus* *Str. pyogenes* | Cefaclor (CCL) | 45 days | Slight improvement in symptoms from day 7, halitosis mainly gone by day 30, gum color better; not cured by day 45 but symptoms better, complete cure expected with further treatment |
| | 62 | M | Alveolar abscess 7⌋⌊5 6⌉ | *Fuso. faciforme* *Sta. aureus* | Cefaclor (CCL) | 45 days | Symptoms began to improve from day 10, improving day by day, halitosis less & gum color much better by day 45, not cured but symptoms better, complete cure expected with further treatment |
| C | 72 | F | Alveolar abscess 6⌋ 5⌉⌈4 | *Bacte. melaminogenicus* *Str. pyogenes* | Amoxicillin (AMPC) | 45 days | Symptoms began to improve little by little from day 4, halitosis gone, gum color better by day 45; complete cure expected with further treatment |
| | 28 | F | Alveolar abscess ⌈7 | *Bacte. fragiris* *Sta. aureus* | Tetracycline (TC) | 60 days | Symptoms began to improve little by little from day 5, halitosis gone, gum color improved by day 60; complete cure expected with further treatment |
| D | 44 | F | Alveolar abscess 4⌋ | *Sta. aureus* | | 60 days | Symptoms began to improve little by little from day 10, halitosis gone, gum color improved by day 60; complete cure expected with further treatment |
| | 20 | M | Alveolar abscess 4⌋⌊5 | *Fuso. faciforme* *Str. pyogenes* | | 60 days | Symptoms began to improve on day 10, pathogen not detected by day 30, complete cure by day 60 |

Example 17

A treatment test was performed for the chronic infections chronic sinusitis, chronic bronchitis and bed sores. Group A was given antibiotics alone or together with an anti-inflammatory enzyme preparation depending on symptoms. In cases of chronic sinusitis, the sinuses were generally washed with an aqueous solution of a suspended antibiotic preparation, while in cases of bed sores an antibiotic preparation was applied to the affected area after cleansing. The results of treatment are shown in Table 30. In Group B, a preparation consisting of a mixture of equal amounts of the freeze-dried bacterial cells (FERM BP-10059, FERM P-19443) manufactured in Manufacturing Example 1 and the lactobacillus preparation (FERM BP-10059, FERM P-19443) manufactured in Manufacturing Example 3 was administered together with an antibiotic. In cases of chronic sinusitis, the basic method of administering the lactobacillus preparation was by nasal lavage using a suspension of 2 g of freeze-dried bacterial cells in 1 liter of warm water. In cases of bed sores, the freeze-dried cells were wiped or scattered on the bed sores. The results of treatment are shown in Table 31. In Group C, an antibiotic was administered initially, either alone or together with an anti-inflammatory enzyme preparation, followed by the aforementioned lactobacillus preparation. The results of treatment are shown in Table 32. In Group D, no antibiotic was used from the beginning, and only the lactobacillus preparation was administered. The results of treatment are shown in Table 33. For purposes of treatment the principal bacteria causing the chronic infections were isolated and tested for drug sensitivity, and the appropriate antibiotic was selected in each case based on the results. As can be seen from Tables 30 through 33, strong therapeutic effects were obtained using the lactobacillus preparation of the present invention for chronic infections that are hard to cure with antibiotics. Combined use of an antibiotic with the lactobacillus preparation of the present invention, which has antibiotic resistance, was particularly effective. The results were even better than those obtained with the original *Lactobacillus casei* species as described below.

TABLE 30

Therapeutic results for chronic infections using the *Lactobacillus casei* species of present invention

| Method | Age | Sex | Disease | Main pathogens | Antibiotics (abbrev.) | Drugs used | Treatment progress & results |
|---|---|---|---|---|---|---|---|
| A | 28 | M | Chronic sinusitis | *Str. pneumoniae* | Amoxicillin (AMPC) | | Condition improved immed. after nasal lavage, then regressed; little improvement after 10 days of admin., pathogen still detected |
| | 44 | F | Chronic sinusitis | *Str. pneumoniae* | Tetracycline (TC) | | Administered for 15 days with no sign of improvement |
| | 52 | F | Chronic bronchitis | *Sta. aureus* | Amoxicillin (AMPC) | | Cold symptoms improved somewhat beginning on day 5 of administration, but cough and sore throat unchanged, overall symptoms better after 2 weeks but more effective therapy needed; pathogen reduced but still detected |
| | 38 | M | Chronic bronchitis | *Bacte. caturahalis* | Tosufloxacin tosilate (TFLX) | | Same as above |
| | 77 | F | Bed sores (shallow) | *Kleb. pneumoniae* | Ofloxacin (OFLX) | | Affected area shrank by half with 2 weeks of application, but skin did not regenerate; skin finally regenerated after 1 month of admin. |
| | 74 | M | Bed sores (deep) | *Ps. aeruginosa* | Ofloxacin (OFLX) | | Some improvement with 2 weeks of application, but subsequent regression, improvement not achieved, continued pus and serum |

TABLE 31

Therapeutic results for chronic infections using antibiotics and *Lactobacillus casei* species of present invention

| Method | Age | Sex | Disease | Main pathogens | Antibiotics (abbrev.) | Drugs used | Treatment progress & results |
|---|---|---|---|---|---|---|---|
| B | 25 | F | Chronic sinusitis | *Str. pneumoniae* | Clarithromycin (CAM) | *Lactobacillus* prep. of invention | Improvement beginning on day 5, pathogen gone by day 15; few subjective symptoms by day 30, mainly cured as shown by pathology findings, x-ray |
| | 37 | M | Chronic sinusitis | *Str. pncumoniac Str. pyogenes* | Clarithromycin (CAM) | *Lactobacillus* prep. of invention | Rapid improvement from day 3, pathogen not detected by day 15, cure confirmed on day 30 from pathology findings, x-ray & subjective symptoms |

TABLE 31-continued

Therapeutic results for chronic infections using antibiotics and *Lactobacillus casei* species of present invention

| Method | Patients Age | Sex | Disease | Main pathogens | Antibiotics (abbrev.) | Drugs used | Treatment progress & results |
|---|---|---|---|---|---|---|---|
| | 48 | F | Chronic bronchitis | *Str. pneumoniae* | Ofloxacin (OFLX) | *Lactobacillus* prep. of invention | Symptoms began to improve from day 5, slight cough still present on day 30 but other cold symptoms mainly gone; pathogen not detected by day 7 |
| | 55 | M | Chronic bronchitis | *K. pneumoniae* | Tosufloxacin tosilate (TFLX) | *Lactobacillus* prep. of invention | Same as above |
| | 69 | M | Bed sores | *P. vulgaris* | Minocycline (MINO) | *Lactobacillus* prep. of invention | Affected area shrank by half with 1 week of application, skin regenerated after 2 weeks, secretions gone, improved |
| | 81 | F | Bed sores | *Str. pyogenes* | Amoxicillin (AMPC) | *Lactobacillus* prep. of invention | Granulation appeared with 1 week of application, rising with 2 weeks of application, affected area shrank by half in 3 weeks, complete skin regeneration in 4 weeks |

TABLE 32

Treatment results for chronic infections using *Lactobacillus casei* of the present invention

| Method | Patients Age | Sex | Disease | Main pathogens | Antibiotics (abbrev.) | Drugs used | Treatment progress & results |
|---|---|---|---|---|---|---|---|
| C | 33 | F | Chronic sinusitis | *Str. pneumoniae* | Clarithromycin (CAM) | *Lactobacillus* prep. of invention | Symptoms changed little during antibiotic admin (1 wk), improved rapidly after starting preparation, by day 30 there were few subjective symptoms and a cure was confirmed from tests |
| | 47 | F | Chronic sinusitis | *Sta. aureus* *Str. pneumoniae* | Clarithromycin (CAM) | *Lactobacillus* prep. of invention | Same as above |
| | 59 | M | Chronic bronchitis | *Str. pyogenes* *Kleb. pneumoniae* | Ofloxacin (OFLX) | *Lactobacillus* prep. of invention | Few effects seen during antibiotic admin (5 days), improvement beginning with use of preparation, cold symptoms better by day 15, mainly gone by day 30; pathogen not detected on day 12 |
| | 40 | M | Chronic bronchitis | *Str. pneumoniae* | Ofloxacin (OFLX) | *Lactobacillus* prep. of invention | Slight improvement in symptoms with antibiotic admin, rapid improvement with preparation, complete cure by day 30; pathogen gone by day 10 |
| | 65 | M | Bed sores (shallow) | *Enterococcus* | Tetracycline (TC) | *Lactobacillus* prep. of invention | Affected area shrank by half with 1 week of antibiotics; secretions decreased with application of preparation, thin skin regenerated after 1 week |
| | 68 | F | Bed sores (deep) | *Str. pyogenes* | Minocycline (MINO) | *Lactobacillus* prep. of invention | Flesh thickened slightly with 2 weeks of antibiotic use, but affected area unchanged; area shrank by 1/2 with 1 week of application of preparation, secretions gradually declined, sores mainly closed within 4 weeks, thin skin overall |

TABLE 33

Treatment results for chronic infections using *Lactobacillus casei* of the present invention

| Method | Patients Age | Sex | Disease | Main pathogens | Antibiotics (abbrev.) | Drugs used | Treatment progress & results |
|---|---|---|---|---|---|---|---|
| D | 22 | M | Chronic sinusitis | Sta. *aureus* | | Lactobacillus prep. of invention | Gradual improvement from about day 5, pathogen not detected on day 30, almost cured by day 50 according to pathological findings and x-ray |
| | 42 | M | Chronic sinusitis | Str. *pneumoniae* | | Lactobacillus prep. of invention | Same as above |
| | 65 | F | Chronic bronchitis | Kleb. *pneumoniae* | | Lactobacillus prep. of invention | Symptoms improved from day 5, symptoms mainly gone by day 50, judged recovered |
| | 56 | M | Chronic bronchitis | Str. *pneumoniae* Str. *aguluctiae* | | Lactobacillus prep. of invention | Same as above |
| | 73 | M | Bed sores (shallow) | Ps. *aeruginosa* | | Lactobacillus prep. of invention | Affected area shrank by roughly 1/2 with 2 weeks' application, secretions declined gradually with further application, thin skin regenerated in 3 wks |
| | 78 | F | Bed sores (deep) | Enterococcus Sta. *aureus* | | Lactobacillus prep. of invention | Some granulation after 1 week of application, followed by rapid raising of flesh, thin skin formed in 4 weeks; skin now beautiful with no scars |

Comparative Example 3

8 chronic sinusitis patients and 8 chronic bronchitis patients were each divided into 4 groups A through D, two people per group, and the A group was given an antibiotic alone or together with an anti-inflammatory enzyme preparation depending on symptoms. In Group B, a preparation consisting of a mixture of equal amounts of freeze-dried bacterial cells of the original *Lactobacillus casei* species manufactured by the methods of Manufacturing Example 1 and a lactobacillus preparation manufactured by the methods of Manufacturing Example 3 was administered together with an antibiotic. In Group C, an antibiotic was administered initially either alone or together with an anti-inflammatory enzyme preparation, followed by the aforementioned lactobacillus preparation. In Group D, no antibiotic was used from the beginning, and only the lactobacillus preparation was administered. This Comparative Example corresponds to Test Example 2 for chronic sinusitis and chronic bronchitis in Japanese Patent Application Laid-open No. 2001-333766, and the results are given in Tables 34 and 35 (corresponding to part of Tables 7 through 10 in Japanese Patent Application Laid-open No. 2001-333766).

TABLE 34

Treatment effects for chronic infections using original *Lactobacillus casei* species

| Method | Patients Age | Sex | Disease | Main pathogens | Antibiotics (abbrev.) | Admin period | Treatment progress & results |
|---|---|---|---|---|---|---|---|
| A | 18 | F | Chronic sinusitis | Str. *pneumoniae* | Ampicillin (ABPC) | | Subjective symptoms unchanged, but pathology findings & x-ray somewhat better from day 10 of administration; symptoms began to get worse on day 20 |
| | 20 | M | Chronic sinusitis | Str. *pneumoniae* Sta. *aureus* | Clarithromycin (CAM) | | Administered for 20 days with no improvement, no signs of recovery |
| | 62 | M | Chronic bronchitis | Sta. *aureus* Kleb. *pneumoni* | Ofloxacin (OFLX) | | Cold symptoms much improved beginning on day 5 of admin, but sore throat and cough persisted; symptoms better on day 21, but more effective treatment thought necessary |
| | 50 | F | Chronic bronchitis | Sta. *aureus* Sta. *pneumoniae* | Ofloxacin (OFLX) | | Same as above |
| B | 18 | F | Chronic sinusitis | Str. *pneumoniae* | Clarithromycin (CAM) | 45 days | Symptoms improved rapidly from day 7 of admin, pathogen not detected on day 30; cure confirmed on day 45 from pathology findings, x-ray, subjective symptoms |
| | 35 | M | Chronic sinusitis | Str. *pneumoniae* Str. *pyogenes* | Clarithromycin (CAM) | 45 days | Symptoms improved rapidly from day 4, almost cured by day 45 according to pathology findings & x-ray, but subjective symptoms still present; |

TABLE 34-continued

Treatment effects for chronic infections using original *Lactobacillus casei* species

| Method | Patients Age | Sex | Disease | Main pathogens | Antibiotics (abbrev.) | Admin period | Treatment progress & results |
|---|---|---|---|---|---|---|---|
| | 45 | F | Chronic bronchitis | Bran. catarihalis Sta. aureus | Ofloxacin (OFLX) | 45 days | complete cure expected w/further treatment Symptoms improved bit by bit from day 7, throat still sore by day 45 but other cold symptoms better, complete cure expected with further administration |
| | 72 | F | Chronic bronchitis | Str. pneumoniae | Ofloxacin (OFLX) | 45 days | Symptoms began to improve from day 7, complete cure confirmed on day 45 |

TABLE 35

Treatment results for chronic infections using original *Lactobacillus casei* species

| Method | Patients Age | Sex | Disease | Main pathogens | Antibiotics | Admin period | Treatment progress & results |
|---|---|---|---|---|---|---|---|
| C | 33 | F | Chronic sinusitis | Str. pneumoniae | Clarithromycin (CAM) | 60 days | Gradual improvement in symptoms from day 5, pathogen not detected by day 40; pathology and x-ray findings much better by day 60, subjective symptoms improved, completed cure expected with further treatment |
| | 45 | M | Chronic sinusitis | Str. pneumoniae Sta. aureus | Clarithromycin (CAM) | 60 days | Symptoms began to improve on day 3, improving day by day, remission according to pathology and x-ray on day 60, subjective symptoms gone, complete cure expected with further administration |
| | 47 | M | Chronic bronchitis | Str. pneumoniae | Ofloxacin (OFLX) | 60 days | Symptoms improved gradually from day 5, cold symptoms except cough gone by day 60, complete cure expected with further administration |
| | 52 | F | Chronic bronchitis | Bran. catarrhalis | Ofloxacin (OFLX) | 60 days | Symptoms improved gradually from day 7, cold symptoms except cough gone by day 60; completed cure expected with further administration |
| D | 39 | M | Chronic sinusitis | Str. pneumoniae | | 60 days | Symptoms improved gradually from day 5, remission on day 60 according to pathology and x-ray findings, few subjective symptoms; complete cure expected with further admin |
| | 48 | M | Chronic sinusitis | Str. pneumoniae | | 60 days | Symptoms improved rapidly from day 10, complete cure by day 60 |
| | 62 | F | Chronic bronchitis | Sta. aureus Kleb. pneumoniae | | 60 days | Symptoms began to improve from day 7, mainly gone by day 60, recovered; completed cure expected with further admin |
| | 68 | F | Chronic bronchitis | Str. pneumoniae | | 60 days | Same as above |

Example 18

20 g of a freeze-dried bacterial cell preparation (FERM BP-6971) manufactured by the methods of Manufacturing Example 2 mixed with 100 g of lactose was administered 2 g per day to patients suffering from chronic conditions which were not infections, including constipation, diarrhea, diabetes, a non-infectious disorder, chronic fatigue syndrome, atopic dermatitis, low blood pressure, neurosis and high blood pressure. The administered dose of bacteria was 2 g/day at $1\times10^{10}$ cells/g. In a treatment test of the lactobacillus preparation of the present invention (FERM BP-10059, FERM P-19443), the preparation was administered for 2 months to 10 patients each suffering from the same or similar symptoms, and the average improvement is shown in Table 36. About 15% of patients exhibited no improvement in symptoms even after receiving the lactobacillus preparation of the present invention, but in no case did the symptoms get worse. Effectiveness was also demonstrated to various degrees for many chronic conditions other than those shown in Table 36, including arteriosclerosis, gout, obesity and chronic hepatitis. As is clear from Table 36, if the effects of the *lactobacillus* preparation are achieved 100% without interference, the body's natural healing power is enhanced, and vitality is restored. For example, if the intestines are cleansed by internal administration, the blood is naturally cleansed so that hormones, enzymes, antibodies, immune substances and other essential substances are carried freely throughout the body, making metabolism smoother, improving systemic functions and allowing for a life untroubled by sickness. In truth, Metchinikoff's "prolongation of life" thesis has finally been realized after a century.

TABLE 36

Progress of chronic conditions

Progress of symptoms after administration of *lactobacillus* preparation of present invention

| Chronic conditions | Results after 2 months[1] | Progress |
|---|---|---|
| Constipation | ○~◎ | Symptoms began to improve from day 3 of administration, improving day by day, largely gone by day 15, good condition |
| Diarrhea | ◎ | Diarrhea better from day 2, mainly gone by day 10; condition continued to improve, much better after 1 month |
| Diabetes | ○ | Mean blood sugar level of 185 mg/dl fell to 150 after 1 month of administration and to 140 mg/dl after 2 months |
| Non-infectious condition | Δ~○ | Began to improve gradually after about a month, with gradual improvement thereafter, no longer a problem after 2 months |
| Chronic fatigue syndrome | ◎ | Fatigue gradually improved from about day 7, mainly gone after 1 month |
| Atopic dermatitis | Δ~○ | Atopic symptoms which had persisted for years gradually improved from about day 15, much better after 2 months |
| Low blood pressure | ◎ | Began to rise from about day 6 (55 to 95 mmHg), to (60 to 100 mmHg) after a month, returning to normal (65 to 110 mmHg) after 2 months |
| Neurosis | Δ | Anxiety, obsession, fear, hysteria and other symptoms began to improve after about a month of administration, leading to remission; these nervous symptoms were not much of a concern after 2 months |
| High blood pressure | Δ~○ | Blood pressure (max. 175 mmHg) began to fall from about day 15, reaching 150 mmHg after 1 month; improved further with combined use of blood pressure lowering medication |

[1] Treatment results

◎ Great improvement, health restored or nearly restored

○ Health not completely restored, but condition improved, complete cure expected with continued administration of preparation Δ Some improvement, other more effective treatment needed As shown in Example 16, good effects are achieved through suitable administration of this lactobacillus in the treatment of periodontal disease, but unfortunately this could not be called a cure depending on the progress of the periodontal disease. Consequently, the inventors showed as a result of exhaustive research that the effects could be improved through the application of the features of the bactericidal disinfectant as a pre-treatment, with the results explained below.

Example 19

The affected areas of 5 patients suffering from shallow periodontal disease were washed with "this bactericidal disinfectant," and then treated by injection of the "novel lactobacillus preparation" manufactured in Manufacturing Example 4 into the affected area. The results are shown in Table 37.

TABLE 37

Results of treatment of shallow periodontal disease by a combination of disinfection with "this bactericidal disinfectant" and the "novel *lactobacillus* preparation" of the present invention ("novel *lactobacillus* preparation" used as *lactobacillus* preparation)

| Patients | | | | Main | |
|---|---|---|---|---|---|
| Name | Age | Sex | Site | pathogens | Progress & results |
| T. K. | 58 | M | ⌈3 5⌉ | *P. gingivalis* *B. forsythus* | Gradual improvement from day 3 of admin, gum swelling and color much better by day 7, gums mainly closed by day 20, almost cured by day 30 |
| K. M. | 54 | F | ⌊4 | *P. gingivalis* *F. nucleatum* | Halitosis gone by day 2, pathogen by day 5, gum swelling by day 7, pocket almost closed by day 15, cured by day 30 |
| T. M. | 48 | M | ⌊2 ⌊6 | *P. gingivalis* | Swelling subsided day after administration, gum color, elasticity better by day 3; gum in pocket risen and closed by day 10, almost cured by day 25 |
| S. Y. | 70 | M | ⌈5 | *P. intermedia* *S. aureus* | Gradual improvement from day 5, halitosis better; gums began to regain elasticity on day 10, pocket somewhat closed by day 21, mostly closed by day 30 |
| H. K. | 36 | F | ⌊3 ⌈3 | *A. actino* *S. aureus* | Pathogen gone by day 3, pocket shallower by day 7, mostly closed by day 15; gum condition improved, mostly cured by day 25 |

Example 20

Five patients suffering from shallow periodontal disease were treated by first disinfecting the affected areas with "the bactericidal disinfectant," and then injecting a "novel lactobacillus preparation containing antibiotics" manufactured according to Manufacturing Example 5 into the affected areas. The results are shown in Table 38.

TABLE 38

Table 38. Results of treatment of shallow periodontal disease by a combination of disinfection with "this bactericidal disinfectant" and the "novel *lactobacillus* preparation" of the present invention ("novel *lactobacillus* preparation containing antibiotics" used as *lactobacillus* preparation)

| Patients | | | | Main | |
|---|---|---|---|---|---|
| Name | Age | Sex | Site | pathogens | Progress & results |
| O. N. | 39 | M | ⌈6 ⌊7 | *P. gingivalis* *C. rectus* | Swelling subsided, halitosis gone by day 2; pathogen gone by day 3, gum color, elasticity recovered by day 7; pocket shallower on day 10, mainly closed by day 15 |
| S. N. | 56 | F | ⌈4 ⌈5 | *A. actino* | Gradual improvement from day 3, gum condition mostly recovered by day 5; pocket somewhat shallower, mainly closed by day 12, almost cured by day 20 |
| H. M. | 65 | F | ⌈4 ⌊3 | *A. actino* *S. aureus* | Improvement from about day 5; rapid improvement from about day 10, gum elasticity, color, swelling almost cured; gums in pocket risen, mostly closed by day 18 |
| I. T. | 67 | M | ⌈6 | *P. intermedia* *A. actino* | Pathogen, halitosis gone on day after administration; slight drainage gone by day 3, gums in pocket risen by day 15, mainly closed by day 25, complete recovery |
| M. M. | 62 | M | ⌈5 ⌈6 | *P. gingivalis* *B. forsythus* | Rapid improvement from day 3, gum color and elasticity restored by day 5; pocket shallower, closed by day 20 for complete cure |

Comparative Example 4

As a comparison, 5 patients each suffering from periodontal disease were treated with "this bactericidal disinfectant," with the "novel lactobacillus preparation" manufactured in Manufacturing Example 4, with the "novel lactobacillus preparation containing antibiotics" manufactured in Manufacturing Example 5 and with conventional therapy. The results are shown in Table 39.

TABLE 39

Treatment results for shallow periodontal disease using conventional therapy

| | Average treatment progress and results for 5 patients |
|---|---|
| "This bactericidal disinfectant" alone | Pathogen gone by day 3, but little improvement in swelling, color, elasticity of gums; periodontal pockets shallower, but did not close completely; cure not achieved in 2 months |
| "Novel lactobacillus preparation" alone | Gradual improvement after several days of administration, halitosis gone; gum color, swelling, elasticity improved by day 15; periodontal pockets mainly closed by day 30, almost cured by day 60 |
| Conventional therapy | Swelling subsided by day 15 of therapy, but swelling and elasticity still unsatisfactory; pockets somewhat shallower by day 30, but did not close with further treatment; however, gum color and elasticity recovered |
| "Novel lactobacillus preparation containing antibiotics" alone | Gradually improved after several days of administration, gum color, elasticity, swelling generally recovered by day 10; gum pockets shallower by day 21, gums risen by day 30, mainly closed by day 45 |

When the periodontal disease was shallow, gum color, swelling and elasticity recovered within 2 to 3 weeks with conventional therapy and the pockets grew shallower but never closed. By contrast, when disinfection with "this bactericidal disinfectant" was combined with the "novel lactobacillus preparation" of the present invention, improvement was rapid from the beginning of treatment, swelling subsided rapidly, gum color and elasticity recovered greatly in about 2 weeks and the pockets gradually grew shallower, closing within about a month for a complete cure.

Example 21

Five patients suffering from intermediate periodontal disease were treated by first disinfecting the affected areas with "this bactericidal disinfectant" and then injecting the "novel lactobacillus preparation" manufactured in Manufacturing Example 4. The results are shown in Table 40.

TABLE 40

Results of treatment of intermediate periodontal disease by a combination of disinfection with "this bactericidal disinfectant" and the "novel *lactobacillus* preparation" of the present invention ("novel *lactobacillus* preparation" used as *lactobacillus* preparation)

| Patients | | | | Main | |
|---|---|---|---|---|---|
| Name | Age | Sex | Site | pathogens | Progress & results |
| K.Y. | 50 | F | [2 6] | *P. intermedia* *Str. pyogenes* | Improvement beginning around day 5; halitosis and pathogen disappeared, gum swelling gone by day 15, color and elasticity normal; pockets gradually shrank, mainly closed by day 45; cured by day 60 |
| O.K. | 75 | F | [2 2] | *P. gingivalis* *Fusobacterium* | Gradual improvement from day 10, halitosis gone; gum swelling, elasticity, color much improved by day 20; gums in pockets rose bit by bit, much shallower by day 60, mainly closed by day 90 |
| Y.T. | 68 | M | [4 5] | *P. gingivalis* *B. forsythus* | Drainage stopped by day 5, halitosis & pathogen gone; gum color, elasticity much better by day 10, pocket somewhat shallower; gums tighter by day 20, mainly closed by day 35 |
| W.S. | 60 | M | [2 4] | *P. gingivalis* | Rapid improvement from day 7; gums are firm; drainage, bleeding, halitosis stopped; pocket shrank and closed by day 21 and cured |
| T.T | 44 | M | 3] [3 | *A. actino* *P. intermedia* | Gradual improvement from day 5, gum elasticity began to return from day 10, color pink by day 15, pocket gradually grew shallower, mainly closed by day 42 |

Example 22

Five patients suffering from intermediate periodontal disease were treated by first disinfecting the affected areas with "this bactericidal disinfectant," and then injecting the "novel lactobacillus preparation containing antibiotics" manufactured in Manufacturing Example 5. The results are shown in Table 41.

TABLE 41

Results of treatment of intermediate periodontal disease by a combination of disinfection with "this bactericidal disinfectant" and the "novel *lactobacillus* preparation" of the present invention ("novel *lactobacillus* preparation containing antibiotics" used as *lactobacillus* preparation)

| Patients | | | | | |
|---|---|---|---|---|---|
| Name | Age | Sex | Site | Main pathogens | Progress & results |
| U.M. | 36 | M | ⌊2 ⌊3 ⌈5 | *P. gingivalis* *S. aureus* | Improvement beginning on day 3, halitosis, pathogen, swelling gone; gum color, elasticity restored by day 12; bleeding, drainage stopped on day 5; pocket gradually shrank from about day 15, mainly closed by day 35 |
| E.J. | 55 | F | ⌊5 | *P. intermedia* *A. actimo* | Rapid improvement from day 7, halitosis, bleeding, drainage stopped; gum color, elasticity, swelling recovered by day 14, gums rose in pocket, completely closed by day 40 |
| K.I. | 65 | F | ⌈3 ⌊2 | *Fusobacterium* *E. corrodens* | Began to improve day after first administration; halitosis, bleeding, drainage stopped by day 3; gum condition almost cured by day 7; pocket shrank gradually and almost closed by day 35 |
| S.S. | 72 | F | 4⌉5⌉ | *W. recta* *B. forsythus* | Rapid improvement from day 5; gum condition almost cured by day 10 but pocket in gums still not risen satisfactorily and took 48 days to close completely |
| H.M. | 59 | M | ⌊6 ⌊5 | *P. gingivalis* | Halitosis, pathogen gone by day 3; drainage, bleeding stopped by day 7; gum condition gradually improved from day 15, mainly cured by day 28; pocket never closed completely, but almost cured |

Comparative Example 5

As a comparison, 5 patients each with intermediate periodontal disease were treated with "this bactericidal disinfectant," the "novel lactobacillus preparation" manufactured in Manufacturing Example 4, the "novel lactobacillus preparation containing antibiotics" manufactured in Manufacturing Example 5 and conventional therapy. The results are shown in Table 42.

TABLE 42

Treatment results for intermediate periodontal disease using conventional therapy

| | Average treatment progress and results for 5 patients |
|---|---|
| "This bactericidal disinfectant" alone | Pathogen gone by day 3, drainage, bleeding gone by day 5 with gradual but steady recovery of gum swelling, color, elasticity; pockets shrank but did not close |
| "Novel *lactobacillus* preparation" alone | Pathogen gone by day 3, halitosis, drainage, bleeding mainly subsided by day 5, with gradual recovery of gum color, swelling, elasticity; pockets shrank gradually, mainly closed after 3 months of administration but did not close completely |
| Conventional therapy | Swelling subsided by day 15 of therapy, but color and elasticity did not recover, |

TABLE 42-continued

Treatment results for intermediate periodontal disease using conventional therapy

| | Average treatment progress and results for 5 patients |
|---|---|
| "Novel lactobacillus preparation containing antibiotics" alone | little change; pockets shrank very little; status quo barely maintained Began to improve from about day 10, halitosis, pathogen gone by day 15; gum color recovering by day 30, elasticity also better; pockets shrank somewhat, but did not close completely even with further treatment |

When the periodontal disease was intermediate, swelling subsided but color and elasticity were still unsatisfactory with conventional therapy, and while the pockets grew somewhat shallower and narrower, the change was not great. By contrast, when disinfection with "this bactericidal disinfectant" was combined with the "novel lactobacillus preparation" of the present invention, although progress towards a cure was slower than in the case of shallow periodontal disease, there was definite improvement and almost a complete cure within 2 to 3 months.

Example 23

Five patients suffering from deep periodontal disease were treated by first disinfecting the affected areas with "this bactericidal disinfectant" and then injecting the "novel lactobacillus preparation" manufactured in Manufacturing Example 4. The results are shown in Table 43.

TABLE 43

Results of treatment of deep periodontal disease by a combination of disinfection with "this bactericidal disinfectant" and the "novel *lactobacillus* preparation" of the present invention ("novel *lactobacillus* preparation" used as *lactobacillus* preparation)

| Patients | | | | Main | |
|---|---|---|---|---|---|
| Name | Age | Sex | Site | pathogens | Progress & results |
| W. I. | 54 | F | ⌊6 ⌈2 | P. gingivalis E. corrodens | Halitosis, pathogen gone by day 3; bleeding, drainage better from about day 7; gum condition improved from about day 15, improvement in swelling and elasticity; gums in pockets gradually rose, pockets shallower |
| M. N. | 64 | M | ⌈5 ⌈6 | P. intermedia | Rapid recovery from about day 5, bleeding, drainage gone by day 10; gum condition improved, elasticity recovered by day 30, gums in pocket began to rise, shallower by day 45, mainly closed by day 60 |
| N. M. | 70 | F | ⌊3 ⌊4 | A. actino P. inermedia | Gradual improvement from day 7, halitosis, bleeding, drainage gone by day 15; gum color, swelling, elasticity improved rapidly from around day 30; pockets began to gradually grow shallower, mainly closed by day 60 |
| O. S. | 42 | M | 2⌋ ⌊5 | P. gingivalis | Gradual recovery from about day 5, bleeding, drainage, swelling gone by day 7; gums began to improve, color, elasticity back to normal by day 20; periodontal pockets gradually shrank, mainly closed by day 60 |
| S. I. | 48 | M | ⌈6 3⌋ | P. gingivalis B. forsythus | Halitosis, pathogen gone by day 3; swelling subsided by day 7; bleeding, drainage stopped, gum color, elasticity almost normal by day 15; gum in pocket rose gradually, shallower by day 45, mainly closed by day 65 |

Example 24

Five patients suffering from deep periodontal disease were treated by first disinfecting the affected areas with "this bactericidal disinfectant," and then injecting the "novel lactobacillus preparation containing antibiotics" manufactured in Manufacturing Example 5. The results are shown in Table 44.

TABLE 44

Results of treatment of deep periodontal disease by a combination of disinfection with "this bactericidal disinfectant" and the "novel *lactobacillus* preparation" of the present invention ("novel *lactobacillus* preparation containing antibiotics" used as *lactobacillus* preparation)

| Patients | | | Main | | |
|---|---|---|---|---|---|
| Name | Age | Sex | Site | pathogens | Progress & results |
| U. M. | 77 | M | ⌈3 ⌈4 ⌈5 | P. intermedia P. gingivalis | Pathogen gone by day 3; bleeding, drainage gone by day 5; gum condition better from about day 12, elasticity recovered; pocket gradually shranks, mainly closed by day 50 |
| T. K. | 80 | F | ⌊4 ⌊5 ⌊6 | P. gingivalis S. aureus S. pyogenes | Halitosis, pathogen gone by day 3; bleeding, drainage gone by day 7, swelling improved; gum elasticity better from about day 15, color recovered; gums in pocket gradually rose, pocket shrank but did not close |
| A. S. | 65 | F | ⌈2 ⌊4 | P. gingivalis Fusobucterium | Recovery from day 4, bleeding, drainage gone by day 7; gum condition (color, elasticity) much better from about day 15, pocket gradually shrank, mainly closed by day 60 |
| S. A. | 47 | M | 6⌋ ⌊3 | A. actino Fusobucterimum | Halitosis, pathogen gone by day 3; swelling better by day 5, color, elasticity mostly recovered by day 15; periodontal pocket shrank rapidly, to a few mm by day 30, and was almost closed by day 50 |
| T. T. | 50 | M | ⌈5 5⌉ | P. intermedia B. forsythus | Halitosis, pathogen gone by day 3; bleeding, drainage gone by day 5; gum color, elasticity better by day 15, completely recovered by day 30; pocket gradually shrank, almost completely closed by day 60 |

Comparative Example 6

As a comparison, 5 patients each with deep periodontal disease were treated with "this bactericidal disinfectant," the "novel lactobacillus preparation" manufactured in Manufacturing Example 4, the "novel lactobacillus preparation containing antibiotics" manufactured in Manufacturing Example 5 and conventional therapy. The results are shown in Table 45.

TABLE 45

Treatment results for deep periodontal disease using conventional therapy

| | Average treatment progress and results for 5 patients |
|---|---|
| "This bactericidal disinfectant" alone | Pathogen and halitosis gone within a few days, gum swelling, color, elasticity improved gradually but not satisfactorily; pockets felt shallower but little change in actual depth |
| "Novel lactobacillus preparation" alone | Pathogen gone by day 5-7, symptoms began to improve from day 7, bleeding, drainage better by day 10, swelling began to subside from about day 15, gums tighter; color improved, gums in pockets rose, pockets grew shallower but did not recover completely |
| Conventional therapy | Little improvement, status quo barely maintained; however, gum swelling and elasticity recovered slightly, halitosis also better |

TABLE 45-continued

Treatment results for deep periodontal disease using conventional therapy

| | Average treatment progress and results for 5 patients |
|---|---|
| "Novel *lactobacillus* preparation containing antibiotics" alone | Pathogen gone by day 5 of administration, with improved symptoms, bleeding, drainage gone; gum condition improved from day 15, mainly recovered by day 25; pockets grew gradually shallower but did not disappear |

When the inflammation was deep, swelling, color, elasticity and other gum symptoms recovered slightly with conventional therapy, but the pockets were virtually unchanged, and the status quo was barely maintained. By contrast, when disinfection with "this bactericidal disinfectant" was combined with the "novel lactobacillus preparation" of the present invention, the gums began to improve after about 2 weeks of therapy with individual differences, and health was mainly restored in about 2 months. The pockets shrank slowly but steadily, to a few mm in about 3 months. Some patients remained in the same condition, while in other cases the pockets eventually closed for a complete cure.

Example 25

Five patients suffering from end-stage periodontal disease were treated by first disinfecting the affected areas with "this bactericidal disinfectant" and then injecting the "novel lactobacillus preparation" manufactured in Manufacturing Example 4. The results are shown in Table 46.

TABLE 46

Results of treatment of end-stage periodontal disease by a combination of disinfection with "this bactericidal disinfectant" and the "novel *lactobacillus* preparation" of the present invention ("novel *lactobacillus* preparation" used as *lactobacillus* preparation)

| Patients | | | | Main | |
|---|---|---|---|---|---|
| Name | Age | Sex | Site | pathogens | Progress & results |
| H. M. | 64 | M | 3⌉ 4⌉ | *P. gingivalis* *A. actino* | Pathogen, halitosis gone by day 4, bleeding, swelling by day 7; gum condition improved from day 15, teeth less wobbly; gum tissue began to regenerate gradually on day 60, pocket shrank; gum appearance improved, teeth no longer wobbly by day 120, gums largely recovered; pockets mainly closed by day 180, complete cure |
| K. N. | 67 | F | ⌊4 6⌋ ⌈2 | *P. gingivalis* *Fusobacterium* | Progress similar to above, almost cured |
| N. T. | 72 | F | 2⌉ 3⌉ 4⌉ | *P. gingivalis* *P. intremedia* | Pathogen, halitosis gone by day 5, but bleeding and drainage continued through day 10; gums somewhat improved by day 30, but loose teeth and pocket depth unchanged; some improvement after 90 days of treatment, but ended with extraction |
| N. M. | 59 | M | ⌊6 | *P. gingivalis* | Halitosis, pathogen gone by day 3, bleeding stopped by day 5; drainage stopped on day 7; gum color, elasticity began to recover from day 15; tooth looseness somewhat better from about day 25, no longer loose by day 60; 27 mm periodontal pocket shrank, to 15 mm by day 90; by day 120 gum condition had returned to normal, periodontal pocket was 12 mm, 4 mm by day 180, almost complete cure. Considerable regeneration of alveolar bone |
| K. K. | 63 | M | ⌊5 ⌊6 | *P. gingivalis* *B. forsythus* *E. corrodens* | Progress somewhat slower than above but similar, cured in 9 months |

Example 26

Five patients suffering from end-stage periodontal disease were treated by first disinfecting the affected areas with "this bactericidal disinfectant" and then injecting the "novel lactobacillus preparation containing antibiotics" manufactured in Manufacturing Example 5. The results are shown in Table 47.

TABLE 47

Results of treatment of end-stage periodontal disease by a combination of disinfection with "this bactericidal disinfectant" and the "novel *lactobacillus* preparation" of the present invention ("novel *lactobacillus* preparation containing antibiotics" used as *lactobacillus* preparation)

| Patients | | | | Main | |
|---|---|---|---|---|---|
| Name | Age | Sex | Site | pathogens | Progress & results |
| Y. M. | 77 | M | ⌊2 3⌋ | *A. actino* *Fusobacterium* | Pathogens, halitosis gone by day 3, bleeding, drainage by day 5; gum condition improved by day 10, tooth looseness slightly better; alveolar bone somewhat restored by day 30; pockets shrank gradually, to 10 mm by day 60; gums recovered by day 120, pocket depth about 5 mm; cure expected with further treatment |
| W. T. | 58 | F | ⌊3 ⌊4 ⌊5 | *P. gingivalis* *W. recta* | Same trend as above |
| V. M. | 69 | M | ⌈5 5⌉ | *P. gingivalis* *W. recta* | Pathogens, halitosis gone by day 4, bleeding, drainage by day 7; gum color, elasticity, swelling improved from day 12, almost recovered by day 30; pockets gradually shrank, to less than 10 mm by day 80; loose teeth better by day 60, could eat hard food; mainly cured by day 150 |
| E. M. | 64 | F | ⌊3 ⌊5 | *A. actino* *W. recta* | Similar to above, although somewhat slower |
| H. T. | 50 | F | ⌈6 5⌉ | *P. gingivalis* *A. actino* *P. intermedia* | Pathogens gone by day 5, gum color, elasticity, etc. somewhat improved by day 20, but little change in alveolar bone, loose teeth improved slightly but were ultimately extracted |

Comparative Example 7

Five end-stage periodontal disease patients were treated with guided tissue regeneration using Emdogain, which has attracted interest as a cutting-edge existing therapy. The results are shown in Table 48.

TABLE 48

Treatment results for end-stage periodontal disease using guided tissue regeneration

| | Average treatment progress and results for 5 patients |
|---|---|
| Guided tissue regeneration | A new system of treatment was attempted but with no improvement, and the teeth had to be extracted |

When the periodontal disease was end-stage, it seemed to be too late for conventional therapy, and finally the teeth had to be extracted. Although the teeth could be supported surgically without being pulled, the disease then re-occurred, and in many cases extraction was only delayed. By contrast, with a combination of "the bactericidal disinfectant" and the "novel lactobacillus preparation" of the present invention it was possible to eliminate the pathogens and remove causative factors, producing a synergistic effect which led to tissue regeneration so that in 70 to 80% of cases extraction was unnecessary and the teeth were saved even if a complete cure was not achieved.

Example 27

Two-month-old Landrace piglets with an average weight of 18 kg were divided into 3 groups of 10 male and 10 female piglets per group, and reared in individual, windowless pig houses ventilated by fans. The feed was standard pig feed (Nosan Corporation), supplied with feed always available in the feed bin, and water was supplied automatically through a water cup. The control group was given feed prepared with the original *Lactobacillus casei* (FERM BP-6971) while the test group was given feed prepared with the *Lactobacillus casei* of the present invention manufactured in Manufacturing Example 3 (FERM BP-10059, FERM P-19443), $1 \times 10^6$ wet cells/g of feed in each case, and no lactobacillus was given to the untreated group. After being reared for 1 month under these rearing conditions, as shown in Table 49 the piglets in the test group receiving the *Lactobacillus casei* of the present invention had better coats than those in the untreated group, and were an average of 4.8 kg heavier, indicating an obvious growth promotion effect. There were no signs of diarrhea or other symptoms common in piglets, and they showed no signs of illness after the test. There was also less fecal odor. Good results were also obtained in the control group, which was treated with the original *Lactobacillus casei* species, but to a lesser extent that in the test group. In a meat texture test by a specialist the quality in the test group was evaluated as extremely good, with a large amount of red meat and an elastic texture.

TABLE 49

Piglet feeding trial results

|  | Untreated group | Control group | Test group |
| --- | --- | --- | --- |
| Initial mean body weight | 18.2 kg | 18.0 kg | 17.8 kg |
| Mean weight after 1 week | 21.2 kg | 21.0 kg | 21.4 kg |
| Mean weight after 2 weeks | 25.5 kg | 26.1 kg | 26.9 kg |
| Mean weight after 3 weeks | 31.3 kg | 32.5 kg | 34.0 kg |
| Mean weight after 4 weeks | 38.8 kg | 40.2 kg | 43.2 kg |
| Mean weight gain | 20.6 kg | 22.2 kg | 25.4 kg |
| Feed intake | 42.2 kg | 43.8 kg | 43.7 kg |
| Required Feed Ratio | 2.05 | 1.97 | 1.72 |

Example 28

30 male and 30 female newborn chicks (mean weight 43 g) of a specialized broiler variety (Arbor Acre) were pre-reared for 3 days and divided into three groups with equal numbers of males and females in each group, and there was confirmed to be no variation in body weight with a mean weight of 50 g in each group. These were fed with standard starter feed for broiler fattening (Kyodo Shiryo, Golden G) for 4 weeks. Rearing was in crates until 4 weeks of age (insulated temperature 35° C.±2° C.). The control group was given freeze-dried cells of the original *Lactobacillus casei* species (FERM BP-6971) and the test group was given freeze-dried cells of the *Lactobacillus casei* species of the present invention manufactured in Manufacturing Example 3 (FERM BP-10059, FERM P-19443) mixed with standard feed to $2 \times 10^7$ cells/g of feed in each case. The untreated group was given no lactobacillus. Water was supplied freely through a water feeder, while feed was supplied continuously with feed always available in the feed bin. The results are shown in Table 50, and it shows clearly that as a result of rearing for 4 weeks the control group exhibited about 15% and the test group about 27% greater weight gain than the untreated group. No sickness occurred in the test group during the rearing period, with no diarrhea symptoms and a reduction in fecal odor. This is further evidence that the effects of a lactobacillus preparation using the *Lactobacillus casei* species of the present invention are much better than those of a lactobacillus preparation using the original *Lactobacillus casei* species.

TABLE 50

Broiler feeding trial results

|  | Untreated group | Control group | Test group |
| --- | --- | --- | --- |
| Initial mean body weight | 50.5 g | 50.0 g | 49.5 g |
| Mean weight after 1 week | 162 g | 173 g | 180 g |

TABLE 50-continued

Broiler feeding trial results

|  | Untreated group | Control group | Test group |
| --- | --- | --- | --- |
| Mean weight after 2 weeks | 380 g | 405 g | 425 g |
| Mean weight after 3 weeks | 696 g | 735 g | 779 g |
| Mean weight after 4 weeks | 985 g | 1142 g | 1238 g |
| Feed intake | 1710 g | 1850 g | 1880 g |
| Required Feed Ratio | 1.8 | 1.7 | 1.6 |

Example 29

Using 4 small-mesh fish pens stocked with 100 juvenile mackerel with a mean weight of 65 g, three fish pens were assigned to test groups and 1 to the untreated group. The fish were given moist pellets consisting of a 1:1 mixture of minced sardines and commercial yellowtail formula feed (Nisshin Feed, "Itomate"). In Test Group 1, the feed was mixed to $1 \times 10^9$ cells/g of feed with the *Lactobacillus casei* species of the present invention (FERM BP-10059, FERM P-19443) manufactured in Manufacturing Example 2, and given immediately. In Test Group 2, 0.02 ml/g of a culture solution of the same *Lactobacillus casei* species (FERM BP-10059, FERM P-19443) of the present invention manufactured in Manufacturing Example 2 was added to the feed. In Test Group 3, 0.02 ml/g of culture filtrate of the same *Lactobacillus casei* species (FERM BP-10059, FERM P-19443) of the present invention manufactured in Manufacturing Example 2 was added to the feed. The water temperature during the test period was 20° C. to 22° C. The results are shown in Table 51. As can be seen from Table 51, the mackerel in the test groups grew better than those in the untreated group, with less mortality during the test period. Of the test groups, the results were best for Test Group 2, which received a culture solution of the *Lactobacillus casei* species of the present invention.

TABLE 51

Mackerel feeding trial results using *lactobacillus* preparation of present invention

|  | Untreated group | Test Group 1 | Test Group 2 | Test Group 3 |
| --- | --- | --- | --- | --- |
| Initial mean weight | 65 g | 64 g | 65 g | 66 g |
| Final mean weight | 240 g | 280 g | 290 g | 255 g |
| Mean weight gain | 175 g | 216 g | 225 g | 189 g |
| Total feed intake | 275 kg | 275 kg | 275 kg | 275 kg |
| Growth rate | 270% | 338% | 346% | 286% |
| Deaths | 7 | 1 | 1 | 2 |

Comparative Example 8

The same test as in Example 29 was performed using the original *Lactobacillus casei* species (FERM BP-6971), with the results shown in Table 52. As shown in Table 52, the results were not as good as those obtained with the *Lactobacillus casei* species of the present invention.

TABLE 52

Mackerel feeding trial results using *lactobacillus* preparation of original *Lactobacillus casei* species

|  | Test Group 1 | Test Group 2 | Test Group 3 |
| --- | --- | --- | --- |
| Initial mean weight | 65 g | 64 g | 67 g |
| Final mean weight | 265 g | 275 g | 250 g |
| Mean weight gain | 200 g | 211 g | 183 g |
| Total feed intake | 275 kg | 275 kg | 275 kg |
| Growth rate | 307% | 330% | 273% |
| Deaths | 1 | 2 | 2 |

Example 30

A feeding trial was performed using red worms, which are valuable as bird feed and fishing bait. Four wooden boxes of W 600 mm×D 400 mm×H 150 mm were prepared and filled to 80% with a mixture of 1 kg of leaf mold mixed with 0.5 kg of raw bread yeast, after which 100 juvenile red worms with a mean length of 10 mm and a mean weight of 40 mg were placed in each box. These were reared in a room set to a room temperature of 25° C., with 10 lux of illumination in the daytime and no light at night. Test Group 1 was sprayed with 0.01 g of wet cell bodies of the *Lactobacillus casei* species of the present invention (FERM BP-10059, FERM P-19443) manufactured in Manufacturing Example 2, Test Group 2 was sprayed with 200 ml of a culture solution of the *Lactobacillus casei* species of the present invention (FERM BP-10059, FERM P-19443) manufactured in Manufacturing Example 2 diluted 100× with water, and Test Group 3 was sprayed with 200 ml of culture filtrate of the *Lactobacillus casei* species of the present invention (FERM BP-10059, FERM P-19443) manufactured in Manufacturing Example 2. This operation was performed once every 10 days, and the untreated group was sprayed with water. Each rearing box was sprayed with a suitable amount of water every other day so that the soil would not dry out. The worms were given dry yeast and chlorella as feed once a week, 1 g each at the beginning of rearing increasing 20% each week. The rearing results after 3 months are shown in Table 53. As shown in Table 53, the yield was better in Test Groups 1 and 2 than in the untreated group, and body weights were about 20% greater. The results for Test Group 3 were intermediate.

TABLE 53

Red worm feeding trial results

|  | Untreated group | Test Group 1 | Test Group 2 | Test Group 3 |
| --- | --- | --- | --- | --- |
| Initial mean length | 27 mm | 32 mm | 33 mm | 30 mm |
| Initial mean weight | 170 mg | 210 mg | 230 mg | 200 mg |
| % greater weight than in untreated group |  | 18.5% | 22.0% | 11.0% |
| Yield | 77% | 98% | 95% | 80% |

When feeding trials were also performed with juvenile beetles, silkworms and the like as well as red worms, those in the test groups grew faster and larger. In addition, the cocoons and adults were also larger. Good results were also obtained when the aforementioned tests were performed using the original *Lactobacillus casei* species, but growth rates and yields were 5 to 10% lower than with the *Lactobacillus casei* species of the present invention.

Example 31

Cucumbers were used to test prevention and treatment of powdery mildew and downy mildew, which are common problems in greenhouse cultivation. In powdery mildew disease the fungus invades from surface of the leaves and stalks, first forming white spots, but as the symptoms progress the leaf surfaces appear as if sprinkled with a white powder, gradually turning gray. Leaf growth stops, and in the case of cucumbers only small, thin hard cucumbers are harvested. In downy mildew disease, grayish-white mold-like spots first appear on the underside of the leaves, gradually forming irregular, dirty marks that continue to spread on the leaf surfaces. The leaves finally become yellow-brown and gluey and rot so that no harvest can be expected.

One section of a cucumber greenhouse was completely partitioned off, and 1 g of freeze-dried cells of the *Lactobacillus casei* species of the present invention (FERM BP-10059, FERM P-19443) manufactured in Manufacturing Example 1 mixed with 1 liter of water ($2 \times 10^7$ cells/ml) was sprayed thoroughly on the leaves and stalks before flowering. One week later, spores of powdery mildew (*Sphaeratheca fuliginea*) and downy mildew (*Pseudoperonospora cubensis*) were applied in amounts sufficient to cause the diseases, but instead of getting sick the plants flowered and the resulting cucumbers were if anything better than normal. Cucumber plants to which the spores were applied without previous application of the lactobacillus of the present invention all developed the diseases. Some cucumber plants (10 to 20% overall) sprayed with freeze-dried cell bodies obtained from the original *Lactobacillus casei* species (FERM BP-6971) developed the disease, and in this case cucumbers could not be harvested.

When cucumber plants infected as described above were thoroughly sprayed at the earliest stage of infection with a solution ($1 \times 10^8$ cells/ml) of 5 g of freeze-dried cells of the *Lactobacillus casei* species of the present invention (FERM BP-10059, FERM P-19443) manufactured in Manufacturing Example 1 suspended in 1 liter of water, and then sprayed with the same amount again a week later, the lesions gradually disappeared, flowering was normal, and fine cucumbers were obtained. When the original *Lactobacillus casei* species (FERM BP-6971) was applied in the same way, about 50% of the plants improved, but in the other 50% the diseases progressed and cucumbers could not be harvested.

Similar trials were performed using crops other than cucumbers including potatoes, peppers, pumpkins and the like, and in all cases application of freeze-dried cells of the *Lactobacillus casei* species of the present invention was shown to be effective. For example, good results were obtained when application of agricultural chemicals such as 3% thiophanate-methyl (Nippon Soda, Topsin-M) and quinoxaline (Yashima Chemical, Morestan) was reduced to ½ to ⅓, and a suitable amount of the lactobacillus preparation of the present invention was then applied.

Example 32

Four planters of W 600 mm×D 400 mm×H 150 mm were prepared, 20 g of chemical fertilizer (NAC Co. #38, N: 8%, P: 5%, K: 5%) and 5 g of fused magnesium phosphate was mixed with the lowest layer of soil in each, and soil consisting of 10 g of magnesium lime (NAC Co., soil improver consisting of 5 to 7% magnesium oxide mixed with slaked lime)

added to 10 L of a mixture of normal field soil with 30% leaf mold was laid on top to a depth of about 80%. In mid-August, 6 Allso strawberry seedlings were planted in each planter, and beginning two weeks later until mid-December, all the strawberry plants in the Test Group 1 planter were given liquid fertilizer each week and at the same time were sprayed thoroughly with freeze-dried cells of the *Lactobacillus casei* species of the present invention manufactured in Manufacturing Example 1 (FERM BP-10059, FERM P-19443) suspended $1 \times 10^7$ cells/ml in water. A 200× water dilution of culture liquid of the *Lactobacillus casei* species of the present invention manufactured in Manufacturing Example 1 (FERM BP-10059, FERM P-19443) was applied to Test Group 2. A 200× water dilution of culture filtrate of the *Lactobacillus casei* species of the present invention manufactured in Manufacturing Example 1 (FERM BP-10059, FERM P-19443) was applied to Test Group 3. Water alone was applied to the untreated planter. In March of the following year, once buds had developed liquid fertilizer and the aforementioned *lactobacillus* preparation were applied once a week. Red, ripe strawberries were gradually harvested 1 to 2 months after flowering. The results are shown in Table 54. As shown in Table 54, the strawberries in Test Groups 1 and 2, which received the *lactobacillus* preparation of the present invention, not only grew more quickly, but 200 g of strawberries were harvested per plant. Moreover, they were all found to be of the first quality in terms of smell, color, taste and size. By contrast, fewer strawberries were harvested in the untreated group, and they were of average quality, inferior to the high-quality strawberries in the test groups.

TABLE 54

Strawberry growth test results

|  |  | Untreated group | Test Group 1 | Test Group 2 | Test Group 3 |
|---|---|---|---|---|---|
| Harvest (days after flowering) |  | 35 to 60 days | 30 to 50 days | 30 to 50 days | 35 to 55 days |
| Yield per plant |  | 155 g | 185 g | 200 g | 175 g |
| QUALITY | Size | Medium | Large | Large | Med-large |
|  | Smell | + | +++ | +++ | ++ |
|  | Color | Yellow to dark red | Deep red | Deep red | Deep red |
|  | Gloss | + | ++ | ++ | + to ++ |
|  | Taste | Lacking sweetness, somewhat watery | Very sweet, good acidity, very tasty | Same as left | Very sweet, but somewhat poor acidity |

Example 33

Eight planters of W 600 mm×D 400 mm×H 150 mm were prepared, normal field soil was mixed with 30% leaf mold, and for the hornwort 8 g of magnesium lime (NAC Co., soil improver consisting of 5 to 7% magnesium oxide mixed with slaked lime) was added to 10 liters of this, and 1 week later the lower layer of soil in 3 planters was fertilized with 20 g of chemical fertilizer (NAC Co. #38, N: 8%, P: 5%, K: 5%). For the spinach, 20 g of magnesium lime was mixed well with 20 g of chemical fertilizer (NAC Co. #38, N: 8%, P: 5%, K: 5%) and added to 3 planters. Seeds were then planted in late September in the respective planters. When the hornwort and spinach sprouted they were thinned so that the leaves did not overlap, and once the main leaves began to develop they were fertilized once a week with liquid fertilizer and watered so that the soil did not dry out. When the liquid fertilizer was applied the plants in Group 1 were sprayed overall at the same time with freeze-dried cells of the *Lactobacillus casei* species of the present invention (FERM BP-10059, FERM P-19443) manufactured in Manufacturing Example 2 suspended $1 \times 10^7$ cells/ml in water. The plants in Test Group 2 were sprayed in the same way with a 300× dilution of a culture liquid of the *Lactobacillus casei* species of the present invention (FERM BP-10059, FERM P-19443) manufactured in Manufacturing Example 2. The plants in Test Group 3 were sprayed with a 300× dilution of culture filtrate of the *Lactobacillus casei* species of the present invention (FERM BP-10059, FERM P-19443) manufactured in Manufacturing Example 2. Water alone was sprayed in the untreated group. The results for hornwort are shown in Table 55. As shown in Table 55, the plants in Test Groups 1 and 2 which were treated with the *Lactobacillus casei* species of the present invention grew quickly, with wide, thick and soft leaves, and smelled much better than commercial, hydroponically grown hornwort. Hornwort of intermediate quality was harvested from Test Group 3.

TABLE 55

Hornwort growth test results

|  |  | Untreated group | Test Group 1 | Test Group 2 | Test Group 3 |
|---|---|---|---|---|---|
| Harvest |  | 35 days sowing to harvest (height 15 cm or more); weight per plant 80% of that in Test Group 1; hard if harvested late | 30 days to harvest; quality the same even if harvested somewhat late | 28 days to harvest; quality the same even if harvested somewhat late | 32 days to harvest; somewhat hard if harvested late |
| QUALITY | Smell | + | ++ | +++ | ++ |
|  | Other | Leaf size and thickness both average | Leaves large, thick but soft, stems also soft, leaves dark colored | Same as at left | Leaves average size, leaves and stems soft |

The results for spinach are shown in Table 56. As shown in Table 56, in the test groups the roots were redder and firmer than in the untreated group, and high quality deep green leaves were produced which were large, thick and glossy, emitting a unique sweetness. Some of the plants in the untreated group developed leaf spot disease (in which brown spots appear on the leaves, blackish-brown mold develops on the spots and the plants wither), but this did not occur in the treatment groups. Comparative tests were also performed using vegetables such as cabbage, parsley and celery, fruits such as grapes and oranges, Basidiomycetes such as mushrooms, ornamental plants such as pothos and flowers such as carnations, and in all cases a higher-quality crop was harvested more rapidly than in the untreated group, with very little occurrence of disease.

TABLE 56

| | Untreated group | Test group 1 | Test group 2 | Test group 3 |
|---|---|---|---|---|
| | Spinach growth test results | | | |
| Harvest | 50 days from sowing to harvest (when 5 to 6 main leaves appeared) | 40 days from sowing to harvest | Same as at left | 45 days from sowing to harvest |
| Quality | Characteristic sweetness somewhat weak | Leaves wide, thick and glossy, characteristic sweetness | Same as at left | Same as at left |

Example 34

Peppermint seedlings (with 6 leaves) were purchased, field soil was mixed with 50% leaf mold, Test Groups 1, 2 and 3 and an untreated group were established as in Examples 15 and 16 above, and the lactobacillus preparation of the present invention (FERM BP-10059, FERM P-19443) was sprayed once a week. The plants were fertilized separately once a month. As a result, the peppermint in Test Groups 1, 2 and 3 had denser leaves than in the untreated group, with a strong, characteristically sweet smell. Tests were also performed using other herbs including chamomile, sage, lavender and lemon balm, but the characteristic smells of the herbs seemed stronger as in the case of the peppermint. The aforementioned tests with vegetables and herbs were also performed using the original *Lactobacillus casei* species (FERM BP-6971), which was used in Japanese Patent Application Laid-open No. 2001-333766, but while the results were good, evaluating generally from yield, quality, smell, disease occurrence and the like they did not match the results obtained from application of the *Lactobacillus casei* species of the present invention (FERM BP-10059, FERM P-19443).

The invention claimed is:

1. A biologically pure culture of *Lactobacillus casei* strain FERM BP-10059 (FERM P-19443).

2. A *Lactobacillus* preparation comprising:
   $5 \times 10^9$ cells/g to $2 \times 10^{11}$ cells/g freeze-dried bacterial cells or wet bacterial cells of the biologically pure culture of the *Lactobacillus casei* strain according to claim 1; and
   a preservative.

\* \* \* \* \*